(12) United States Patent
Keast et al.

(10) Patent No.: US 8,932,316 B2
(45) Date of Patent: Jan. 13, 2015

(54) METHODS AND DEVICES FOR DIAGNOSING, MONITORING, OR TREATING MEDICAL CONDITIONS THROUGH AN OPENING THROUGH AN AIRWAY WALL

(71) Applicant: Broncus Medical Inc., Mountain View, CA (US)

(72) Inventors: Thomas Keast, Sunnyvale, CA (US); Michael D. Laufer, Menlo Park, CA (US); Henky Wibowo, Cupertino, CA (US); Cary Cole, Mountain View, CA (US); Gary S. Kaplan, Mountain View, CA (US); Edmund J. Roschak, Mission Viejo, CA (US)

(73) Assignee: Broncus Medical Inc., Mountain View, CA (US)

( * ) Notice: Subject to any disclaimer, the term of this patent is extended or adjusted under 35 U.S.C. 154(b) by 0 days.

(21) Appl. No.: 14/246,951

(22) Filed: Apr. 7, 2014

(65) Prior Publication Data
US 2014/0222015 A1    Aug. 7, 2014

Related U.S. Application Data

(63) Continuation of application No. 13/107,720, filed on May 13, 2011, now Pat. No. 8,709,034.

(51) Int. Cl.
*A61B 17/34* (2006.01)
*A61B 17/3209* (2006.01)
(Continued)

(52) U.S. Cl.
CPC ....... *A61B 17/3209* (2013.01); *A61B 2019/461* (2013.01); *A61B 2017/320056* (2013.01); *A61B 1/2676* (2013.01); *A61B 2017/00809* (2013.01); *A61B 17/0293* (2013.01); *A61B 2019/5255* (2013.01); *A61B 2017/0427* (2013.01); *A61B 2017/22042* (2013.01); *A61B 1/01* (2013.01); *A61B 2019/5445* (2013.01); *A61B 2017/0464* (2013.01); *A61B 17/221* (2013.01); *A61B 2019/5278* (2013.01); *A61B 1/00082* (2013.01); *A61B 2017/0417* (2013.01); *A61B 2017/00867* (2013.01); *A61B 2017/22034* (2013.01); *A61B 17/0401* (2013.01); *A61B 1/313* (2013.01); *A61B 17/3478* (2013.01); *A61B 2017/0419* (2013.01); *A61B 2019/5251* (2013.01); *A61B 2019/5257* (2013.01)
USPC ....................................... 606/185

(58) Field of Classification Search
USPC .......... 128/898; 604/500, 506, 507, 508, 510; 606/151, 184, 185
See application file for complete search history.

(56) References Cited

U.S. PATENT DOCUMENTS 2,127,903 A   8/1938  Bowen
3,174,851 A   3/1965  Buehler et al.
(Continued)

FOREIGN PATENT DOCUMENTS

EP   0316789 A2   5/1989
EP   0347098 A2   12/1989
(Continued)

OTHER PUBLICATIONS

Choong, C., et al., "Feasibility and safety of airway bypass stent placement and influence of topical mitomycin C on stent patency," *J. Thorac. Cardiovasc Surg.*, 129:632-638, 2005.
(Continued)

*Primary Examiner* — Ashley Fishback
(74) *Attorney, Agent, or Firm* — Levine Bagade Han LLP

(57) ABSTRACT

Methods and devices for diagnosing, monitoring, and/or treating tissue through an opening or port through an airway wall are provided herein.

20 Claims, 28 Drawing Sheets

(51) Int. Cl.
*A61B 17/221* (2006.01)
*A61B 19/00* (2006.01)
*A61B 17/32* (2006.01)
*A61B 1/267* (2006.01)
*A61B 17/00* (2006.01)
*A61B 17/02* (2006.01)
*A61B 17/04* (2006.01)
*A61B 17/22* (2006.01)
*A61B 1/01* (2006.01)
*A61B 1/00* (2006.01)
*A61B 1/313* (2006.01)

(56) References Cited

U.S. PATENT DOCUMENTS

| | | |
|---|---|---|
| 3,351,463 A | 11/1967 | Rozner et al. |
| 3,406,685 A | 10/1968 | May |
| 3,433,226 A | 3/1969 | Boyd |
| 3,556,079 A | 1/1971 | Omizo |
| 3,565,062 A | 2/1971 | Kuris |
| 3,617,060 A | 11/1971 | Lezzi |
| 3,707,151 A | 12/1972 | Jackson |
| 3,753,700 A | 8/1973 | Harrison et al. |
| 3,779,234 A | 12/1973 | Eggleton et al. |
| 3,823,717 A | 7/1974 | Pohlman et al. |
| 3,874,388 A | 4/1975 | King et al. |
| 3,889,688 A | 6/1975 | Eamkaow |
| 3,942,530 A | 3/1976 | Northeved |
| 4,249,539 A | 2/1981 | Vilkomerson et al. |
| 4,249,541 A | 2/1981 | Pratt |
| 4,319,580 A | 3/1982 | Colley et al. |
| 4,324,235 A | 4/1982 | Beran |
| 4,327,739 A | 5/1982 | Chmiel et al. |
| 4,332,254 A | 6/1982 | Lundquist |
| 4,355,426 A | 10/1982 | MacGregor |
| 4,407,294 A | 10/1983 | Vilkomerson |
| 4,431,006 A | 2/1984 | Trimmer et al. |
| 4,469,142 A | 9/1984 | Harwood |
| 4,493,320 A | 1/1985 | Treat |
| 4,503,569 A | 3/1985 | Dotter |
| 4,534,761 A | 8/1985 | Raible |
| 4,538,606 A | 9/1985 | Whited |
| 4,538,618 A | 9/1985 | Rosenberg et al. |
| 4,582,067 A | 4/1986 | Silverstein et al. |
| 4,583,969 A | 4/1986 | Mortensen |
| 4,622,968 A | 11/1986 | Persson |
| 4,655,771 A | 4/1987 | Wallsten |
| 4,658,817 A | 4/1987 | Hardy |
| 4,674,498 A | 6/1987 | Stasz |
| 4,676,782 A | 6/1987 | Yamamoto et al. |
| 4,682,596 A | 7/1987 | Bales et al. |
| 4,687,482 A | 8/1987 | Hanson |
| 4,702,252 A | 10/1987 | Brooks et al. |
| 4,706,689 A | 11/1987 | Man |
| 4,750,902 A | 6/1988 | Wuchinich et al. |
| 4,753,236 A | 6/1988 | Healey |
| 4,757,821 A | 7/1988 | Snyder |
| 4,757,822 A | 7/1988 | Di Giuliomaria et al. |
| 4,767,627 A | 8/1988 | Caldwell et al. |
| 4,769,031 A | 9/1988 | McGough et al. |
| 4,770,185 A | 9/1988 | Silverstein et al. |
| 4,771,788 A | 9/1988 | Millar |
| 4,773,413 A | 9/1988 | Hussein et al. |
| 4,781,676 A | 11/1988 | Schweighardt et al. |
| 4,785,402 A | 11/1988 | Matsuo et al. |
| 4,795,465 A | 1/1989 | Marten |
| 4,802,476 A | 2/1989 | Noerenberg et al. |
| 4,807,634 A | 2/1989 | Enjoji et al. |
| 4,808,153 A | 2/1989 | Parisi |
| 4,834,102 A | 5/1989 | Schwarzschild et al. |
| 4,855,563 A | 8/1989 | Beresnev et al. |
| 4,869,268 A | 9/1989 | Yoon |
| 4,870,953 A | 10/1989 | Don Micheal et al. |
| 4,887,606 A | 12/1989 | Yock et al. |
| 4,892,098 A | 1/1990 | Sauer |
| 4,892,099 A | 1/1990 | Ohkawa et al. |
| 4,899,757 A | 2/1990 | Pope, Jr. et al. |
| 4,917,097 A | 4/1990 | Proudian et al. |
| 4,920,954 A | 5/1990 | Alliger et al. |
| 4,921,483 A | 5/1990 | Wijay et al. |
| 4,924,863 A | 5/1990 | Sterzer |
| 4,930,525 A | 6/1990 | Palestrant |
| 4,936,281 A | 6/1990 | Stasz |
| 4,955,377 A | 9/1990 | Lennox et al. |
| 4,957,508 A | 9/1990 | Kaneko et al. |
| 4,966,162 A | 10/1990 | Wang |
| 4,967,753 A | 11/1990 | Haase et al. |
| 4,973,301 A | 11/1990 | Nissenkorn |
| 4,976,690 A | 12/1990 | Solar et al. |
| 4,977,898 A | 12/1990 | Schwarzschild et al. |
| 4,991,602 A | 2/1991 | Amplatz et al. |
| 5,002,058 A | 3/1991 | Martinelli |
| 5,030,201 A | 7/1991 | Palestrant |
| 5,042,981 A | 8/1991 | Gross |
| 5,047,026 A | 9/1991 | Rydell |
| 5,054,483 A | 10/1991 | Marten et al. |
| 5,061,275 A | 10/1991 | Wallsten et al. |
| 5,064,435 A | 11/1991 | Porter |
| 5,069,664 A | 12/1991 | Guess et al. |
| 5,081,993 A | 1/1992 | Kitney et al. |
| 5,100,423 A | 3/1992 | Fearnot |
| 5,102,417 A | 4/1992 | Palmaz |
| 5,105,816 A | 4/1992 | Shimura et al. |
| 5,105,817 A | 4/1992 | Uchibori et al. |
| 5,123,917 A | 6/1992 | Lee |
| 5,125,926 A | 6/1992 | Rudko et al. |
| 5,127,917 A | 7/1992 | Niederhauser et al. |
| 5,131,394 A | 7/1992 | Gehlbach |
| 5,145,684 A | 9/1992 | Liversidge et al. |
| 5,148,809 A | 9/1992 | Biegeleisen-Knight et al. |
| 5,155,435 A | 10/1992 | Kaufman et al. |
| 5,170,793 A | 12/1992 | Takano et al. |
| 5,178,635 A | 1/1993 | Gwon et al. |
| 5,190,528 A | 3/1993 | Fonger et al. |
| 5,201,316 A | 4/1993 | Pomeranz et al. |
| 5,201,741 A | 4/1993 | Dulebohn |
| 5,209,721 A | 5/1993 | Wilk |
| 5,220,924 A | 6/1993 | Frazin |
| 5,226,421 A | 7/1993 | Frisbie et al. |
| 5,234,447 A | 8/1993 | Kaster et al. |
| 5,238,027 A | 8/1993 | Lee |
| 5,246,011 A | 9/1993 | Caillouette |
| 5,246,014 A | 9/1993 | Williams et al. |
| 5,254,112 A | 10/1993 | Sinofsky et al. |
| 5,257,990 A | 11/1993 | Nash |
| 5,259,385 A | 11/1993 | Miller et al. |
| 5,261,409 A | 11/1993 | Dardel |
| 5,263,992 A | 11/1993 | Guire |
| 5,269,326 A | 12/1993 | Verrier |
| 5,273,529 A | 12/1993 | Idowu |
| 5,275,166 A | 1/1994 | Vaitekunas et al. |
| 5,282,799 A | 2/1994 | Rydell |
| 5,282,824 A | 2/1994 | Gianturco |
| 5,287,861 A | 2/1994 | Wilk |
| 5,295,484 A | 3/1994 | Marcus et al. |
| 5,299,578 A | 4/1994 | Rotteveel et al. |
| 5,304,200 A | 4/1994 | Spaulding |
| 5,309,915 A | 5/1994 | Ember |
| 5,311,871 A | 5/1994 | Yock |
| 5,313,950 A | 5/1994 | Ishikawa et al. |
| 5,316,001 A | 5/1994 | Ferek-Petric et al. |
| 5,318,564 A | 6/1994 | Eggers |
| 5,320,106 A | 6/1994 | Tanaka |
| 5,330,500 A | 7/1994 | Song |
| 5,334,146 A | 8/1994 | Ozasa |
| 5,334,183 A | 8/1994 | Wuchinich |
| 5,334,210 A | 8/1994 | Gianturco |
| 5,338,305 A | 8/1994 | Plyley et al. |
| 5,339,289 A | 8/1994 | Erickson |
| 5,344,420 A | 9/1994 | Hilal et al. |
| 5,351,693 A | 10/1994 | Taimisto et al. |
| 5,363,852 A | 11/1994 | Sharkawy |
| 5,363,853 A | 11/1994 | Lieber et al. |

(56) References Cited

U.S. PATENT DOCUMENTS

| | | |
|---|---|---|
| 5,366,504 A | 11/1994 | Andersen et al. |
| 5,368,035 A | 11/1994 | Hamm et al. |
| 5,372,138 A | 12/1994 | Crowley et al. |
| 5,375,602 A | 12/1994 | Lancee et al. |
| 5,377,682 A | 1/1995 | Ueno et al. |
| 5,380,316 A | 1/1995 | Aita et al. |
| 5,381,795 A | 1/1995 | Nordgren et al. |
| 5,383,460 A | 1/1995 | Jang et al. |
| 5,383,887 A | 1/1995 | Nadal |
| 5,385,148 A | 1/1995 | Lesh et al. |
| 5,389,096 A | 2/1995 | Aita et al. |
| 5,402,792 A | 4/1995 | Kimura |
| 5,409,012 A | 4/1995 | Sahatjian |
| 5,409,019 A | 4/1995 | Wilk |
| 5,411,466 A | 5/1995 | Hess |
| 5,413,601 A | 5/1995 | Keshelava |
| 5,421,955 A | 6/1995 | Lau |
| 5,425,739 A | 6/1995 | Jessen |
| 5,427,107 A | 6/1995 | Milo et al. |
| 5,429,144 A | 7/1995 | Wilk |
| 5,435,314 A | 7/1995 | Dias |
| 5,441,515 A | 8/1995 | Khosravi et al. |
| 5,443,498 A | 8/1995 | Fontaine |
| 5,443,843 A | 8/1995 | Curatolo et al. |
| 5,452,733 A | 9/1995 | Sterman et al. |
| 5,454,373 A | 10/1995 | Koger et al. |
| 5,454,809 A | 10/1995 | Janssen |
| 5,456,258 A | 10/1995 | Kondo et al. |
| 5,458,120 A | 10/1995 | Lorraine |
| 5,464,016 A | 11/1995 | Nicholas et al. |
| 5,465,726 A | 11/1995 | Dickinson et al. |
| 5,466,242 A | 11/1995 | Mori |
| 5,470,308 A | 11/1995 | Edwards et al. |
| 5,474,075 A | 12/1995 | Goldberg et al. |
| 5,474,543 A | 12/1995 | McKay |
| 5,484,416 A | 1/1996 | Gittings |
| 5,485,841 A | 1/1996 | Watkin et al. |
| 5,500,012 A | 3/1996 | Brucker et al. |
| 5,505,088 A | 4/1996 | Chandraratna et al. |
| 5,509,900 A | 4/1996 | Kirkman |
| 5,514,154 A | 5/1996 | Lau et al. |
| 5,520,684 A | 5/1996 | Imran |
| 5,522,822 A | 6/1996 | Phelps et al. |
| 5,524,630 A | 6/1996 | Crowley |
| 5,527,292 A | 6/1996 | Adams et al. |
| 5,527,324 A | 6/1996 | Krantz et al. |
| 5,531,780 A | 7/1996 | Vachon |
| 5,536,240 A | 7/1996 | Edwards et al. |
| 5,540,713 A | 7/1996 | Schnepp-Pesch et al. |
| 5,545,195 A | 8/1996 | Lennox et al. |
| 5,545,208 A | 8/1996 | Wolff et al. |
| 5,545,210 A | 8/1996 | Hess et al. |
| 5,554,118 A | 9/1996 | Jang |
| 5,554,152 A | 9/1996 | Aita et al. |
| 5,554,181 A | 9/1996 | Das |
| 5,555,886 A | 9/1996 | Weng et al. |
| 5,562,922 A | 10/1996 | Lambert |
| 5,564,434 A | 10/1996 | Halperin et al. |
| 5,571,086 A | 11/1996 | Kaplan et al. |
| 5,571,180 A | 11/1996 | Blom |
| 5,573,531 A | 11/1996 | Gregory |
| 5,575,815 A | 11/1996 | Slepian et al. |
| 5,575,818 A | 11/1996 | Pinchuk |
| 5,588,432 A | 12/1996 | Crowley |
| 5,593,417 A | 1/1997 | Rhodes |
| 5,593,442 A | 1/1997 | Klein |
| 5,596,989 A | 1/1997 | Morita |
| 5,607,444 A | 3/1997 | Lam |
| 5,615,679 A | 4/1997 | Ri et al. |
| 5,616,608 A | 4/1997 | Kinsella et al. |
| 5,618,301 A | 4/1997 | Hauenstein et al. |
| 5,629,678 A | 5/1997 | Gargano et al. |
| 5,629,687 A | 5/1997 | Sutton et al. |
| 5,630,837 A | 5/1997 | Crowley |
| D380,266 S | 6/1997 | Boatman et al. |
| 5,638,819 A | 6/1997 | Manwaring et al. |
| 5,645,559 A | 7/1997 | Hachtman et al. |
| 5,647,871 A | 7/1997 | Levine et al. |
| 5,653,746 A | 8/1997 | Schmitt |
| 5,655,548 A | 8/1997 | Nelson et al. |
| 5,658,279 A | 8/1997 | Nardella et al. |
| 5,658,280 A | 8/1997 | Issa |
| 5,672,172 A | 9/1997 | Zupkas |
| 5,674,242 A | 10/1997 | Phan et al. |
| 5,674,277 A | 10/1997 | Freitag |
| 5,674,298 A | 10/1997 | Levy et al. |
| 5,678,555 A | 10/1997 | O'Connell |
| 5,682,880 A | 11/1997 | Brain |
| 5,693,085 A | 12/1997 | Buirge et al. |
| 5,702,418 A | 12/1997 | Ravenscroft |
| 5,704,361 A | 1/1998 | Seward et al. |
| 5,713,949 A | 2/1998 | Jayaraman |
| 5,716,393 A | 2/1998 | Lindenberg et al. |
| 5,718,701 A | 2/1998 | Shai et al. |
| 5,720,735 A | 2/1998 | Dorros |
| 5,725,521 A | 3/1998 | Mueller |
| 5,725,547 A | 3/1998 | Chuter |
| 5,725,572 A | 3/1998 | Lam et al. |
| 5,728,068 A | 3/1998 | Leone et al. |
| 5,733,301 A | 3/1998 | Forman |
| 5,736,642 A | 4/1998 | Yost et al. |
| 5,741,234 A | 4/1998 | Aboul-Hosn |
| 5,741,333 A | 4/1998 | Frid |
| 5,746,767 A | 5/1998 | Smith |
| 5,752,518 A | 5/1998 | McGee et al. |
| 5,755,769 A | 5/1998 | Richard et al. |
| 5,755,778 A | 5/1998 | Kleshinski |
| 5,759,174 A | 6/1998 | Fischell et al. |
| 5,759,769 A | 6/1998 | Sia et al. |
| 5,762,638 A | 6/1998 | Shikani et al. |
| 5,779,642 A | 7/1998 | Nightengale |
| 5,782,762 A | 7/1998 | Vining |
| 5,792,119 A | 8/1998 | Marx |
| 5,795,325 A | 8/1998 | Valley et al. |
| 5,797,920 A | 8/1998 | Kim |
| 5,807,261 A | 9/1998 | Benaron et al. |
| 5,810,008 A | 9/1998 | Dekel et al. |
| 5,810,836 A | 9/1998 | Hussein et al. |
| 5,819,723 A | 10/1998 | Joseph |
| 5,824,046 A | 10/1998 | Smith et al. |
| 5,824,048 A | 10/1998 | Tuch |
| 5,830,191 A | 11/1998 | Hildwein et al. |
| 5,830,222 A | 11/1998 | Makower |
| 5,840,431 A | 11/1998 | Kall |
| 5,843,079 A | 12/1998 | Suslov |
| 5,843,158 A | 12/1998 | Lenker et al. |
| 5,843,175 A | 12/1998 | Frantzen |
| 5,846,205 A | 12/1998 | Curley et al. |
| 5,849,037 A | 12/1998 | Frid |
| 5,851,210 A | 12/1998 | Torossian |
| 5,855,597 A | 1/1999 | Jayaraman |
| 5,855,598 A | 1/1999 | Pinchuk |
| 5,860,920 A | 1/1999 | McGee et al. |
| 5,860,951 A | 1/1999 | Eggers et al. |
| 5,868,763 A | 2/1999 | Spence et al. |
| 5,868,777 A | 2/1999 | Lam |
| 5,873,904 A | 2/1999 | Ragheb et al. |
| 5,876,345 A | 3/1999 | Eaton et al. |
| 5,876,434 A | 3/1999 | Flomenblit et al. |
| 5,876,445 A | 3/1999 | Andersen et al. |
| 5,876,448 A | 3/1999 | Thompson et al. |
| 5,885,219 A | 3/1999 | Nightengale |
| 5,906,587 A | 5/1999 | Zimmon |
| 5,906,621 A | 5/1999 | Secrest et al. |
| 5,908,448 A | 6/1999 | Roberts et al. |
| 5,911,702 A | 6/1999 | Romley et al. |
| 5,916,158 A | 6/1999 | Webster, Jr. |
| 5,919,191 A | 7/1999 | Lennox et al. |
| 5,922,019 A | 7/1999 | Hankh et al. |
| 5,935,135 A | 8/1999 | Bramfitt et al. |
| 5,938,697 A | 8/1999 | Killion et al. |
| 5,951,567 A | 9/1999 | Javier, Jr. et al. |
| 5,954,636 A | 9/1999 | Schwartz et al. |
| 5,954,649 A | 9/1999 | Chia et al. |

(56) References Cited

U.S. PATENT DOCUMENTS

| | | |
|---|---|---|
| 5,957,849 A | 9/1999 | Munro |
| 5,957,919 A | 9/1999 | Laufer |
| 5,957,949 A | 9/1999 | Leonhardt et al. |
| 5,957,974 A | 9/1999 | Thompson et al. |
| 5,967,990 A | 10/1999 | Thierman et al. |
| 5,968,053 A | 10/1999 | Revelas |
| 5,968,070 A | 10/1999 | Bley et al. |
| 5,971,767 A | 10/1999 | Kaufman et al. |
| 5,971,980 A | 10/1999 | Sherman |
| 5,972,017 A | 10/1999 | Berg et al. |
| 5,976,178 A | 11/1999 | Goldsteen et al. |
| 5,984,871 A | 11/1999 | TenHoff et al. |
| 5,989,276 A | 11/1999 | Houser et al. |
| 5,993,484 A | 11/1999 | Shmulewitz |
| 6,001,124 A | 12/1999 | Bachinski |
| 6,002,955 A | 12/1999 | Willems et al. |
| 6,003,517 A | 12/1999 | Sheffield et al. |
| 6,004,269 A | 12/1999 | Crowley et al. |
| 6,004,273 A | 12/1999 | Sakamoto et al. |
| 6,004,319 A | 12/1999 | Goble et al. |
| 6,007,544 A | 12/1999 | Kim |
| 6,007,546 A | 12/1999 | Snow et al. |
| 6,007,574 A | 12/1999 | Pulnev et al. |
| 6,010,529 A | 1/2000 | Herweck et al. |
| 6,011,995 A | 1/2000 | Guglielmi et al. |
| 6,013,033 A | 1/2000 | Berger et al. |
| 6,013,093 A | 1/2000 | Nott et al. |
| 6,013,854 A | 1/2000 | Moriuchi |
| 6,015,405 A | 1/2000 | Schwartz et al. |
| 6,015,415 A | 1/2000 | Avelianet |
| 6,019,787 A | 2/2000 | Richard et al. |
| 6,019,789 A | 2/2000 | Dinh et al. |
| 6,022,371 A | 2/2000 | Killion |
| 6,024,703 A | 2/2000 | Zanelli et al. |
| 6,024,756 A | 2/2000 | Huebsch et al. |
| 6,030,392 A | 2/2000 | Dakov |
| 6,032,674 A | 3/2000 | Eggers et al. |
| 6,036,702 A | 3/2000 | Bachinski et al. |
| 6,045,511 A | 4/2000 | Ott et al. |
| 6,045,532 A | 4/2000 | Eggers et al. |
| 6,048,362 A | 4/2000 | Berg |
| 6,053,940 A | 4/2000 | Wijay |
| 6,053,941 A | 4/2000 | Lindenberg et al. |
| 6,059,731 A | 5/2000 | Seward et al. |
| 6,059,811 A | 5/2000 | Pinchasik et al. |
| 6,063,111 A | 5/2000 | Hieshima et al. |
| 6,064,902 A | 5/2000 | Haissaguerre et al. |
| 6,066,169 A | 5/2000 | McGuinness |
| 6,068,638 A | 5/2000 | Makower |
| 6,070,094 A | 5/2000 | Swanson et al. |
| 6,074,349 A | 6/2000 | Crowley |
| 6,074,362 A | 6/2000 | Jang et al. |
| 6,074,416 A | 6/2000 | Berg et al. |
| 6,080,109 A | 6/2000 | Baker et al. |
| 6,080,182 A | 6/2000 | Shaw et al. |
| 6,083,162 A | 7/2000 | Vining |
| 6,093,195 A | 7/2000 | Ouchi |
| 6,096,053 A | 8/2000 | Bates |
| 6,099,563 A | 8/2000 | Zhong |
| 6,102,887 A | 8/2000 | Altman |
| 6,112,123 A | 8/2000 | Kelleher et al. |
| 6,113,612 A | 9/2000 | Swanson et al. |
| 6,117,101 A | 9/2000 | Diederich et al. |
| 6,120,432 A | 9/2000 | Sullivan et al. |
| 6,120,534 A | 9/2000 | Ruiz |
| 6,120,803 A | 9/2000 | Wong et al. |
| 6,124,523 A | 9/2000 | Banas et al. |
| 6,129,726 A | 10/2000 | Edwards et al. |
| 6,135,997 A | 10/2000 | Laufer et al. |
| 6,143,019 A | 11/2000 | Motamedi et al. |
| 6,152,937 A | 11/2000 | Peterson et al. |
| 6,152,945 A | 11/2000 | Bachinski et al. |
| 6,159,225 A | 12/2000 | Makower |
| 6,162,245 A | 12/2000 | Jayaraman |
| 6,165,127 A | 12/2000 | Crowley |
| 6,174,323 B1 | 1/2001 | Biggs et al. |
| 6,176,872 B1 | 1/2001 | Miksza |
| 6,181,348 B1 | 1/2001 | Geiger |
| 6,183,444 B1 | 2/2001 | Glines et al. |
| 6,186,942 B1 | 2/2001 | Sullivan et al. |
| 6,188,355 B1 | 2/2001 | Gilboa |
| 6,190,353 B1 | 2/2001 | Makower et al. |
| 6,197,042 B1 | 3/2001 | Ginn et al. |
| 6,200,313 B1 | 3/2001 | Abe et al. |
| 6,200,564 B1 | 3/2001 | Lamont et al. |
| 6,206,831 B1 | 3/2001 | Suorsa et al. |
| 6,226,543 B1 | 5/2001 | Gilboa et al. |
| 6,231,587 B1 | 5/2001 | Makower |
| 6,235,024 B1 | 5/2001 | Tu |
| 6,235,054 B1 | 5/2001 | Berg et al. |
| 6,239,705 B1 | 5/2001 | Glen |
| 6,241,742 B1 | 6/2001 | Spence et al. |
| 6,241,746 B1 | 6/2001 | Bosma et al. |
| 6,245,020 B1 | 6/2001 | Moore et al. |
| 6,245,057 B1 | 6/2001 | Sieben et al. |
| 6,245,102 B1 | 6/2001 | Jayaraman |
| 6,246,784 B1 | 6/2001 | Summers et al. |
| 6,254,632 B1 | 7/2001 | Wu et al. |
| 6,258,100 B1 | 7/2001 | Alferness et al. |
| 6,258,115 B1 | 7/2001 | Dubrul |
| 6,261,601 B1 | 7/2001 | Talwar et al. |
| 6,264,690 B1 | 7/2001 | Von Oepen |
| 6,270,515 B1 | 8/2001 | Linden et al. |
| 6,270,524 B1 | 8/2001 | Kim |
| 6,272,366 B1 | 8/2001 | Vining |
| 6,273,907 B1 | 8/2001 | Laufer |
| 6,280,457 B1 | 8/2001 | Wallace et al. |
| 6,283,951 B1 | 9/2001 | Flaherty et al. |
| 6,283,983 B1 | 9/2001 | Makower et al. |
| 6,283,988 B1 | 9/2001 | Laufer et al. |
| 6,287,290 B1 | 9/2001 | Perkins et al. |
| 6,290,728 B1 | 9/2001 | Phelps et al. |
| 6,293,951 B1 | 9/2001 | Alferness et al. |
| 6,299,604 B1 | 10/2001 | Ragheb et al. |
| 6,299,635 B1 | 10/2001 | Frantzen |
| 6,306,096 B1 | 10/2001 | Seward et al. |
| 6,306,097 B1 | 10/2001 | Park et al. |
| 6,309,375 B1 | 10/2001 | Glines et al. |
| 6,309,415 B1 | 10/2001 | Pulnev et al. |
| 6,309,416 B1 | 10/2001 | Swanson et al. |
| 6,325,825 B1 | 12/2001 | Kula et al. |
| 6,328,689 B1 | 12/2001 | Gonzalez et al. |
| 6,331,116 B1 | 12/2001 | Kaufman et al. |
| 6,334,869 B1 | 1/2002 | Leonhardt et al. |
| 6,335,029 B1 | 1/2002 | Kamath et al. |
| 6,336,933 B1 | 1/2002 | Parodi |
| 6,342,591 B1 | 1/2002 | Zamora et al. |
| 6,343,936 B1 | 2/2002 | Kaufman et al. |
| 6,344,053 B1 | 2/2002 | Boneau |
| 6,346,940 B1 | 2/2002 | Fukunaga |
| 6,355,057 B1 | 3/2002 | DeMarais et al. |
| 6,371,964 B1 | 4/2002 | Vargas et al. |
| 6,379,382 B1 | 4/2002 | Yang |
| 6,380,732 B1 | 4/2002 | Gilboa |
| 6,391,036 B1 | 5/2002 | Berg et al. |
| 6,394,093 B1 | 5/2002 | Lethi |
| 6,394,956 B1 | 5/2002 | Chandrasekaran et al. |
| 6,409,686 B1 | 6/2002 | Guthrie et al. |
| 6,411,852 B1 | 6/2002 | Danek et al. |
| 6,428,550 B1 | 8/2002 | Vargas et al. |
| 6,440,163 B1 | 8/2002 | Swanson et al. |
| 6,451,048 B1 | 9/2002 | Berg et al. |
| 6,458,153 B1 | 10/2002 | Bailey et al. |
| 6,466,687 B1 | 10/2002 | Uppaluri et al. |
| 6,488,673 B1 | 12/2002 | Laufer et al. |
| 6,490,474 B1 | 12/2002 | Willis et al. |
| 6,493,589 B1 | 12/2002 | Medhkour et al. |
| 6,505,065 B1 | 1/2003 | Yanof et al. |
| 6,506,408 B1 | 1/2003 | Palasis |
| 6,508,822 B1 | 1/2003 | Peterson et al. |
| 6,511,491 B2 | 1/2003 | Grudem et al. |
| 6,514,249 B1 | 2/2003 | Maguire et al. |
| 6,514,290 B1 | 2/2003 | Loomas |
| 6,516,213 B1 | 2/2003 | Nevo |

(56) References Cited

U.S. PATENT DOCUMENTS

| | | |
|---|---|---|
| 6,528,301 B1 | 3/2003 | Breme et al. |
| 6,533,812 B2 | 3/2003 | Swanson et al. |
| 6,551,302 B1 | 4/2003 | Rosinko et al. |
| 6,554,848 B2 | 4/2003 | Boylan et al. |
| 6,556,696 B1 | 4/2003 | Summers et al. |
| 6,558,333 B2 | 5/2003 | Gilboa et al. |
| 6,574,498 B1 | 6/2003 | Gilboa |
| 6,575,969 B1 | 6/2003 | Rittman et al. |
| 6,585,655 B2 | 7/2003 | Crowley |
| 6,593,884 B1 | 7/2003 | Gilboa et al. |
| 6,599,303 B1 | 7/2003 | Peterson et al. |
| 6,599,311 B1 | 7/2003 | Biggs et al. |
| 6,602,263 B1 | 8/2003 | Swanson et al. |
| 6,615,155 B2 | 9/2003 | Gilboa |
| 6,616,675 B1 | 9/2003 | Evard et al. |
| 6,620,176 B1 | 9/2003 | Peterson et al. |
| 6,623,437 B2 | 9/2003 | Hinchliffe et al. |
| 6,623,448 B2 | 9/2003 | Slater |
| 6,629,951 B2 | 10/2003 | Laufer et al. |
| 6,634,363 B1 | 10/2003 | Danek et al. |
| 6,635,279 B2 | 10/2003 | Kolter et al. |
| 6,635,281 B2 | 10/2003 | Wong et al. |
| 6,650,923 B1 | 11/2003 | Lesh et al. |
| 6,652,577 B2 | 11/2003 | Gianotti |
| 6,652,582 B1 | 11/2003 | Stinson |
| 6,660,015 B1 | 12/2003 | Berg et al. |
| 6,663,662 B2 | 12/2003 | Pacetti et al. |
| 6,667,051 B1 | 12/2003 | Gregory |
| 6,673,084 B1 | 1/2004 | Peterson et al. |
| 6,689,803 B2 | 2/2004 | Hunter |
| 6,692,494 B1 | 2/2004 | Cooper et al. |
| 6,694,163 B1 | 2/2004 | Vining |
| 6,695,859 B1 | 2/2004 | Golden et al. |
| 6,699,256 B1 | 3/2004 | Logan et al. |
| 6,702,780 B1 | 3/2004 | Gilboa et al. |
| 6,702,829 B2 | 3/2004 | Bachinski et al. |
| 6,711,429 B1 | 3/2004 | Gilboa et al. |
| 6,712,804 B2 | 3/2004 | Roue et al. |
| 6,712,812 B2 | 3/2004 | Roschak et al. |
| 6,712,845 B2 | 3/2004 | Hossainy |
| 6,719,698 B2 | 4/2004 | Manor et al. |
| 6,719,781 B1 | 4/2004 | Kim |
| 6,730,064 B2 | 5/2004 | Ragheb et al. |
| 6,730,349 B2 | 5/2004 | Schwarz et al. |
| 6,749,576 B2 | 6/2004 | Bauer |
| 6,749,606 B2 | 6/2004 | Keast et al. |
| 6,770,070 B1 | 8/2004 | Balbierz |
| 6,773,457 B2 | 8/2004 | Ivancev et al. |
| 6,785,410 B2 | 8/2004 | Vining et al. |
| 6,790,228 B2 | 9/2004 | Hossainy et al. |
| 6,819,785 B1 | 11/2004 | Vining et al. |
| 6,829,379 B1 | 12/2004 | Knoplioch et al. |
| 6,833,814 B2 | 12/2004 | Gilboa et al. |
| 6,852,111 B1 | 2/2005 | Lieber |
| 6,866,674 B2 | 3/2005 | Galdonik et al. |
| 6,869,443 B2 | 3/2005 | Buscemi et al. |
| 6,872,183 B2 | 3/2005 | Sampson et al. |
| 6,886,558 B2 | 5/2005 | Tanaka |
| 6,890,583 B2 | 5/2005 | Chudzik et al. |
| 6,899,731 B2 | 5/2005 | Li et al. |
| 6,909,913 B2 | 6/2005 | Vining |
| 6,918,869 B2 | 7/2005 | Shaw et al. |
| 6,918,927 B2 | 7/2005 | Bates et al. |
| 6,920,882 B2 | 7/2005 | Berg et al. |
| 6,929,637 B2 | 8/2005 | Gonzalez et al. |
| 6,941,950 B2 | 9/2005 | Wilson et al. |
| 6,960,219 B2 | 11/2005 | Grudem et al. |
| 6,961,600 B2 | 11/2005 | Kohl et al. |
| 6,970,733 B2 | 11/2005 | Willis et al. |
| 6,994,713 B2 | 2/2006 | Berg et al. |
| 6,996,430 B1 | 2/2006 | Gilboa et al. |
| 6,997,189 B2 | 2/2006 | Biggs et al. |
| 7,011,094 B2 | 3/2006 | Rapacki et al. |
| 7,014,654 B2 | 3/2006 | Welsh et al. |
| 7,022,088 B2 | 4/2006 | Keast et al. |
| 7,052,501 B2 | 5/2006 | McGuckin |
| 7,086,398 B2 | 8/2006 | Tanaka |
| 7,149,564 B2 | 12/2006 | Vining et al. |
| 7,169,164 B2 | 1/2007 | Borillo et al. |
| 7,175,644 B2 | 2/2007 | Cooper et al. |
| 7,179,220 B2 | 2/2007 | Kukuk |
| 7,191,101 B2 | 3/2007 | Knoplioch et al. |
| 7,226,442 B2 | 6/2007 | Sheppard, Jr. et al. |
| 7,226,472 B2 | 6/2007 | Pederson, Jr. et al. |
| 7,232,409 B2 | 6/2007 | Hale et al. |
| 7,236,620 B1 | 6/2007 | Gurcan |
| 7,260,250 B2 | 8/2007 | Summers et al. |
| 7,356,367 B2 | 4/2008 | Liang et al. |
| 7,422,563 B2 | 9/2008 | Roshak et al. |
| 7,481,775 B2 | 1/2009 | Weiker et al. |
| 7,483,755 B2 | 1/2009 | Ingle et al. |
| 7,517,320 B2 | 4/2009 | Wibowo et al. |
| 7,815,590 B2 | 10/2010 | Cooper |
| 7,963,925 B1 | 6/2011 | Schecter |
| 7,985,187 B2 | 7/2011 | Wibowo et al. |
| 8,235,908 B2 | 8/2012 | Roshak et al. |
| 8,308,682 B2 | 11/2012 | Kramer et al. |
| 8,337,516 B2 | 12/2012 | Escudero et al. |
| 8,409,167 B2 | 4/2013 | Roshak |
| 8,784,400 B2 | 7/2014 | Roshak |
| 2001/0007940 A1 | 7/2001 | Tu et al. |
| 2001/0021872 A1 | 9/2001 | Bailey et al. |
| 2001/0026666 A1 | 10/2001 | Ferrera et al. |
| 2001/0027339 A1 | 10/2001 | Boatman |
| 2001/0027341 A1 | 10/2001 | Gianotti |
| 2001/0044576 A1 | 11/2001 | Vining |
| 2001/0044650 A1 | 11/2001 | Simso et al. |
| 2001/0047180 A1 | 11/2001 | Grudem et al. |
| 2001/0052344 A1 | 12/2001 | Doshi |
| 2002/0002401 A1 | 1/2002 | McGuckin et al. |
| 2002/0022833 A1 | 2/2002 | Maguire et al. |
| 2002/0028006 A1 | 3/2002 | Novak et al. |
| 2002/0028008 A1 | 3/2002 | Fan et al. |
| 2002/0032477 A1 | 3/2002 | Helmus et al. |
| 2002/0042564 A1 | 4/2002 | Cooper et al. |
| 2002/0042565 A1 | 4/2002 | Cooper et al. |
| 2002/0042622 A1 | 4/2002 | Vargas et al. |
| 2002/0049370 A1 | 4/2002 | Laufer et al. |
| 2002/0055772 A1 | 5/2002 | McGuckin et al. |
| 2002/0071902 A1 | 6/2002 | Ding et al. |
| 2002/0087153 A1 | 7/2002 | Roschak et al. |
| 2002/0091433 A1 | 7/2002 | Ding et al. |
| 2002/0111619 A1 | 8/2002 | Keast et al. |
| 2002/0111620 A1 | 8/2002 | Cooper et al. |
| 2002/0119178 A1 | 8/2002 | Levesque et al. |
| 2002/0123786 A1 | 9/2002 | Gittings et al. |
| 2002/0128647 A1 | 9/2002 | Roschak et al. |
| 2002/0131625 A1 | 9/2002 | Vining et al. |
| 2002/0133057 A1 | 9/2002 | Kukuk |
| 2002/0138074 A1 | 9/2002 | Keast et al. |
| 2002/0147462 A1 | 10/2002 | Mair |
| 2002/0161321 A1 | 10/2002 | Sweezer et al. |
| 2002/0161377 A1 | 10/2002 | Rabkin |
| 2003/0017150 A1 | 1/2003 | Torphy |
| 2003/0070676 A1 | 4/2003 | Cooper et al. |
| 2003/0070682 A1 | 4/2003 | Wilson et al. |
| 2003/0120292 A1 | 6/2003 | Park et al. |
| 2003/0130657 A1 | 7/2003 | Tom et al. |
| 2003/0153971 A1 | 8/2003 | Chandrasekaran |
| 2003/0204138 A1 | 10/2003 | Choi |
| 2003/0216806 A1 | 11/2003 | Togawa et al. |
| 2004/0055606 A1 | 3/2004 | Hendricksen et al. |
| 2004/0060563 A1 | 4/2004 | Rapacki et al. |
| 2004/0073155 A1 | 4/2004 | Laufer et al. |
| 2004/0073201 A1 | 4/2004 | Cooper et al. |
| 2004/0073284 A1 | 4/2004 | Bates et al. |
| 2004/0078054 A1 | 4/2004 | Biggs et al. |
| 2004/0093070 A1 | 5/2004 | Hojeibane et al. |
| 2004/0211434 A1 | 10/2004 | Loomas et al. |
| 2004/0220496 A1 | 11/2004 | Gonzalez |
| 2004/0220556 A1 | 11/2004 | Cooper et al. |
| 2004/0261203 A1 | 12/2004 | Dworzan |
| 2005/0016530 A1 | 1/2005 | McCutcheon et al. |
| 2005/0043751 A1 | 2/2005 | Phan et al. |

(56) References Cited

U.S. PATENT DOCUMENTS

| | | |
|---|---|---|
| 2005/0043752 A1 | 2/2005 | Phan et al. |
| 2005/0049615 A1 | 3/2005 | Cooper et al. |
| 2005/0056292 A1 | 3/2005 | Cooper |
| 2005/0060041 A1 | 3/2005 | Phan et al. |
| 2005/0060042 A1 | 3/2005 | Phan et al. |
| 2005/0060044 A1 | 3/2005 | Roschak et al. |
| 2005/0085801 A1 | 4/2005 | Cooper et al. |
| 2005/0096529 A1 | 5/2005 | Cooper et al. |
| 2005/0107783 A1 | 5/2005 | Tom et al. |
| 2005/0135662 A1 | 6/2005 | Vining et al. |
| 2005/0137518 A1 | 6/2005 | Biggs et al. |
| 2005/0137611 A1 | 6/2005 | Escudero et al. |
| 2005/0137712 A1 | 6/2005 | Biggs et al. |
| 2005/0137715 A1 | 6/2005 | Phan et al. |
| 2005/0147284 A1 | 7/2005 | Vining et al. |
| 2005/0165342 A1 | 7/2005 | Odland |
| 2005/0171527 A1 | 8/2005 | Bhola |
| 2005/0177144 A1 | 8/2005 | Phan et al. |
| 2005/0182295 A1 | 8/2005 | Soper et al. |
| 2005/0182475 A1 | 8/2005 | Jen et al. |
| 2005/0192526 A1 | 9/2005 | Biggs et al. |
| 2005/0228268 A1 | 10/2005 | Cole |
| 2005/0251202 A1 | 11/2005 | Ewers et al. |
| 2005/0261550 A1 | 11/2005 | Akimoto et al. |
| 2005/0288549 A1 | 12/2005 | Mathis |
| 2006/0023966 A1 | 2/2006 | Vining |
| 2006/0116749 A1 | 6/2006 | Willink et al. |
| 2006/0135984 A1 | 6/2006 | Kramer et al. |
| 2006/0142672 A1 | 6/2006 | Keast et al. |
| 2006/0183973 A1 | 8/2006 | Kamrava |
| 2006/0254600 A1 | 11/2006 | Danek et al. |
| 2006/0276807 A1 | 12/2006 | Keast et al. |
| 2006/0280772 A1 | 12/2006 | Roschak et al. |
| 2006/0280773 A1 | 12/2006 | Roschak et al. |
| 2007/0010438 A1 | 1/2007 | Mayo et al. |
| 2007/0016072 A1 | 1/2007 | Grunwald et al. |
| 2007/0092864 A1 | 4/2007 | Reinhardt et al. |
| 2007/0123922 A1 | 5/2007 | Cooper et al. |
| 2007/0250070 A1 | 10/2007 | Nobis et al. |
| 2007/0255304 A1 | 11/2007 | Roschak et al. |
| 2008/0009760 A1 | 1/2008 | Wibowo et al. |
| 2008/0039715 A1 | 2/2008 | Wilson et al. |
| 2008/0086107 A1 | 4/2008 | Roschak |
| 2008/0097139 A1 | 4/2008 | Clerk et al. |
| 2008/0213337 A1 | 9/2008 | Hermansson et al. |
| 2008/0302359 A1 | 12/2008 | Loomas et al. |
| 2008/0312543 A1 | 12/2008 | Laufer et al. |
| 2009/0054805 A1 | 2/2009 | Boyle, Jr. |
| 2009/0076491 A1 | 3/2009 | Roschak et al. |
| 2009/0124883 A1 | 5/2009 | Wibowo et al. |
| 2009/0131765 A1 | 5/2009 | Roschak et al. |
| 2009/0143678 A1 | 6/2009 | Keast et al. |
| 2009/0204005 A1 | 8/2009 | Keast et al. |
| 2009/0275840 A1 | 11/2009 | Roschak et al. |
| 2009/0287087 A1 | 11/2009 | Gwerder et al. |
| 2009/0318904 A9 | 12/2009 | Cooper et al. |
| 2010/0041949 A1 | 2/2010 | Tolkowsky |
| 2010/0268316 A1 | 10/2010 | Brenneman et al. |
| 2010/0305463 A1 | 12/2010 | Macklem et al. |
| 2010/0312141 A1 | 12/2010 | Keast et al. |
| 2011/0082456 A1 | 4/2011 | Welt et al. |
| 2011/0146673 A1 | 6/2011 | Keast et al. |
| 2011/0146674 A1 | 6/2011 | Roschak |
| 2011/0251592 A1 | 10/2011 | Biggs et al. |
| 2011/0306997 A9 | 12/2011 | Roshak et al. |
| 2012/0085346 A9 | 4/2012 | Roshak |
| 2012/0089116 A9 | 4/2012 | Roshak |
| 2012/0123264 A9 | 5/2012 | Keast et al. |
| 2012/0232523 A1 | 9/2012 | Roshak |
| 2012/0289815 A1 | 11/2012 | Keast et al. |
| 2013/0041373 A1 | 2/2013 | Laufer |
| 2013/0046198 A1 | 2/2013 | Roshak et al. |
| 2013/0046296 A1 | 2/2013 | Laufer et al. |
| 2013/0123638 A1 | 5/2013 | Tom et al. |
| 2013/0123826 A1 | 5/2013 | Kramer et al. |

FOREIGN PATENT DOCUMENTS

| | | |
|---|---|---|
| EP | 0443256 A1 | 8/1991 |
| EP | 1151729 A1 | 11/2001 |
| EP | 1400204 A1 | 3/2004 |
| EP | 1436022 A2 | 7/2004 |
| EP | 1485033 A2 | 12/2004 |
| EP | 1485035 A2 | 12/2004 |
| EP | 1509168 A2 | 3/2005 |
| EP | 1648283 A2 | 4/2006 |
| EP | 1648284 A2 | 4/2006 |
| EP | 1786499 A2 | 5/2007 |
| EP | 1802365 A2 | 7/2007 |
| JP | 2001-104315 | 4/1989 |
| JP | 2000-107178 | 4/2000 |
| WO | WO 87/05739 | 9/1987 |
| WO | WO 89/06515 | 7/1989 |
| WO | WO 90/01300 | 2/1990 |
| WO | WO 95/02361 | 1/1995 |
| WO | WO 95/32011 | 11/1995 |
| WO | WO 96/25886 | 8/1996 |
| WO | WO 96/39914 | 12/1996 |
| WO | WO 97/17014 | 5/1997 |
| WO | WO 97/17105 | 5/1997 |
| WO | WO 98/16161 | 4/1998 |
| WO | WO 98/28035 | 7/1998 |
| WO | WO 98/48706 | 11/1998 |
| WO | WO 98/57590 | 12/1998 |
| WO | WO 99/01076 | 1/1999 |
| WO | WO 99/11182 | 3/1999 |
| WO | WO 99/25419 | 5/1999 |
| WO | WO 99/38454 | 8/1999 |
| WO | WO 99/60953 | 12/1999 |
| WO | WO 00/21461 | 4/2000 |
| WO | WO 00/27310 | 5/2000 |
| WO | WO 00/27313 | 5/2000 |
| WO | WO 00/45742 | 8/2000 |
| WO | WO 00/67825 | 11/2000 |
| WO | WO 00/72908 | 12/2000 |
| WO | WO 00/74579 | 12/2000 |
| WO | WO 01/10314 | 2/2001 |
| WO | WO 01/013839 | 3/2001 |
| WO | WO 01/28433 | 4/2001 |
| WO | WO 01/32088 | 5/2001 |
| WO | WO 01/39672 | 6/2001 |
| WO | WO 01/49213 | 7/2001 |
| WO | WO 01/54585 | 8/2001 |
| WO | WO 01/70117 | 9/2001 |
| WO | WO 01/74274 | 10/2001 |
| WO | WO 01/89366 | 11/2001 |
| WO | WO 02/00278 | 1/2002 |
| WO | WO 02/064045 | 8/2002 |
| WO | WO 02/064190 | 8/2002 |
| WO | WO 02/069823 | 9/2002 |
| WO | WO 03/020338 | 3/2003 |
| WO | WO 03/071924 | 9/2003 |
| WO | WO 03/073358 | 9/2003 |
| WO | WO 03/088820 | 10/2003 |
| WO | WO 03/097153 | 11/2003 |
| WO | WO 03/103479 | 12/2003 |
| WO | WO 2005/006963 | 1/2005 |
| WO | WO 2005/006964 | 1/2005 |
| WO | WO 2006/014731 | 2/2006 |
| WO | WO 2006/014732 | 2/2006 |
| WO | WO 2006/130821 | 12/2006 |
| WO | WO 2006/130873 | 12/2006 |
| WO | WO 2007/062406 | 5/2007 |
| WO | WO 2008/063935 | 5/2008 |
| WO | WO 2008/109760 | 9/2008 |

OTHER PUBLICATIONS

Choong, C., et al., "Prolongaton of patency of airway bypass stents with use of drug-eluting stents," *J. Thorac. Cardiovasc. Surg.*, 131: 60-64, 2006.

Cordis Johnson & Johnson Gateway LLC: Bx VELOCITY Stent. Viewed at: http://www.jnjgateway.com/home.jhtm?loc=USENG& page=viewContent&contentId=f c0de00100001015& parentId=fcde00100001015&specialty=Circulatory_Disease_

(56) References Cited

OTHER PUBLICATIONS

Management&category=Cardiac_Diagnosis_Interventions& subcategory=Stents_Balloon_Expandable Viewed on Sep. 5, 2002, 4 pages (please note p. 4 of 4 is blank).

Fessler, H., "Collateral Ventilation, the Bane of Bronchoscopic Volume Reduction," *Am J. Respir Crit. Care Med.* (editorial), 171:423-425, 2005.

Flenley, D., et al., "Factors Affecting Gas Exchange by Collateral Ventilation in the Dog," *Respiration Physiology*, 15:52-69, 1972.

Pulmonary and Critical Care Medicine. Interventional Bronchoscopy with Stent Implant: Stents. Viewed at: http://view.vcu.edu/pulm-ccm/stents.htm Viewed on Aug. 26, 2002. 2 pages.

Rendina, E., et al., "Feasibility and safety of the airway bypass procedure for patients with emphysema," *J. Thorac. Cardiovasc. Surg.*, 125:1294-1299, 2003.

Terry, P., et al., "Collateral Ventilation in Man," *The New England Journal of Medicine*, 298(1):10-15, 1978.

U.S. Appl. No. 13/107,720, filed Nov. 15, 2012 in the name of Keast et al., non-final Office Action mailed Apr. 12, 2013.

U.S. Appl. No. 13/107,720, filed Nov. 15, 2012 in the name of Keast et al., Notice of Allowance mailed Dec. 9, 2013.

Wagner, E., et al., "Direct Assessment of Small Airways Reactivity in Human Subjects," *Am. J. Respir. Crit. Care Med.*, 157:447-452, 1998.

Woolcock, A., et al., "Mechanical Factors Influencing Collateral Ventilation in Human, Dog and Pig Lungs," *Journal of Applied Physiology*, 30(1):99-115. 1971.

Bullae  FIG. 16

METHODS AND DEVICES FOR DIAGNOSING, MONITORING, OR TREATING MEDICAL CONDITIONS THROUGH AN OPENING THROUGH AN AIRWAY WALL

CROSS-REFERENCE TO RELATED APPLICATIONS

This application is a continuation of U.S. patent application Ser. No. 13/107,720, filed on May 13, 2011, the content of which is incorporated herein by reference in its entirety.

FIELD OF THE INVENTION

This application is directed to methods and devices for diagnosing, monitoring, and/or treating medical conditions or tissue through an opening, port or channel through an airway wall.

BACKGROUND

It was found that creation of collateral channels in COPD patients allowed expired air to pass out of the lungs and decompressed hyper-inflated lungs. Such methods and devices for creating and maintaining collateral channels are discussed in U.S. patent application Ser. No. 09/633,651, filed on Aug. 7, 2000, now issued U.S. Pat. No. 6,692,494; U.S. patent application Ser. No. 09/947,144 filed Sep. 4, 2001, now issued U.S. Pat. No. 7,175,644, Ser. No. 09/946,706, filed on Sep. 4, 2001, now issued U.S. Pat. No. 6,749,606, and Ser. No. 09/947,126 filed on Sep. 4, 2014, now issued U.S. Pat. No. 6,712,812; U.S. Provisional Application No. 60/317,338 filed on Sep. 4, 2001; U.S. Provisional Application No. 60/334,642 filed on Nov. 29, 2001; U.S. Provisional Application No. 60/367,436 filed on Mar. 20, 2002; and U.S. Provisional Application No. 60/374,022 filed on Apr. 19, 2002 each of which is incorporated by reference herein in its entirety.

SUMMARY

Various methods and devices for diagnosing, monitoring, and/or treating medical conditions through an extra-anatomic opening, port or channel or other opening through an airway wall are provided.

The creation of collateral channels or extra-anatomic openings may provide convenient access points to the lung parenchyma or other tissue for delivery of substances, tools, or devices to diagnose, monitor, or treat structures, tissue, tumors or diseased tissue that may reside within the lung. The use of such openings allows for diagnosis, monitoring, or treatment in a minimally invasive manner and efficiently delivering needed substances, tools, or devices to the desired area.

In certain variations, a method of accessing target tissue in a lung is provided which includes locating a target site on an airway wall, wherein the target site is in a location that allows for creation of an opening leading to the target tissue and for advancement of an elongate instrument through the opening to the target tissue.

In certain variations, a method of accessing target tissue in a lung may include advancing an elongate instrument to a target site in an airway of the lung; creating an opening through the airway wall at the target site, where the opening leads to the target tissue; and advancing the elongate instrument through the opening to the target tissue.

In certain variations, a method of navigating an elongate instrument through an opening in an airway wall to target tissue in the lung may include advancing an elongate instrument within an airway of the lung; advancing the elongate instrument through an opening in the airway wall; and providing an electromagnetic sensor or electromagnetic field to guide or track the elongate instrument.

In certain variations, a method of accessing target tissue in a lung, may include locating a target site on an airway wall, wherein the target site is in a location that allows for creation of an opening leading to the target tissue and for advancement of an elongate instrument through the opening to the target tissue; and providing an electromagnetic sensor or electromagnetic field to guide or track the elongate instrument.

In certain variations, methods and devices for treating a lung are provided. A method includes treating diseased lung tissue by identifying a region in a lung having the disease lung tissue, selecting a target site at an airway wall, creating an extra-anatomic opening at the target site; and delivering a substance through the extra-anatomic opening to treat the diseased tissue. The diseased tissue may be present beyond the wall of the airway and in the parenchymal tissue of the lung.

In certain variations, a method may or may not include placement of an implant. For example, a substance or device may or may not be delivered through the implant. Moreover, the conduit may be subsequently removed from the airway after the diseased tissue or other tissue is sufficiently treated or accessed. A treatment may treat regions of destroyed tissue and trapped gasses by inducing a collapse of the tissue. Alternatively, or in combination, the treatment may be directed towards tumors or other conditions of the lung.

In certain variations, the methods relating to identifying regions of tissue, selecting a target site, avoidance of blood vessels, and creation of the extra-anatomic opening may rely on the teachings discussed herein that are suited to creation of a collateral opening for releasing trapped gasses.

In certain variations, a substance or device may be delivered using any catheter capable of being deployed in the lungs. Alternatively, or in combination, the substance or devices may be delivered using the devices described below.

In certain variations, methods for identifying the areas of the diseased tissue using the modes described herein or other modes that are suited for the particular medical condition in question are provided. For example, a site for treating a tumor may be located using such means that are well suited for tumor identification.

In certain variations, methods and devices for selecting sites and creating openings are provided. In one variation, a method includes selecting a treatment site in an airway of the lung, creating a hole in an airway wall of the airway; and expanding the hole in the airway wall. Selecting the treatment site may include visual inspection of the site or inspection for the presence or absence of a blood vessel underneath the surface of the airway wall. Selection of the site may be performed or aided by non-invasive imaging. Such imaging may include visual inspection, x-ray, ultrasound, Doppler, acoustic, MRI, PET, and computed tomography (CT) scans. Furthermore, a substance may be administered into the lungs to assist in the selection of the treatment site. For example, the substance may comprise a hyperpolarized gas, a thermochromatic dye, a regular dye, and/or a contrast agent.

In certain variations, the use of a less-traumatic holemaker for creation of the channel (note that a channel includes a hole that is created and subsequently expanded) is provided. The less traumatic holemaker may include a piercing member (e.g., a needle, a cannula, a blade, a tube, a rod or other similar structure). The less traumatic holemaker may also include devices which minimize the collateral damage to tissue (e.g., low temperature RF devices, pulsating RF, low temperature laser, ultrasound, high pressure water, etc.)

In certain variations, devices and methods that prevent closure of the channel such that air may flow through the channel and into the airway are provided. Such channels may be made by a variety of methods as discussed in the patents incorporated by reference above. For example, the channel may be made via a surgical incision, a needle, a rotary coring device, etc. Furthermore, the channel may be made by an energy based device, e.g., RF device, laser, etc. However, it has been noted that use of low temperature devices, e.g., mechanical devices, to create the channel result in less trauma to surrounding tissue and thereby minimize the healing response of the tissue. Accordingly, such modes of creating the channel often result in less occlusion of the channel.

In certain variations, a method may include expanding the hole by inserting a conduit into the hole. Furthermore, the method may comprise partially expanding the hole by deploying the conduit in the hole, and then fully expanding the hole by expanding the conduit within the hole. Preventing closure may be performed using various approaches including, but not limited to, biochemical, electrical, thermal, irradiation, or mechanical approaches (or any combination thereof).

In certain variations, delivering a bio-active composition, as described herein, to maintain patency of the channel or conduit is provided. The bio-active composition may be delivered to the airway wall prior to creation of the channel, subsequent to creation of the channel, and/or after insertion and deployment of the conduit. The bio-active composition may also be delivered through a drug eluting process, either through a composition placed on the conduit, or via delivery of a separate eluting substance. Biochemical approaches include delivery of medicines that inhibit closure of the surgically created channel. The medicines may be delivered locally or systematically. In one variation, a delivery catheter includes a dispense lumen that sends a drug to the target site. Also, bioactive substances may be delivered to the channel tissue using various delivery vehicles such as a conduit. The bioactive substance may be disposed on an exterior surface of the conduit such that it interacts with the channel tissue when the conduit is placed at the injury site. Also, bioactive substances may be delivered to the channel tissue before or after the conduit is positioned in the channel. The bioactive agent may also be delivered to the target site alone. That is, a medicine may be sent to the surgically created channel as the sole mechanism for maintaining the patency of the channel. Also, systematic delivery of medicines may be carried out through digestion, injection, inhalation, etc. Systematic delivery of medicines may be provided alone or in combination with other techniques described herein. For example, a patient having undergone the procedures described herein may be prescribed steroids and/or COX-2 inhibitors in an attempt to prolong the effects of the treatment.

In certain variations, any of the conduits discussed herein may also include at least one visualization feature disposed on a portion of the tissue barrier. The visualization feature may be a stripe circumferentially disposed about at least a portion of the center section. The visualization feature serves to aid in placement or deployment of the conduit in a target site.

In certain variations, a conduit for maintaining the patency of a channel created in tissue comprises a radially expandable center section and extension members as described above. A bioactive substance is disposed on at least a portion of a surface of the conduit. Also, when the conduit is radially expanded it has an overall length and an inner diameter such that a ratio of the overall length to the inner diameter ranges from 1/6 to 2/1. The conduit may also be provided such that this ratio ranges from 1/4 to 1/1 and perhaps, 1/4 to 1/2. A tissue barrier may be disposed on at least a portion of the exterior surface corresponding to the center section. The tissue barrier may be comprised of various materials including but not limited to polymers and elastomers. An example of a material which may be used for the tissue barrier is silicone. Additional matrixes of biodegradable polymer and medicines may be associated with the tissue barrier such that controlled doses of medicines are delivered to the tissue opening.

In certain variations, a hole-making catheter for creating and dilating an opening within tissue is provided. The catheter may include an elongate shaft having a proximal portion and a distal portion, and at least one lumen extending through the proximal end; a balloon having an interior in fluid communication with the lumen, the balloon located on the distal portion of the elongate shaft, the balloon having an uninflated state and an inflated state; a piercing member located at the distal portion of the elongate shaft, the piercing member being extendable and retractable within the elongate shaft; and a depth limiter stop located on the exterior of the distal portion of the elongate shaft, proximal to the balloon and larger in working diameter than the uninflated balloon, which limits the maximum penetration of the catheter into tissue.

The piercing member may include a body portion having a lumen extending therethrough. The lumen of the piercing member may be in fluid communication with a central lumen of the elongate shaft. In some variations, an obturator is used within the device, where the obturator is slidably located within the lumen of the elongate body and piercing member.

The elongate body and/or piercing member may have multiple lumens. For example, they may be constructed from multi-lumen tubing. In some variations, the piercing member is retractable within the elongate shaft.

The balloon member may consist of a distensible balloon or a non-distensible balloon. For either type of balloon, the working diameter may closely match the outer diameter of the piercing member.

In certain variations, an implant located about the balloon of the device is provided. In use, the piercing member would create a channel within the tissue, the device is then further advanced until the implant is located within the channel. Inflation of the balloon then deploys the implant within the channel thereby improving the patency of the channel. Implants include, but are not limited to, a stent, conduit, grommet, valve, graft, anchor, etc.

In certain variations, the device may access airways deep within the lung. The elongate shaft may be comprised of a flexible material. In particular, the elongate shaft may be sufficiently flexible to pass through a fully articulated bronchoscope.

In certain variations, a piercing member may also be used to deliver bio-active agents to the site of the collateral channel. As described herein, such agents may increase the duration of patency of the channels and/or implants.

In certain variations, a balloon catheter for deploying a device within an opening in tissue is provided. The balloon catheter may include an elongate shaft having a proximal portion, a distal portion, a proximal end, a distal end; and at least one lumen extending through the proximal end, a balloon having an interior in fluid communication with the lumen, the balloon located on the distal end portion of the elongate shaft, a guide member extending distally from the distal end of the elongate shaft, the guide member comprising a rounded surface at an end opposite to the elongate shaft, where the guide member has sufficient column strength to penetrate the opening in tissue, the guide member further comprising at least one resistance surface a such that when the body enters the opening, the resistance surface exerts resistance against tissue upon removal of the guide member from the opening. The resistance surface may have an increased diameter greater to provide resistance upon removal from tissue. It may alternatively, or in combination, comprise a rough surface to provide added friction upon removal of the device. The guide member may be tapered, rounded, partially-spherical, elliptical, prolate, cone-shaped, triangular, or any similar shape. It is contemplated that there may be more than one resistance surface on the guide body. Moreover, the guide body may have a wavy/variable diameter shape providing several resistance surfaces on the areas of increased diameter. The device may also be used with an implant that may be located about the balloon where upon expansion of the balloon, the implant deploys. The implant may be selected from a stent, conduit, grommet, valve, graft, and anchor.

In another variation, the balloon catheter may further comprise a dilating member located distally of the balloon. The dilating member may be is located on the distal portion of the shaft between the distal end and the balloon and may comprise a tapered section, a second balloon, or other similar structure. In some variations, the dilating member may be retractable within the elongate shaft. The device may also include a needle assembly moveably located in the instrument lumen, where the needle assembly is advanceable through a hole-making lumen and out of the opening in the rounded surface.

In certain variations, the balloon catheter may be constructed to be sufficient flexibility to advance through a fully articulated bronchoscope. The balloon catheter may also be configured to deliver bio-active substances (e.g., drugs, medicines, compounds, etc.) to the tissue, either via the elongate tube or the guide member. Furthermore, the device may be adapted to provide suction to clear the target site.

In certain variations, a hole-making catheter for creating and dilating an opening within tissue is provided. The catheter may include; an elongate shaft having a proximal portion and a distal portion, and at least one lumen extending through the proximal end; a nondistensible balloon having an interior in fluid communication with the lumen, the nondistensible balloon located on the distal portion of the elongate shaft; and a piercing member located at the distal portion of the elongate shaft, the piercing member being extendable and retractable within the elongate shaft.

In certain variations, an implant delivery system for deploying the implant within a wall of tissue is provided. The system may include; an elongate shaft having a distal portion, a proximal end, a distal end, at least one lumen extending through the proximal end; a balloon member having an interior in fluid communication with the lumen, the balloon member located on the distal portion of the elongate shaft; a piercing member distally located to the distal end of the elongate shaft within the second lumen, the solid piercing member having a sharpened distal end adapted to penetrate tissue; and an expandable implant located about the balloon member.

The preceding illustrations are examples of variation of the devices and methods described therein. It is contemplated that, where possible, combinations of features/aspects of specific embodiments or combinations of the specific embodiments themselves are within the scope of this disclosure.

This application is also related to the following applications 60/420,440 filed Oct. 21, 2002; 60/387,163 filed Jun. 7, 2002; Ser. No. 10/235,240 filed Sep. 4, 2002; Ser. No. 09/947,144 filed Sep. 4, 2001, now issued U.S. Pat. No. 7,175,644; Ser. No. 09/908,177 filed Jul. 18, 2001, now abandoned; Ser. No. 09/633,651 filed Aug. 7, 2000, now issued U.S. Pat. No. 6,692,494; and 60/176,141 filed Jan. 14, 2000; Ser. No. 10/080,344 filed Feb. 21, 2002, now issued U.S. Pat. No. 7,422,563; Ser. No. 10/079,605 filed Feb. 21, 2002, now issued U.S. Pat. No. 7,022,088; Ser. No. 10/280,851 filed Oct. 25, 2002, now abandoned; and Ser. No. 10/458,085 filed Jun. 9, 2003, now abandoned; and Ser. No. 11/538,950 filed Oct. 5, 2006, now issued U.S. Pat. No. 8,409,167. Each of which is incorporated by reference herein in their entirety for all purposes. Applications: Ser. No. 10/458,085 filed Jun. 9, 2003, now abandoned; Ser. No. 10/951,962 filed Sep. 28, 2004, now abandoned; and Ser. No. 11/335,263 filed Jan. 18, 2006, now issued U.S. Pat. No. 8,308,682 are also incorporated by reference herein in their entirety for all purposes.

DETAILED DESCRIPTION

Various methods and devices for diagnosing, monitoring, and/or treating medical conditions through an extra-anatomic opening, port or channel or other opening through an airway wall are described herein.

In certain variations, devices (and methods) for accessing or treating various tissues, e.g., lung tissue, parenchyma or diseased lung tissue, are described herein. In certain variations, methods and devices are described that serve to make or maintain collateral openings or channels through an airway wall so that air is able to pass directly out of the lung tissue and into the airways or so that substances or devices may be delivered to target tissue or lung tissue or parenchymal tissue beyond the airways but within the lungs.

In certain variations, a channel, opening, extra-anatomic opening or port is meant to include, but not be limited to, any opening, hole, slit, channel or passage created in the tissue wall (e.g., airway wall). A channel may be created in tissue having a discrete wall thickness and the channel may extend all the way through the wall. Also, a channel may extend through lung tissue which does not have well defined boundaries such as, for example, parenchymal tissue.

In certain variations, openings or channels may be maintained by preventing or inhibiting tissue from growing into or otherwise blocking the opening or channel. Chemical, electrical, light, mechanical, or a combination of any two or more of these approaches may be performed to maintain the channel openings. For example, the channel walls may be treated with a bioactive agent which inhibits tissue growth. The bioactive agent may be delivered locally or systematically. Also, the channels may be treated with radiofrequency energy, heat, electrical energy, or radiation to inhibit tissue overgrowth. These treatments may be performed once, periodically, or in response to the severity of the channel blockage. For example, the tissue blockage may be periodically removed with a laser or another tissue-removal tool. Also, mechanical devices and instruments may be deployed in the channel to prevent tissue growth from blocking the channel. Mechanical devices include without limitation conduits, valves, sponges, etc. These mechanical devices may be deployed permanently or temporarily. If deployed temporarily, the devices are preferably left in the channel for a sufficient amount of time such that the channel tissue heals coaxially around the device if the medical practitioner intends to create a permanent opening in the airway wall.

Figures 1A, 1B:
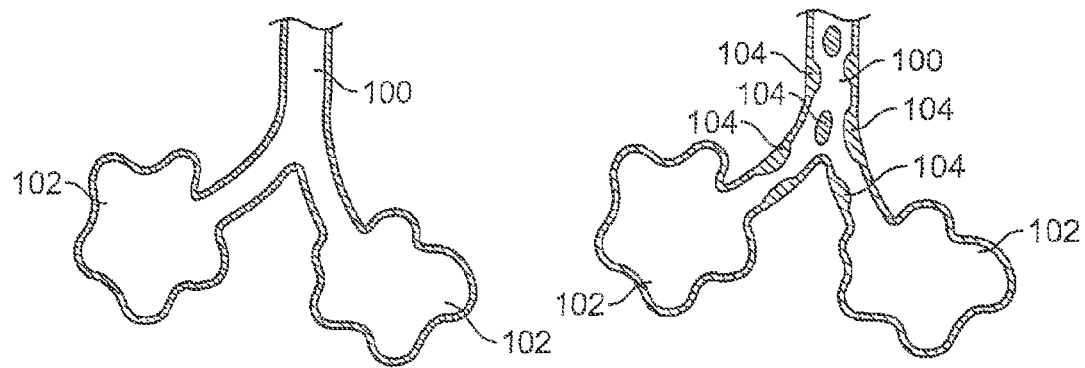
FIGS. 1A-1C illustrate various states of the natural airways and the blood-gas interface.
Figure 1C:
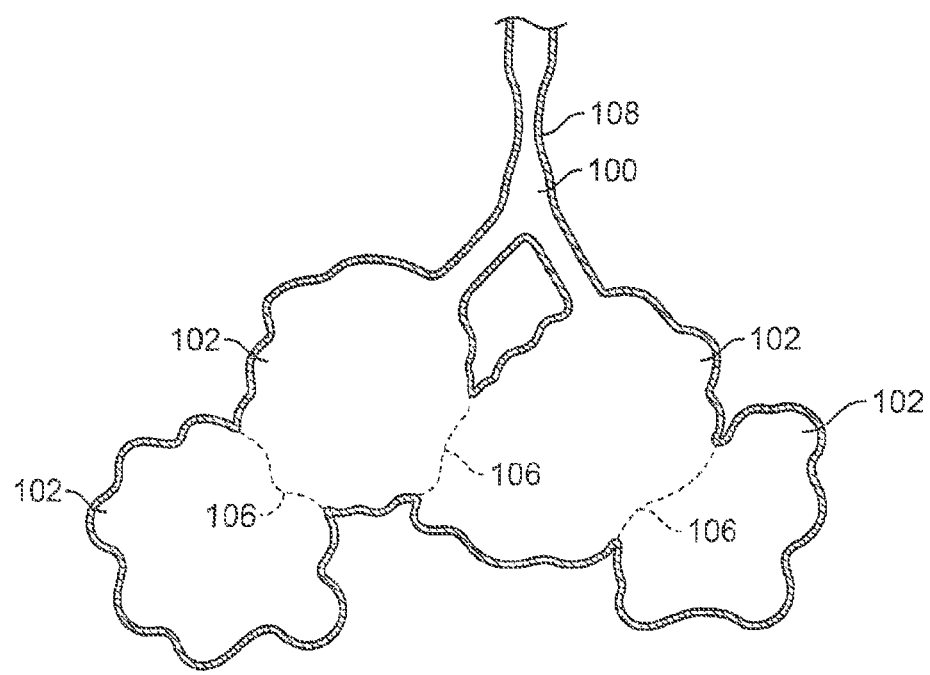

FIGS. 1A-1C are simplified illustrations of various states of a natural airway and a blood gas interface found at a distal end of those airways. FIG. 1A shows a natural airway 100 which eventually branches to a blood gas interface 102.

Although not shown, the airway comprises an internal layer of epithelial pseudostratified columnar or cuboidal cells. Mucous secreting goblet cells are also found in this layer and cilia may be present on the free surface of the epithelial lining of the upper respiratory airways. Supporting the epithelium is a loose fibrous, glandular, vascular lamina propria including mobile fibroblasts. Deep in this connective tissue layer is supportive cartilage for the bronchi and smooth muscle for the bronchi and bronchioles.

FIG. 1B illustrates an airway 100 and blood gas interface 102 in an individual having COPD. The obstructions 104 impair the passage of gas between the airways 100 and the interface 102. FIG. 1C illustrates a portion of an emphysematous lung where the blood gas interface 102 expands due to the loss of the interface walls 106 which have deteriorated due to a bio-chemical breakdown of the walls 106. Also depicted is a constriction 108 of the airway 100. It is generally understood that there is usually a combination of the phenomena depicted in FIGS. 1A-1C. Often, the states of the lung depicted in FIGS. 1B and 1C may be found in the same lung.

Figure 1D:
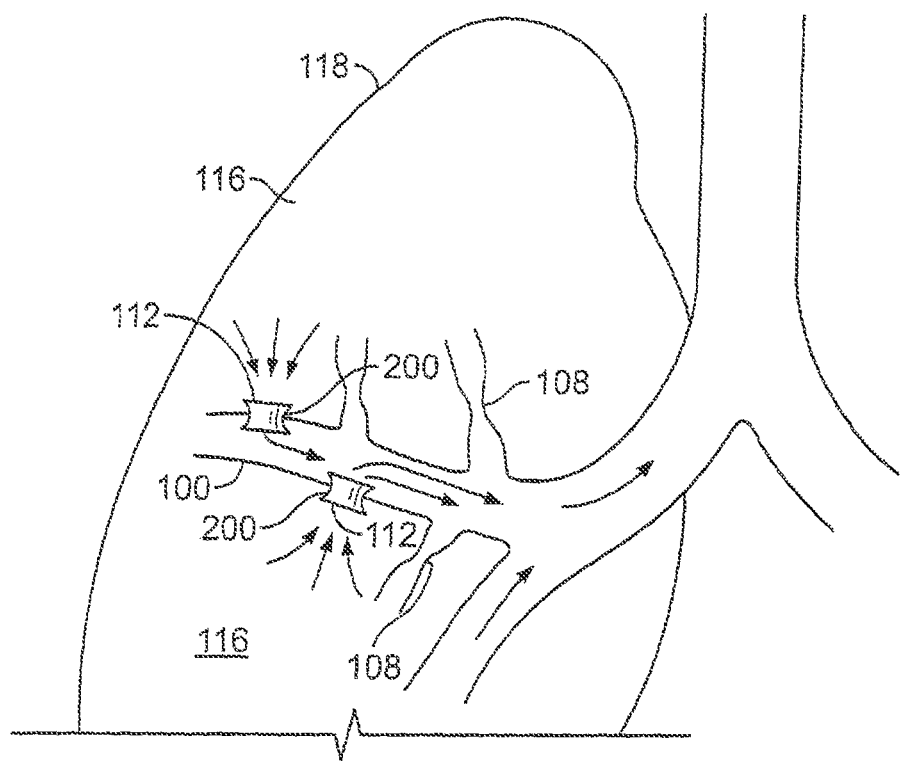
FIG. 1D illustrates a schematic of a lung demonstrating a principle of the inventions described herein.

FIG. 1D illustrates airflow in a lung 118 when conduits 200 are placed in collateral channels 112. As shown, collateral channels 112 (located in an airway wall) place lung tissue 116 in fluid communication with airways 100 allowing air to pass directly out of the airways 100 whereas constricted airways 108 may ordinarily prevent air from exiting the lung tissue 116. While the invention is not limited to the number of collateral channels which may be created, it is to be understood that 1 or 2 channels may be placed per lobe of the lung and perhaps, 2-12 channels per individual patient. However, as stated above, the invention includes the creation of any number of collateral channels in the lung. This number may vary on a case by case basis. For instance, in some cases in an emphysematous lung, it may be desirable to place 3 or more collateral channels in one or more lobes of the lung.

Although FIG. 1D depicts a mechanical approach to maintaining channels in the airway walls, the channel openings may be maintained using a variety of approaches or combinations of approaches.

As shown in FIGS. 2A-2G, the conduits described herein in certain variations, generally include a center section 208 and at least one extension member (or finger) 202 extending from each end of the center section. The extension members, as will be discussed in more detail below, are capable of deflecting or outwardly bending to secure the conduit in an opening created in an airway wall thereby maintaining the patency of the opening. The extension members may deflect such that opposing extension members may form a V, U or other type of shape when viewed from the side.

Additionally, the conduits shown in FIGS. 2A-2G include a center-control segment 235, 256 which restricts or limits radial expansion of the center section. The center-control segments are adapted to straighten as the center section is radially expanded. Once the center-control segments become straight or nearly straight, radial expansion of the conduit is prevented. In this manner, the radial expansion of the conduit may be self controlled.

It is understood that the conduits discussed herein are not limited to those shown in the figures. Instead, conduits of various configurations may be used as described herein. Such conduits are described in the following U.S. patent application Ser. No. 09/908,177 filed Jul. 18, 2001, now abandoned; International Application No. PCT/US03/12323 filed Apr. 21, 2003; U.S. patent application Ser. No. 09/947,144 filed Sep. 4, 2001, now issued U.S. Pat. No. 7,175,644; U.S. patent application Ser. No. 10/235,240 filed Sep. 4, 2002, now abandoned; and U.S. patent application Ser. No. 10/458,085 filed Jun. 9, 2003, now abandoned, the entirety of each of which is hereby incorporated by reference.

Conduit States

The conduits described herein may have various states (configurations or profiles) including but not limited to (1.) an undeployed state and (2.) a deployed state.

Figure 2A:
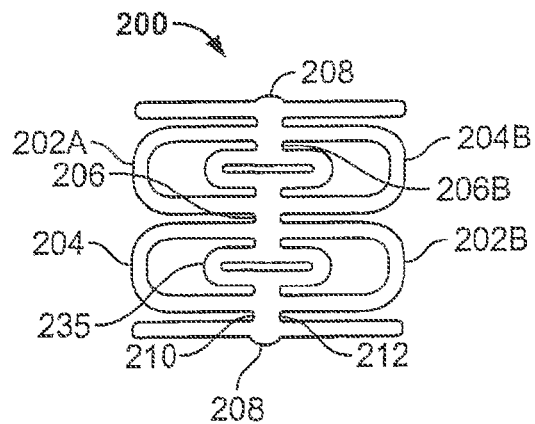
FIG. 2A illustrates a side view of a conduit in an undeployed state.

The undeployed state is the configuration of the conduit when it is not secured in an opening in an airway wall and, in particular, when its extension members (or fingers) are not outwardly deflected to engage the airway wall. FIG. 2A is a side view of a conduit 200 in an undeployed state. As shown in this figure, extension members 202A, 202B extend straight from the ends 210, 212 respectively of center section 208. The extension members shown in this example are parallel. However, the invention is not so limited and the extension members need not be parallel.

Figure 2B:
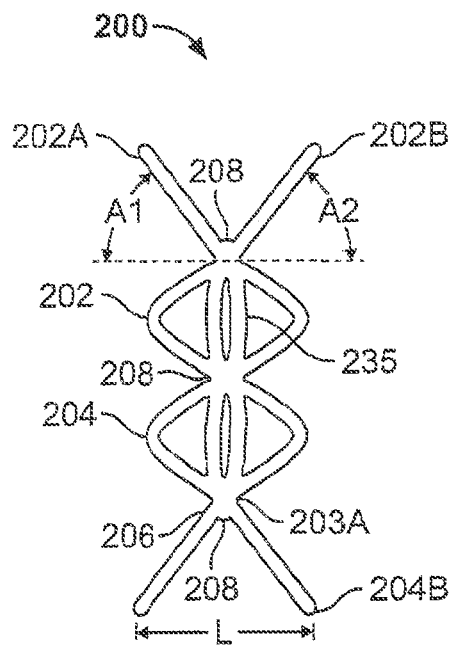
FIG. 2B illustrates a side view of the conduit of FIG. 2A shown in a deployed shape.
Figure 2D:
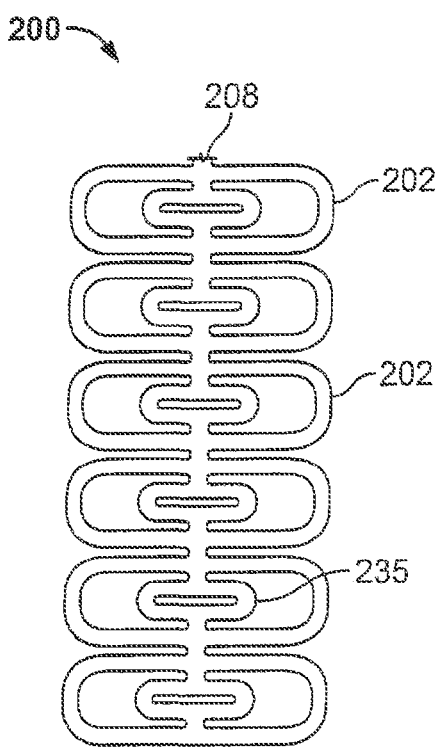
FIG. 2D is a cylindrical projection of the undeployed conduit shown in FIG. 2A.
Figure 2C:
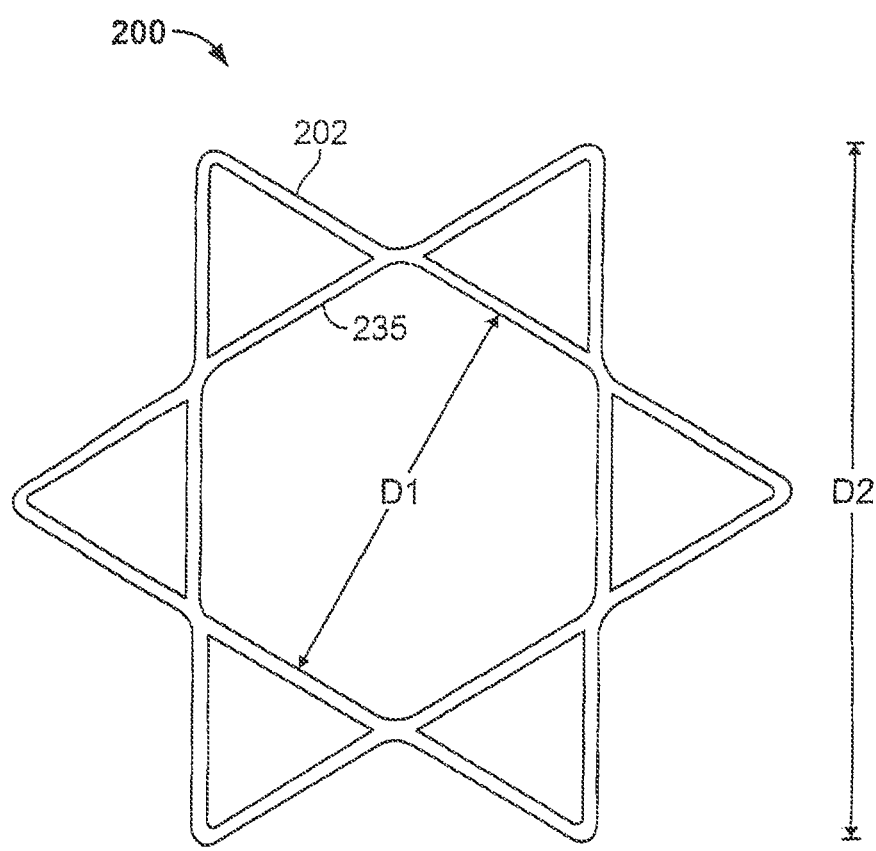
FIG. 2C illustrates a front view of the conduit shown in FIG. 2B.

The deployed state is the configuration of the conduit when it is secured in a channel created in an airway wall and, in particular, when its extension members are outwardly bent to engage the airway wall such that the conduit is fixed in the opening. An example of a conduit in its deployed configuration is shown in FIGS. 2B and 2C. FIG. 2B is a side view of a conduit in its deployed state and FIG. 2C shows a front view of the conduit of FIG. 2B.

Center Section of the Conduit

As shown in FIGS. 2A-2D, the conduit includes a center section 208 having a short passageway. This center section may be a tubular-shaped open-frame (or mesh) structure having a plurality of ribs. Also, as explained in more detail below, the center section may be a sheet of material.

The axial length of the center section or passageway may be relatively short. In FIGS. 2A-2D, the passageway's length is about equal to the width of a wire segment or rib. Here, the center section serves as a bridge or junction for the extension members and it is not required to be long. The axial length of the passageway may therefore be less than 1 mm and even approach 0 mm. In one example, the length of the center section is less than twice the square root of a cross sectional area of the center section. However, the center section may also have passageways which have lengths greater than 1 mm.

The overall length (L) of the conduit may be distinguished from the length of the center section because the overall length includes the lengths of the extension members. Further, the overall length (L) is dependent on which state the conduit is in. The overall length of the conduit will typically be shorter when it is in a deployed state as shown in FIG. 2B than when it is in an undeployed state as shown in FIG. 2A. The overall length (L) for a deployed conduit may be less than 6 mm and perhaps, between 1 and 20 mm.

FIG. 2C shows a front view of the conduit 200 shown in FIG. 2B. FIG. 2C shows the passageway having a hexagonal (or circular) cross section. The cross-section, however, is not so limited. The cross section may be circular, oval, rectangular, elliptical, or any other multi-faceted or curved shape. The inner diameter ($D_1$) of the center section, when deployed, may range from 1 to 10 mm and perhaps, from 2 to 5 mm. Moreover, in some variations, the cross-sectional area of the passageway, when deployed, may be between 0.2 $mm^2$ to 300 $mm^2$ and perhaps between 3 $mm^2$ and 20 $mm^2$ The diameter of the center section, when deployed, thus may be significantly larger than the passageway's axial length (e.g., a 3 mm diameter and an axial length of less than 1 mm). This ratio of the center section length to diameter (D1) may range from about 0:10 to 10:1, 0.1:6 to 2:1 and perhaps from 1:2 to 1:1.

The diameter of the center section, when deployed, may also be nearly equal to the overall length (L) of the conduit 200. This overall length (L) to diameter (D1) ratio may range from 1:10 to 10:1, 1:6 to 2:1, and perhaps from 1:4 to 1:1. However, the invention is not limited to any particular dimensions or ratio unless so indicated in the appended claims. Rather, the conduit should have a center section such that it can maintain the patency of a collateral channel in an airway wall. The dimensions of the center section (and the conduit as a whole) may be chosen based on the tissue dimensions. When the channel is long in its axial length, for example, the length of the center section may likewise be long or identical to the channel's length.

Extension Members of the Conduit

As mentioned above, extending from the ends of the center section 208 are extension members 202A, 202B which, when the conduit is deployed, form angles A1, A2 with a central axis of the passageway. When viewed from the side such as in FIG. 2B, opposing extension members may have a V, U, or other shape. The extension members 202A, 202B may thus outwardly rotate until they sandwich tissue (not shown) between opposing extension members.

The angles A1, A2 may vary and may range from, for example, 30 to 150 degrees, 45 to 135 degrees and perhaps from 30 to 90 degrees. Opposing extension members may thus form angles A1 and A2 of less than 90 degrees when the conduit is deployed in a channel. For example, angles A1 and A2 may range from 30 to 60 degrees when the conduit is deployed.

The conduits of the present invention are effective and may maintain a surgically created opening despite not substantially sandwiching tissue between opposing extension members as described above. Additionally, it is not necessary for the conduits of the present invention to prevent air from flowing along the exterior of the conduit. That is, air may move into (and through) spaces between the exterior of the conduit and the interior wall of the tissue channel. Thus, fluidly sealing the edges of the conduit to prevent side flow or leakage around the conduit is not crucial for the conduits to be effective. However, the conduits of the present invention are not so limited and may reduce or eliminate side flow by, for example, increasing the angles A1 and A2 and adding sealant around the exterior of the conduit.

Moreover, the angle A1 may be different than angle A2. Accordingly, the conduit may include proximal extension members which are parallel (or not parallel) to the distal extension members. Additionally, the angle corresponding to each proximal extension member may be different or identical to that of another proximal extension member. Likewise, the angle corresponding to each distal extension member may be different or identical to that of another distal extension member.

The extension members may have a length between 1 and 20 mm and perhaps, between 2 and 6 mm. Also, with reference to FIG. 2C, the outer diameter ($D_2$) of a circle formed by the free ends of the extension members may range from 2 to 20 and perhaps, 3 to 10 mm. However, the invention is not limited to the dimensions disclosed above. Furthermore, the length of the distal extension members may be different than the length of the proximal extension members. The length of the distal extension members may be, for example, longer than that of the proximal extension members. Also, the lengths of each proximal extension member may be different or identical to that of the other proximal extension members. Likewise, the lengths of each distal extension member may be different or identical to that of the other distal extension members.

The number of extension members on each end of the center section may also vary. The number of extension members on each end may range from 2-10 and perhaps, 3-6. Also, the number of proximal extension members may differ from the number of distal extension members for a particular conduit. Moreover, the extension members may be symmetrical or non-symmetrical about the center section. The proximal and distal extension members may also be arranged in an in-line pattern or an alternating pattern. The extension members or the center section may also contain barbs or other similar configurations to increase adhesion between the conduit and the tissue. The extension members may also have openings to permit tissue ingrowth for improved retention.

The shape of the extension members may also vary. They may be open-framed and somewhat petal-shaped as shown in FIGS. 2A-2D. In these figures, the extension members 202A, 202B comprise wire segments or ribs that define openings or spaces between the members. However, the invention is not so limited and the extension members may have other shapes. The extension members may, for example, be solid or they may be filled.

In another variation the conduit is constructed to have a delivery state. The delivery state is the configuration of the conduit when it is being delivered through a working channel of a bronchoscope, endoscope, airway or other delivery tool. The maximum outer diameter of the conduit in its delivery state must therefore be such that it may fit within the delivery tool, instrument, or airway.

In one variation, the conduit is radially expandable such that it may be delivered in a smaller working channel of a scope while maximizing the diameter to which the conduit may expand upon deployment. For example, sizing a conduit for insertion into a bronchoscope having a 2 mm or larger working channel may be desirable. Upon deployment, the conduit may be expanded to have an increased internal diameter (e.g., 3 mm.) However, the invention is not limited to such dimensions. It is contemplated that the conduits 200 may have center sections that are expanded into a larger profile from a reduced profile, or, the center sections may be restrained in a reduced profile, and upon release of the restraint, return to an expanded profile.

Additionally, the conduit need not have a smaller delivery state. In variations where the center section is not able to assume a second smaller delivery profile, a maximum diameter of the first or deployed profile will be sufficiently small such that the conduit may be placed and advanced within an airway or a working channel of a bronchoscope or endoscope. Also, in cases where the conduit is self-expanding, the deployed shape may be identical to the shape of the conduit when the conduit is at rest or when it is completely unrestrained.

Additionally the conduit may be partially expanded in its proximal region in the delivery state, as shown in figure X. The partially expanded portion would still me sized small enough to fit within the working channel of the bronchoscope, but would be significantly larger (e.g., 0.5-2 mm) larger that the distal portion of the conduit. This partial expansion allows for easy placement of the conduit by providing a physical stop for the conduit within the airway wall. After the conduit is placed the entire conduit can be expanded to its intended expanded shape.

The partial expansion state can also be achieved by partially inflating the proximal section of the conduit with a separate balloon on the delivery device. Another possible method is to design the conduit to preferentially expand the proximal section before the distal section, thereby partially expanding the conduit to create the size differential, placing the stent inside the airway wall with the aid of the stop, and then fully expanding the conduit.

Control Members

The conduit 200 shown in FIGS. 2A-2D also includes diametric-control segments, tethers, or leashes 235 to control and limit the expansion of the center section 208 when deployed. This center-control segment 235 typically is shaped such that when the conduit radially expands, the center-control segment bends until it is substantially straight or no longer slack. Such a center-control segment 235 may be circular or annular shaped. However, its shape may vary widely and it may have, for example, an arcuate, semi-circular, V, or other type of shape which limits the expansion of the conduit.

Typically, one end of the center-control segment is attached or joined to the center section at one location (e.g., a first rib) and the other end of the center-control segment is connected to the center section at a second location (e.g., a rib adjacent or opposite to the first rib). However, the center-control segments may have other constructs. For example, the center-control segments may connect adjacent or non-adjacent center section members. Further, each center-control segment may connect one or more ribs together. The center-control segments may further be doubled up or reinforced with ancillary control segments to provide added control over the expansion of the center section. The ancillary control segments may be different or identical to the primary control segments.

FIG. 2B illustrates the conduit 200 in its deployed configuration. As discussed above, the center-control segments 235 may bend or otherwise deform until they maximize their length (i.e., become substantially straight) such as the center-control segments 235 shown in FIG. 2B. However, as discussed above, the invention is not so limited and other types of center-control segments may be employed.

Figure 2E:
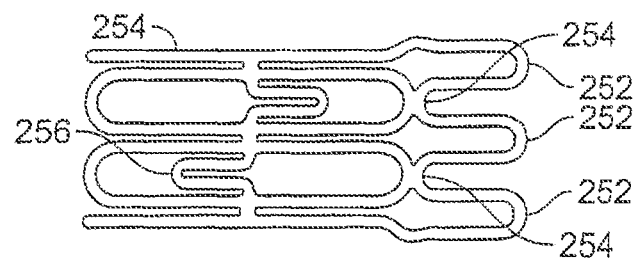
FIG. 2E illustrates a side view of another variation of a conduit in an undeployed shape.
Figure 2F:
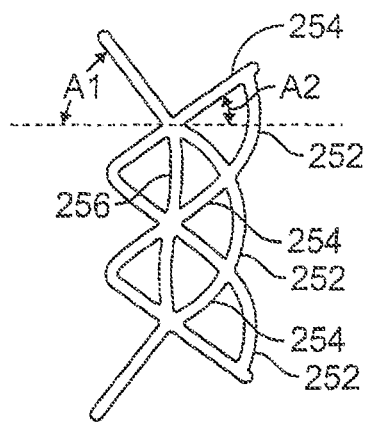
FIG. 2F illustrates a side view of the conduit of FIG. 2E in a deployed state.
Figure 2G:
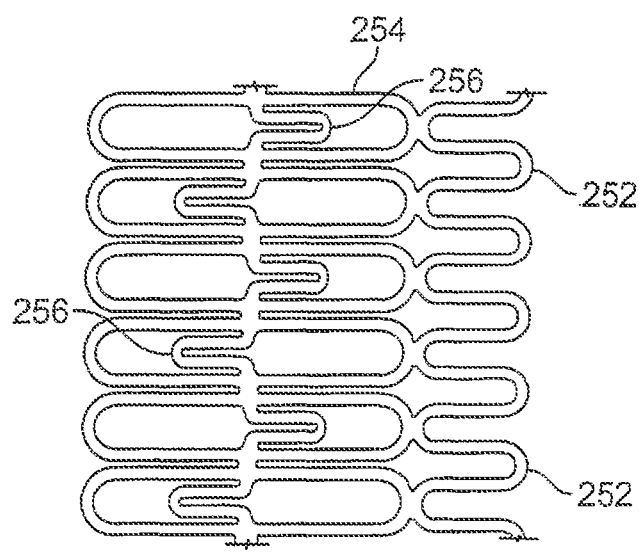
FIG. 2G is a cylindrical projection of the undeployed conduit shown in FIG. 2E.

As shown in FIGS. 2E-2G, control segments 252 may also be used to join and limit the expansion of the extension members 254 or the control segments may be placed elsewhere on the conduit to limit movement of certain features to a maximum dimension. By controlling the length of the control segments, the shape of the deployed conduit may be controlled. In the conduit shown in FIGS. 2E-2G, the conduit includes both center-control segments 256 and distal control segments 252. The center-control segments are arcuate shaped and join adjacent rib sections of the center section and the distal-control segments are arcuate and join adjacent distal extension members.

FIG. 2F illustrates the conduit in a deployed configuration and shows the various control members straightening as the extension members and center section deploy. The proximal extension members, however, are not restricted by a control member and consequently may be deflected to a greater degree than the distal extension members. Accordingly, a conduit having control members connecting, for example, regions of the center section and having additional control segments connecting extension members, may precisely limit the maximum profile of a conduit when it is deployed. This is desirable where overexpansion of the conduit is hazardous.

This also serves to control the deployed shape of the conduit by, for instance, forcing angle A1 to differ from angle A2. Using control segments in this manner can provide for cone-shaped conduits if the various types of control-segments have different lengths. For example, providing longer proximal-control segments than distal-control segments can make angle A1 larger than angle A2. Additionally, cylindrical-shaped conduits may be provided if the center-control segments and the extension-control segments are sized similarly such that angle A1 equals angle A2. Again, the control segments straighten as the conduit expands and the conduit is thus prevented from expanding past a predetermined amount.

The control segments, as with other components of the conduit, may be added or mounted to the center section or alternatively, they may be integral with the center section. That is, the control segments may be part of the conduit rather than separately joined to the conduit with adhesives or welding, for example. The control segments may also be mounted exteriorly or interiorly to the members to be linked. Additionally, sections of the conduit may be removed to allow areas of the conduit to deform more readily. These weakened areas provide another approach to control the final shape of the deployed conduit. Details for creating and utilizing weakened sections to control the final shape of the deployed conduit may be found in U.S. patent application Ser. No. 09/947,144 filed on Sep. 4, 2001, now issued U.S. Pat. No. 7,175,644.

Manufacture and Materials

The conduit described herein may be manufactured by a variety of manufacturing processes including but not limited to laser cutting, chemical etching, punching, stamping, etc. For example, the conduit may be formed from a tube that is slit to form extension members and a center section between the members. One variation of the conduit may be constructed from a metal tube, such as stainless steel, 316L stainless steel, titanium, titanium alloy, nitinol, MP35N (a nickel-cobalt-chromium-molybdenum alloy), etc. Also, the conduit may be formed from a rigid or elastomeric material that is formable into the configurations described herein. Also, the conduit may be formed from a cylinder with the passageway being formed through the conduit. The conduit may also be formed from a sheet of material in which a specific pattern is cut. The cut sheet may then be rolled and formed into a tube. The materials used for the conduit can be those described above as well as a polymeric material, a biostable or implantable material, a material with rigid properties, a material with elastomeric properties, or a combination thereof. If the conduit is a polymeric elastic tube (e.g. a thermoplastic elastomer), the conduit may be extruded and cut to size, injection molded, or otherwise formed.

Additionally, the conduits described herein may be comprised of a shape memory alloy, a super-elastic alloy (e.g., a NiTi alloy), a shape memory polymer, or a shape memory composite material. The conduit may be constructed to have a natural self-assuming deployed configuration, but is restrained in a pre-deployed configuration. As such, removal of the restraints (e.g., a sheath) causes the conduit to assume the deployed configuration. A conduit of this type could be, but is not limited to being, comprised from an elastic polymeric material, or shape memory material such as a shape memory alloy. It is also contemplated that the conduit could comprise a shape memory alloy such that, upon reaching a particular temperature (e.g., 98.5° F.), it assumes a deployed configuration.

Also, the conduit described herein may be formed of a plastically deformable material such that the conduit is expanded and plastically deforms into a deployed configuration. The conduit may be expanded into its expanded state by a variety of devices such as, for example, a balloon catheter.

The conduit's surface may be modified to affect tissue growth or adhesion. For example, an implant may comprise a smooth surface finish in the range of 0.1 micrometer to 0.01 micrometer. Such a finish may serve to prevent the conduit from being ejected or occluded by tissue overgrowth. On the other hand, the surface may be roughened or porous. The conduit may also comprise various coatings and tissue barriers as discussed below.

Tissue Barrier

Figure 3A:
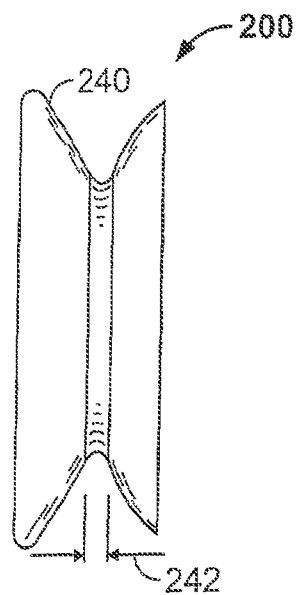
FIG. 3A illustrates a side view of a conduit having a tissue barrier in a deployed state.

FIG. 3A illustrates another variation of a conduit 200 having a tissue barrier 240. The tissue barrier 240 prevents tissue ingrowth from occluding the collateral channel or passage of the conduit 200. The tissue barrier 240 may coaxially cover the center section from one end to the other or it may only cover one or more regions of the conduit 200. The tissue barrier may completely or partially cover the conduit so long as the ends are at least partially open. Moreover, the tissue barrier may only be placed on the center section of the conduit. The tissue barrier 240 may be located about an exterior of the conduit's surface, about an interior of the conduit's surface, or the tissue barrier 240 may be located within openings in the wall of the conduit's surface. Furthermore, in some variations of the invention, the center section 208 itself may provide an effective barrier to tissue ingrowth. The tissue barrier, of course, should not cover or block the entrance and exit of the passageway such that air is prevented from passing through the conduit's passageway. However, in some constructs, the tissue barrier may partially block the entrance or exit of the passageway so long as air may continue to pass through the conduit's passageway.

The tissue barrier may be formed from a material, mesh, sleeve, or coating that is a polymer or an elastomer such as, for example, silicone, fluorosilicone, polyurethane, PET, PTFE, or expanded PTFE. Other biocompatible materials will work, such as a thin foil of metal, etc. The coatings may be applied, for example, by either dip coating, molding, spin-coating, transfer molding or liquid injection molding. Alternatively, the tissue barrier may be a tube of a material and the tube is placed either over and/or within the conduit. The tissue barrier may then be bonded, crimped, heated, melted, shrink fitted or fused to the conduit. The tissue barrier may also be tied to the conduit with a filament of, for example, a suture material.

Still other techniques for attaching the tissue barrier include: solvent swelling applications and extrusion processes; wrapping a sheet of material about the conduit, or placing a tube of the material about the conduit and securing the tube to the conduit. The tissue barrier may be secured on the interior of the conduit by positioning a sheet or tube of material on the inside of the center section and securing the material therein.

The tissue barrier may also be formed of a fine mesh with a porosity or treatment such that tissue may not penetrate the pores. For example, a ChronoFlex™ DACRON® or TEFLON® mesh having a pore size of 100-300 microns may be saturated with collagen or another biocompatible substance. This construct may form a suitable tissue barrier. The mesh may be coaxially attached to a frame such as the open frame structures disclosed above. Still other suitable frames include a continuous spiral metallic or polymeric element. Given the mesh's radial strength or lack thereof, the use of a reinforcement element serves to prevent the implant from collapsing. Also, as described below, other substances may be applied to the exterior surface of the conduit to control elution of various medicines.

Figure 3B:
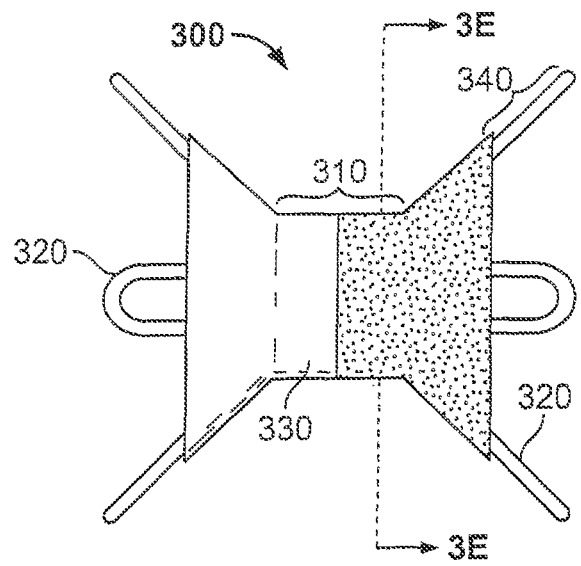
FIG. 3B illustrates a side view of a conduit having a tissue barrier.
Figure 3C:
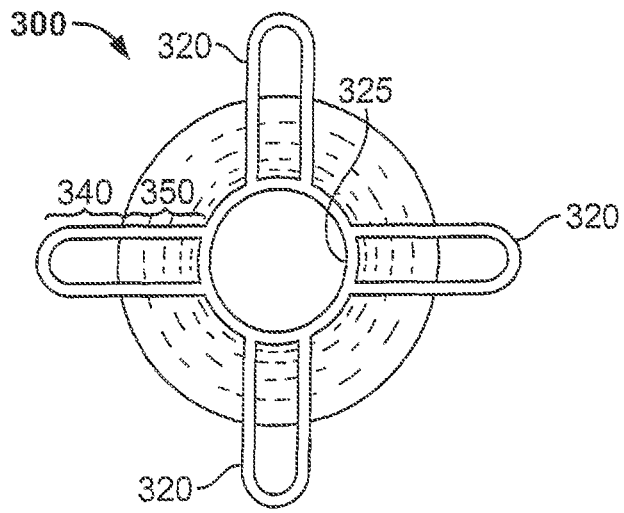
FIG. 3C is a front view of the conduit shown in FIG. 3B.

FIGS. 3B and 3C respectively illustrate a side view and a front view of another conduit 300 having a partial tissue barrier coating. The conduit 300 includes a center section 310, a plurality of extension members 320, and a partial tissue barrier 330. The conduit 300 is thus different than that shown in FIG. 3A in that the center section is longer and that the tissue barrier 330 only partially covers the extension members 320. In particular, the center section 310 shown in FIGS. 3B-3C is cylindrical or tubular-shaped. This shape may be advantageous when a relatively long passageway is desired. Also, it is to be understood that the overall (or three dimensional) shape of the center section, when deployed, is not limited to the shape shown here. Rather, it may have various shapes such as, for example, rectangular, tubular, conical, hour-glass, hemi-toroidal, etc.

Additionally, the tissue barrier 330 covers only a first region 350 of the extension members and leaves a second region 340 of the extension members uncovered. The second or free region 340 of the extension members 320 is shown as being open-framed. However, the invention is not so limited. The second region of the extension members may be solid and it may include indentations, grooves, and recesses for tissue ingrowth. Also, the extension members may include small holes for tissue ingrowth. For example, the second region of the extension members may have a dense array of small holes. In any event, the conduits described herein may include at least one region or surface which is susceptible to tissue ingrowth or is otherwise adherent to the tissue. Accordingly, tissue ingrowth at the second region 340 of the extension members is facilitated while tissue growth into the passageway 325 is thwarted.

Figure 3D:
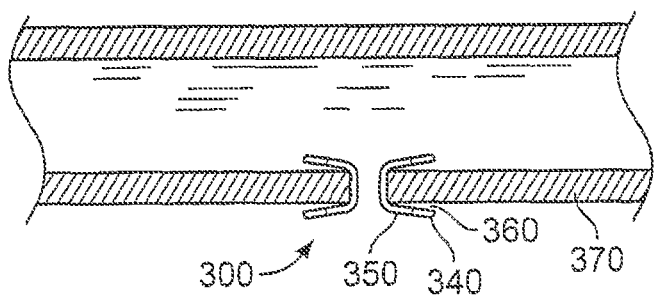
FIG. 3D illustrates a conduit positioned in a channel created in a tissue wall.
Figure 3E:
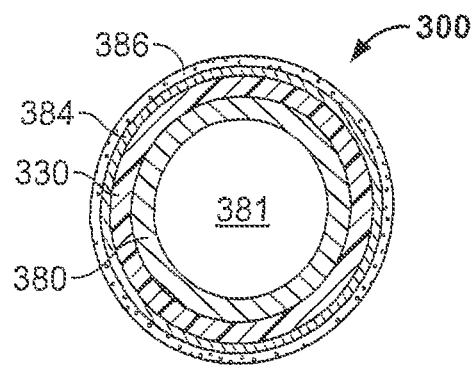
FIG. 3E is a cross sectional view of the conduit shown in FIG. 3B taken along line 3E-3E.
Figure 3F:
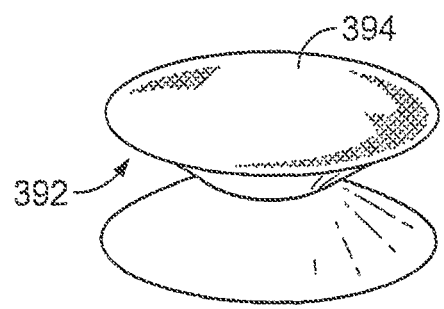
FIGS. 3F-3G depict another conduit including a membrane that supports a bioactive substance; the bioactive substance may be coated on the membrane.
Figure 3G:
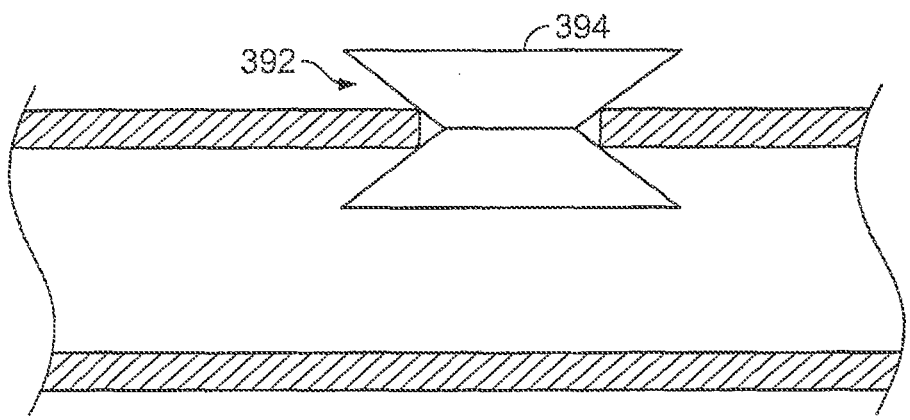

As shown in FIG. 3D, tissue growth 360 into the uncovered region 340 further secures the extension members to the tissue wall 370. Free region 340 of the extension members may also include tissue growth substances such as epithelial growth factors or agents to encourage tissue ingrowth. Accordingly, conduit 300 may be configured to engage the tissue wall 370 as well as to allow tissue to grow into predetermined regions of the conduit.

Visualization Feature

The conduit shown in FIG. 3A also includes a visualization ring or marker 242. The marker 242 is visually apparent during a procedure. The marker is observed as the conduit is placed in a collateral channel and, when the marker is even with the opening of the channel, the conduit may be deployed. In this manner, the visualization feature facilitates alignment and deployment of the conduits into collateral channels.

The visualization ring or mark may be a biocompatible polymer and have a color such as white. Also, the visualization feature may protrude from the center section or it may be an indentation(s). The visualization mark may also be a ring, groove or any other physical feature on the conduit. Moreover, the visualization feature may be continuous or comprise discrete segments (e.g., dots or line segments).

The visualization feature may be made using a number of techniques. In one example, the mark is a ring formed of silicone and is white. The polymeric ring may be spun onto the tissue barrier. For example, a clear silicone barrier may be coated onto the conduit such that it coaxially covers the extension members and the center section as shown in FIG. 3A. Next, a thin ring of white material such as a metal oxide suspended in clear silicone may be spun onto the silicone coating. Finally, another coating of clear silicone may be applied to coat the white layer. The conduit thus may include upwards of 1-3 layers including a tissue barrier, a visualization mark layer, and a clear outer covering.

The shape of the visualization mark is not limited to a thin ring. The visualization mark may be large, for example, and cover an entire half of the conduit as shown in FIG. 3B. The visualization mark may, for example, be a white coating disposed on the proximal or distal half of the conduit. The visualization mark thus may extend from an end of the extension members to the center section of the conduit. As explained in more detail below, when such a device is deposited into a channel created in lung tissue, the physician may observe when one-half of the conduit extends into the channel. This allows the physician to properly actuate or deploy the conduit to secure the conduit in the tissue wall.

Accordingly, the visualization member is made visually apparent for use with, for example, an endoscope. The visualization feature, however, may also be made of other vision-enhancing materials such as radio-opaque metals used in x-ray detection. It is also contemplated that other elements of the conduit can include visualization features such as but not limited to the extension members, tissue barrier, control segments, etc.

In some variations of the invention, it was found that incorporation of a bioactive, as discussed herein, or other substance into the coating caused a coloration effect in the composition layer (e.g., the polymer turns white). This coloration obscures the support member structure in the layer making it difficult to identify the edges and center of the support member or implant. As discussed herein, placement of the implant may depend upon positioning the center of the implant within the opening in tissue. If the support member structure is identifiable, then one is able to visually identify the center of the implant. When the composition colors obscures the support member or renders the implant otherwise opaque, it may become difficult to properly place the device. This may be especially true when the composition layer extends continuously over the support member.

Additionally, the coloration may render the visualization mark difficult to identify especially under direct visualization (e.g., using a scope). In some cases it was undesirable to simply add additional substances on or in the composition layer for marking because such substances could possibly interfere with the implant's ability to deliver the substance as desired. To address these issues, a variation of the invention includes a delivery device for delivering an expandable implant (such as those described herein and in the cases referenced herein), where the delivery device includes an expandable member having an expandable implant located about the expandable member. Where the implant and the expandable member are of different visually identifiable colors or shades such that they distinction is easy to identify under endoscopic or bronchoscopic viewing.

In one example, as shown in FIG. 9C, a balloon catheter has a colored sleeve 306 located about the balloon. The sleeve 306 comprises a visually identifiable color where selection of the colors should ease identification of the implant an endoscopic visualization system (e.g., blue or a similar color that is not naturally occurring within the body.) The implant is placed about the sleeve 306 where the proximal and distal areas of the implant would be identifiable by the difference in color. Such a system allows a medical practitioner to place the implant 200 properly by using the boundary of the implant 200 to guide placement in the tissue wall. The sleeve 306 may be fashioned from any expandable material, such as a polymer. Optionally, the sleeve 306 may also provide an elastic force to return the balloon to a reduced profile after expansion of the balloon. Such a system allows for identification without affecting the properties of the implant.

It should be noted that variations of the invention include coloring the balloon itself, or other expandable member, a color that meets the above criteria.

In another variation, the visualization mark may comprise providing a contrast between the implant and a delivery catheter. In one example the implant is appears mostly white and while mounted on a contrasting color inflation balloon. In this example the implant would be placed over a blue deflated balloon catheter. The proximal and distal areas of the implant would be flanked by the deflated blue balloon, thus giving the appearance of a distinct distal and proximal end of the implant. This would allow a physician to place the implant properly by using the blue flanks as a guide for placing the central white portion in the tissue wall. Similarly, a colored flexible sheath covering the balloon would also suffice.

It is noted that while the visualization features described above are suitable for use with the implants described herein, the inventive features are not limited as such. The features may be incorporated into any system where placement of an implant under direct visualization requires clear identification of the implant regardless of whether the implant is opaque or colored.

Bioactive Agents

As discussed above, the bio-active substance or combination of bioactive substances is selected to assists in modifying the healing response as a result of the trauma to the lung tissue resulting from creation of the collateral channel. As noted above, the term lung tissue is intended to include the tissue lining the airway, the tissue beneath the lining, and the tissue within the lung but exterior to the airway (e.g., lung parenchyma.) The purpose of modifying the healing response is to further extend the patency of the channel or implant to increase the duration which trapped gasses may exit through the implant into the airways. The term antiproliferative agent is intended to include those bioactive substances that directly modify the healing response described herein.

The bioactive substances are intended to interact with the tissue of the surgically created channels and in particular, lung tissue. These substances may interact with the tissue in a number of ways. They may, for example, 1.) accelerate cell proliferation or wound healing to epithelialize or scar the walls of the surgically-created channel to maintain its patent shape or 2.) the substances may inhibit or halt tissue growth when a channel is surgically created through an airway wall such that occlusion of the channel due to tissue overgrowth is prevented. Additionally, other bioactive agents may inhibit wound healing such that the injury site (e.g., the channel or opening) does not heal leaving the injury site open and/or inhibit infection (e.g., reduce bacteria) such that excessive wound healing does not occur which may lead to excessive tissue growth at the channel thereby blocking the passageway.

A variety of bioactive substances may be used alone or in combination with the devices described herein. Examples of bioactive substances include, but are not limited to, antimetabolites, antithrobotics, anticoagulants, antiplatelet agents, thorombolytics, antiproliferatives, antinflammatories, agents that inhibit hyperplasia and in particular restenosis, smooth muscle cell inhibitors, growth factors, growth factor inhibitors, cell adhesion inhibitors, cell adhesion promoters and drugs that may enhance the formation of healthy neointimal tissue, including endothelial cell regeneration. The positive action may come from inhibiting particular cells (e.g., smooth muscle cells) or tissue formation (e.g., fibromuscular tissue) while encouraging different cell migration (e.g., endothelium, epithelium) and tissue formation (neointimal tissue).

Still other bioactive agents include but are not limited to analgesics, anticonvulsives, anti-infectives (e.g., antibiotics, antimicrobials), antineoplastics, H2 antagonists (Histamine 2 antagonists), steroids, non-steroidal anti-inflammatories, hormones, immunomodulators, mast cell stabilizers, nucleoside analogues, respiratory agents, antihypertensives, antihistamines, ACE inhibitors, cell growth factors, nerve growth factors, anti-angiogenic agents or angiogenesis inhibitors (e.g., endostatins or angiostatins), tissue irritants (e.g., a compound comprising talc), poisons (e.g., arsenic), cytotoxic agents (e.g., a compound that can cause cell death), various metals (silver, aluminum, zinc, platinum, arsenic, etc.), epithelial growth factors or a combination of any of the agents disclosed herein.

Examples of agents include pyrolitic carbon, titanium-nitride-oxide, taxanes, fibrinogen, collagen, thrombin, phosphorylcholine, heparin, rapamycin, radioactive 188Re and 32P, silver nitrate, dactinomycin, sirolimus, everolimus, Abt-578, tacrolimus, camptothecin, etoposide, vincristine, mitomycin, fluorouracil, or cell adhesion peptides. Taxanes include, for example, paclitaxel, 10-deacetyltaxol, 7-epi-10-deacetyltaxol, 7-xylosyl-10-deacetyltaxol, 7-epi-taxol, cephalomannine, baccatin III, baccatin V, 10-deacetylbaccatin III, 7-epi-10-deacetylbaccatin III, docetaxel.

Of course, bioactive materials having other functions can also be successfully delivered in accordance with the variations described herein. For example, an antiproliferative agent such as methotrexate will inhibit over-proliferation of smooth muscle cells and thus inhibit restenosis. The antiproliferative is desirably supplied for this purpose until the tissue has properly healed. Additionally, localized delivery of an antiproliferative agent is also useful for the treatment of a variety of malignant conditions characterized by highly vascular growth. In such cases, an implant such as a implant could be placed in the surgically created channel to provide a means of delivering a relatively high dose of the antiproliferative agent directly to the target area. A vasodilator such as a calcium channel blocker or a nitrate may also be delivered to the target site. The agent may further be a curative, a pre-operative debulker reducing the size of the growth, or a palliative which eases the symptoms of the disease. For example, tamoxifen citrate, Taxol® or derivatives thereof Proscar®, Hytrin®, or Eulexin® may be applied to the target site as described herein.

Variations of the invention may also include fibrinolytics such as tPA, streptokinase, or urokinase, etc. Such fibrinolytics prevent or reduce the accumulation of fibrin within the opening. Accumulation of fibrin in the opening may result from inflammation of the tissue. The fibrin may form a structure which makes it easier for tissue to grow into the opening using the fibrin structure as a framework. Use of fibrinolytics, either topically, locally, or on the implant, serves to remove or hinder the network of fibrin from forming within the opening (or implant) and therefore aids in modifying the healing response.

In the event that poisonous and toxic compounds are delivered, they should be controlled so that inadvertent death of tissue does not occur. The poisonous agent should be delivered locally or only be effective locally. One method for delivering the bioactive agent locally is to associate the bioactive agent with an implant. For example, the implants described herein may include a bioactive substance or medicine deposited onto the interior, the exterior, or both the interior and exterior surfaces of the implant. The bioactive substance may remain on the implant so that it does not leach. Cells that grow into the surgically created channel contact the poison and die. Alternatively, the bioactive agent may be configured to gradually elute as discussed below.

When used in the lungs, the implant modifies the healing response of the lung tissue (e.g., at the site of newly created hole/channel) for a sufficient time until the healing response of the lung tissue subsides or reduces such that the hole/channel becomes a persistent air path. For example, the implant and bioactive substance will modify the healing response for a sufficient time until the healing response is reduced and, from a visual observation, the body treats the opening essentially as a natural airway passage rather than as an injury to the airway wall.

In one variation of the invention which modifies the healing response as describe above, the implant provides a steady release rate of bio-active substance as well as has a sufficient amount of available bio-active substance to modify the healing response of the lung tissue. As noted herein, the term lung tissue is intended to include the tissue lining the airway, the tissue beneath the lining, and the tissue within the lung but exterior to the airway (e.g., lung parenchyma.) Such a delivery profile allows for a concentration gradient of drug to build in these tissues adjacent to the delivery site of the implant.

It is believed that forming the concentration gradient affects the healing response of the lung tissue so that the implant does not become occluded as a result of the healing response. Because the implant is often placed in the airway wall it is exposed to the healing process of the multiple tissues. Providing a sufficient amount of bio-active substance allows for the formation of a concentration of the bio-active substance across these various tissues. In one variation of the invention it is believed that the fluids from these tissues enter into the composition layer of the device. The fluids then combine with the bio-active substances and migrate out of the composition layer to settle into the lung tissue. A concentration gradient forms when the drug 'saturates' local tissue and migrates beyond the saturated tissues. Furthermore, by providing a sufficient delivery rate, the healing response may be affected or suppressed during the critical time immediately after the wounding caused by creation of the collateral channel when the healing response is greatest.

To select a proper combination of drug and polymer, it is believed that the solubility parameter of the polymer must be matched with the bio-active substance to provide an acceptable slow elution rate from the polymer. Next, the polymer itself must be selected to have the proper attributes, such as a proper diffusion coefficient (to slow fluid entering and departing from the implant), and proper mechanical expansion properties (to allow for the significant expansion of the polymer to accommodate formation of the grommet shape.)

The solubility parameter is defined as the square root of the cohesive energy of the molecules in a compound. The level of control that a polymer has over the elution of a drug is the difference between the solubility parameters of the polymer and the solubility parameter of the drug. To select a polymer with the approximate diffusion a polymer with a high internal density could be selected to be less permeable to a complex molecule such as paclitaxel. Using a polymer with high internal density also accommodated the significant expansion required of the polymer to form the structure necessary to grommet about the airway wall. An example of the polymer selection is found below.

It is also important to note that paclitaxel is a taxane that is regarded as a microtubule stabilizer. The benefits of a microtubule stabilizing substance for use in vascular drug eluting stents is discussed, for example, in U.S. Pat. No. 5,616,608 to Kinsella et al. This type of drug operates to enhance microtubule polymerization which inhibits cell replication by stabilizing microtubules in spindles which block cell division. In contrast to the vascular applications, the implant for use in one variation described herein may use microtubule stabilizing substances such as taxanes (e.g., paclitaxel) as well as those microtubule destabilizing substances that are believed to promote microtubule disassembly in preventing cell replication. Such destabilizing substances include, but are not limited to vincristine, vinblastine, podophylotoxin, estramustine, noscapine, griseofulvin, dicoumarol, a vinca alkaloid, and a combination thereof.

Additionally, the exterior surface of the implant may be treated via etching processes or with electrical charge to encourage binding of the bioactive substances to the implant. The exterior surface may also be roughened to enhance binding of the medicine to the surface as discussed in U.S. Pat. No. 6,918,927. See also U.S. Patent Publication No. 2002/0071902, now abandoned, and U.S. Pat. Nos. 5,824,048 and 6,730,349 which discuss various techniques for coating medical implants.

Although the implant may comprise a frame or body with a bioactive matrix disposed or otherwise associated therewith, the invention is not so limited. In one variation, the support member is formed from a polymer and the composition is joined to the polymeric support member. Alternatively, the bioactive substances may be placed directly onto the polymeric support member.

Various additional substances may be used incorporated into the device to reduce an adverse reaction resulting from possible contact with the implant and the airway wall. Adverse reactions include, but are not limited to, granulation, swelling, and mucus overproduction. These substance may also be inhaled, injected, orally applied, topically applied, or carried by the implant. These substances may include anti-inflammatory, infection-fighting substances, steroids, mucalytics, enzymes, and wound healing-accelerating substances. Examples of these substances include but are not limited to, acetylcysteine, albuterol sulfate, ipratropium bromide, dornase alfa, and corticosteroids.

As noted above, conventional vascular drug eluting devices are not designed for exposure multiple tissue environments. Moreover, those devices are placed in an environment where a constant flow of blood creates an environment requiring a different delivery mechanism and rate. As noted herein, experiments with conventional coronary drug eluting implants demonstrated that such devices were unsuitable.

Channel Creation Devices and Methods

Figure 4A:
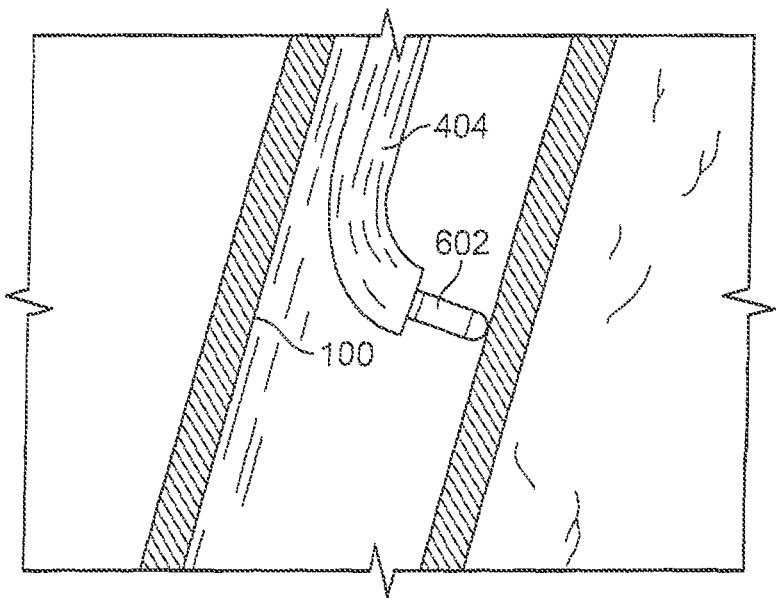
FIGS. 4A-4C a variation of selecting a site, creating a channel at the site using a less traumatic hole-maker, and expanding the channel.
Figure 4B:
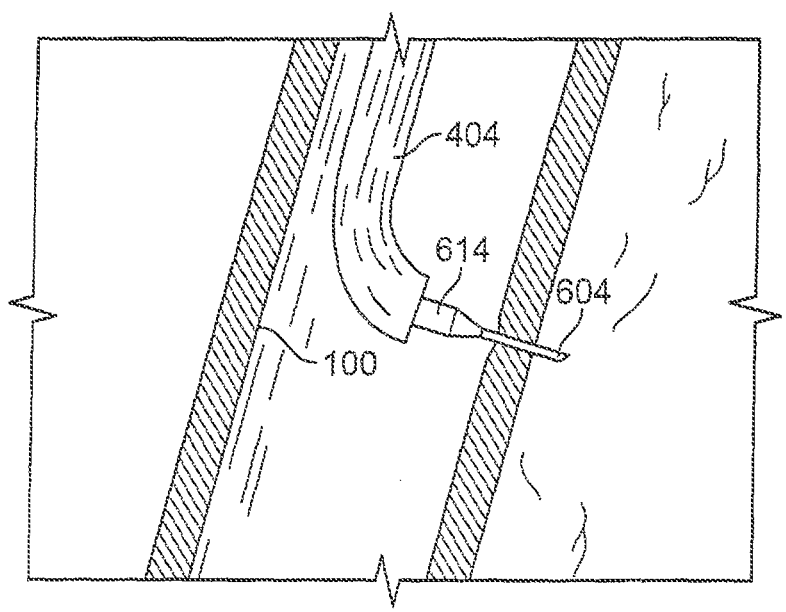
Figure 4C:
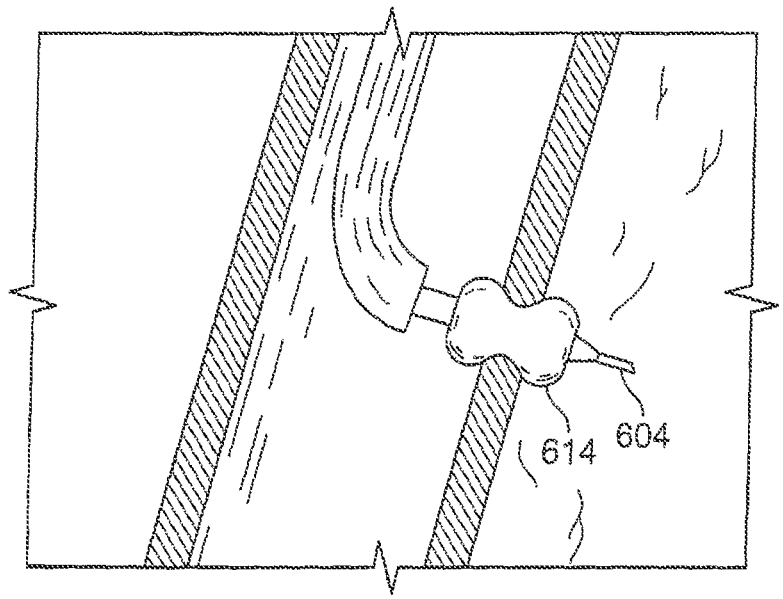

As discussed above, the use of low temperature devices, (e.g., mechanical devices, newer generation RF-type devices, etc.) to create the channel may result in less trauma to surrounding tissue and minimize the healing response of the tissue. FIGS. 4A-4C illustrates creation of the collateral channel and selecting a treatment site in the airway 100. As will be discussed in more detail below, a single device may be used to select the site and create the channel. Moreover, another variation of the invention includes using such a device to deploy the conduit at the target site. However, the one variation also contemplates using separate devices to perform each step or a combination of steps.

As shown in FIG. 4A, a device 602 is advanced, for example, via a bronchoscope 404, into the airway 100. A potential treatment site is then inspected to determine whether or not a blood vessel is in proximity to the site. Naturally, if a blood vessel is detected, the surgeon has the option of selecting a different site. The device 602 may be a Doppler ultrasound device, a thermal device, an imaging device, etc.

FIG. 4B illustrates another variation of selecting a site for a channel. In this variation, a piercing member (e.g., a blade affixed to a shaft, a needle, cannula, sharpened tube or rod, etc.,) 604 is advanced into the airway wall. Once the piercing member 604 is inserted into the airway wall, the surgeon may inspect the area for blood to determine whether the device punctured a blood vessel. After the opening is created the surgeon may also remove collect a biopsy of material behind the airway wall. If the opening is large enough as created by a balloon, as described herein, the surgeon may use forceps to visually obtain the sample. This may be preferable to a blind method of obtaining biopsies, considering that the risk of bleeding may be reduced because the area has been scanned for blood vessels.

The piercing member 604 may have a lumen and may be open at a distal end or closed. In those cases where the piercing member 604 is hollow and has an opening at or near the distal end, the surgeon may aspirate the site using the piercing member 604 to determine whether a blood vessel is present and/or penetrated. For example, flashback catheters contain chambers which will fill with blood upon the penetration of a vessel by the distal tip of the catheter. The piercing member may be incorporated to have a flashback chamber to detect the presence of blood flow from a penetrated vessel. Using these approaches, a target site may not be selected until after a hole is made in the airway 100 wall. It should be noted that a piercing member may be of a diameter which results in closure of the puncture site upon removal of the piercing member. Alternatively, the piercing member may be of a sufficient size or construction that the hole remains open upon removal of the piercing member. In any case, the piercing member or another device may be used to mark the site of the opening (e.g., via ink, dye, physical marker, via application of electrical energy, etc.) Furthermore, another variation includes use of both a detecting device as described above in combination with a piercing member. For example, the site may be inspected by the detecting device prior to insertion of a piercing member.

The piercing member lumen may also used to deliver therapeutic fluids to the lungs. For example, in case of bleeding after channel creation the physician may apply epinephrine or saline the lungs. Alternatively the physician may use the piercing member to apply epinephrine to the airway wall prior to creation of the channel, to prevent bleeding. This may be done by injecting directly into the airway wall at or about the site of passage creation; singly or in a surrounding pattern of multiple applications. The physician may also use the piercing member lumen to apply any of the bioactive agents discussed herein, before or after passage creation.

Because it may be desirable to reach remote airways within the lung, it may be necessary to fully articulate the scope 404 to access and inspect a desirable site. Therefore, to inspect the site and create an opening, it may be desirable to maintain the scope 404 in a fixed position and simply advance/retract various components of the scope or devices in the scope. Accordingly, a piercing member may be selected to have a length that will sufficiently pass through the airway wall, while being small enough that it will also pass through a fully articulated bronchoscope. Furthermore, the piercing member may have sections of varying stiffness where a distal portion, (that is sufficient stiff to penetrate the tissue) may be of a length such that it is able to advance through a fully articulated bronchoscope. For example, the piercing member may comprised of a sharpened cannula which has a length from between 2 mm to 30 mm. The diameter may range between 16 Ga to 25 Ga or larger. The cannula may be affixed to a catheter having a relatively flexible proximal portion. In any case, the length of the piecing member 604 may vary as needed.

The piercing member is not limited to a cannula; it may be of solid construction, such as a sharpened rod or wire. Additionally the piercing member may be adapted with an elongate member, such as a wire, rod, or tube, which extends throughout the device. The purpose of the elongate member is to provide column strength to the piercing member and necessary bending resistance to the catheter, because it has been found that the device must have high column strength to effectively pierce the airway wall, otherwise the device will deflect and not create a passageway. The elongate member may be utilized to expose and retract the piercing member within the catheter, as the elongate member may extend throughout the device to a user interface. The elongate member and piercing member may also be constructed from one piece of material, thereby making them one part. Alternatively the elongate member may be a separate part welded, bonded, mechanically attached, or a combination thereof, to the piercing member.

However, it is understood, that the current invention is not limited to any particular length of the piercing member. Furthermore, the piercing member may be comprised of a resilient polymer, a polymer with a reinforced structure (e.g., a braid, coil, etc.), a super-elastic alloy, a metallic material with sufficient resilience, etc, such that it may navigate through a fully articulated bronchoscope yet return to its original profile upon exiting the working channel of the scope.

In some variations of the invention, the piercing member of the device may be retractable within a lumen of an elongate shaft so as to prevent damage to the bronchoscope or to tissue as the device advances to the target site. Additionally the piercing member may be retracted after the initial piercing of the airway wall, and blunt trauma may be used to further push the remaining portion of the catheter into the airway wall. This technique may help avoid additional bleeding and pneumothoraxes from an exposed piercing member. The catheter may be advanced to tortuous locations; therefore the device may incorporate low friction materials to make it easier to reach the treatment site. The materials may be selected from a group of low friction polymers, for example PTFE. Low friction materials may also be applied as a coating onto the pierced member or elongate member, for example PTFE or titanium nitride. Reducing the contact surface area between the members may also help to reduce friction. Adding or removing material from the surfaces of members is one way to reduce contact surface area. For example attaching a closed coiled spring around the piercing member or elongate member, effectively reduces the surface area contacted between the elongate member and lumen because only the peaks of the coils contact the lumen.

In additional variations of the invention, as shown in FIG. 4C, a balloon catheter may be configured with a piercing member 604. In this variation the balloon 614 advances into the opening created by the piercing member (in which case the piercing member either retracts into the catheter or advances with the catheter.) The balloon 614 would then deploy to dilate the opening for ease of later inserting a conduit. Alternatively, a conduit may be located on the balloon itself and deployed on inflation of the balloon. Examples of variations of such a balloon catheter may be found below. Furthermore, the needle may be affixed to a tapered introducer type device which is able to dilate the opening.

The piercing member 604 may also be used to deliver bioactive substances (as described herein) to the site of the opening. In such a case, the piercing member 604 may deliver the bioactive substance during creation of the opening (e.g., see FIG. 4B) or after dilation of the opening (see e.g., FIG. 4C). In another variation of the invention, the piercing member 604 may be have a multi-lumen cross-section with different lumens being reserved, for example, for inflating the balloon, aspirating the site for blood, drug delivery, and suction of mucous/fluids at the site. In any of the variations described herein, an obturator (not shown) may be used to fill a lumen during advancement of the piercing member into tissue so that the lumen does not become blocked with tissue or other debris. The obturator may be a guide-wire, polymeric column of material, etc.

Figure 4D:
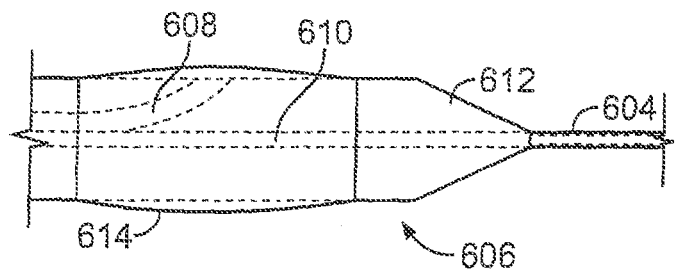
FIGS. 4D-4K illustrate variations of piercing members for creating collateral channels.

FIG. 4D illustrates a variation of a balloon catheter 606 having a piercing member 604. In this variation, the balloon catheter 606 comprises two lumens 608, 610. One lumen 608 is fluidly coupled to the interior of the balloon 614 while the second lumen 610 extends through the piercing member 604. It is understood that the device 606 may be configured to have any number of lumens as required. As discussed above, the piercing member 604 may either be fixedly attached to the distal end of the balloon catheter 606. Alternatively, the piercing member 604 may be retractable into the balloon catheter 606 so that it does not cause damage to lung parenchyma when the catheter 606 is inserted into the airway 100 wall. As illustrated, the balloon catheter 606 may have a tapered section 612 between the piercing member 604 and the balloon 614 to assist in insertion of the balloon 614 into the opening 112.

Figure 4E:
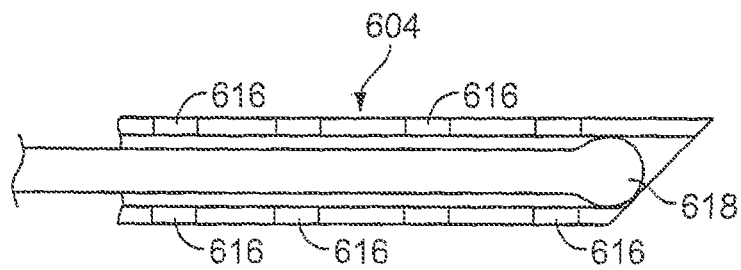

FIG. 4E illustrates an additional variation of a piercing member 604. As illustrated, the piercing member 604 may have a number of ports 616 (e.g., openings, holes, etc.). The ports 616 may allow for either aspiration of blood or delivery of bio-active substances as described herein. Furthermore, although the piercing members 604 shown herein are configured with a beveled tip, it is contemplated that the tip may be any type of tip sufficient to penetrate the airway wall. For instance, the tip may be non-beveled with sharpened edges, the tip may be a trocar tipped needle, or any other available needle tip configuration. The piercing member 604 of FIG. 4E is also shown with an obturator placed therein. In this configuration, the obturator 618 blocks the lumen of the piercing member 604 at the distal end. Moreover, as shown, a portion of the obturator 618 may be sized such that it is smaller than a lumen of the piercing member 604 to allow for delivery of substances or aspiration through the ports 616.

Figure 4F:
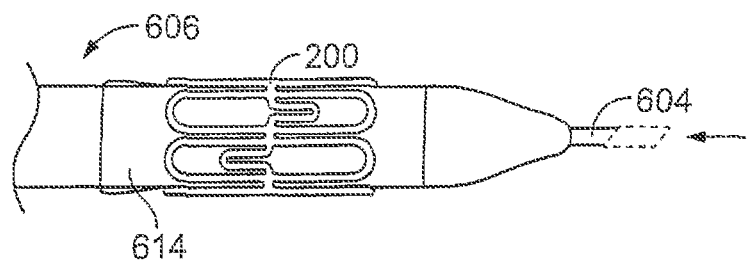

FIG. 4F illustrates yet another variation of a balloon catheter 606 having a piercing member 604. In this variation, as indicated by the arrow, the piercing member 604 is capable of being retracted into the catheter 606. The ability to retract the piercing member 604 into the catheter 606 reduces the possibility of the piercing member 604 causing damage to any lung tissue that is behind the airway wall. Clearly, this variation combines the channel-making step with the conduit deployment step. Also, as shown in the figure, the catheter 606 may have a conduit 202 placed over the balloon 614. Such a variation may create the opening or channel and then deploy the conduit 200 with a single device.

Figure 4G:
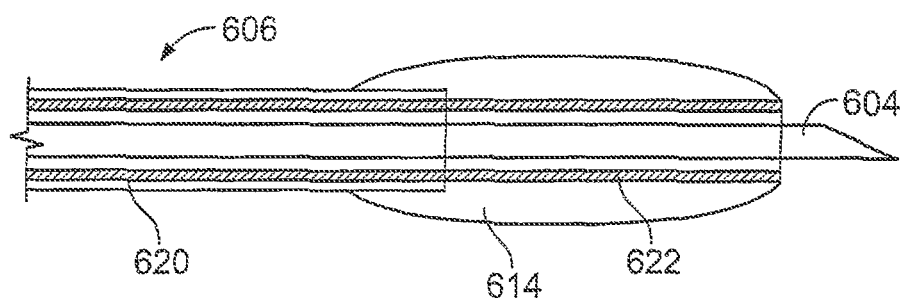

FIG. 4G illustrates another variation of a balloon catheter 606 where the piercing member 604 is slidably located within the catheter 606. In this variation, the catheter 606 contains an outer and inner sheaths 620, 622 which define two lumens. The lumen defined by the inner sheath 622 extends to the distal end of the catheter 606 and may be used to deliver bioactive substances, for suction, or for irrigation.

It is also contemplated that variations of the invention include a piercing member which is affixed to the catheter. Alternatively, the piercing member could have a flexible body that extends through the catheter to a proximal hub which is able to be coupled to a vacuum source, a source of medication, etc. Furthermore, either the piercing member and/or balloon catheter may be "pre-loaded" with a bioactive substance. Such a feature allows improves the precision of amount of substance delivered to the desired site.

Figure 4H:
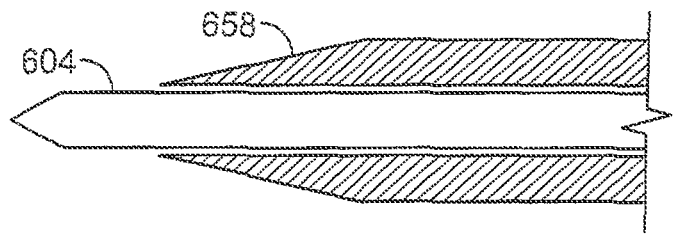

As mentioned above, the piercing member 604 may be of a sufficient size or construction that the hole remains open upon removal of the piercing member. Once variation of this as shown in FIG. 4H, where the device has a conical tip 658 with a lumen extending through out. A piercing member 604 is extendable past the distal tip to pierce the airway wall, after the initial opening is made, the rest of the device can be driven into the airway wall, gradually expanding the hole to a desirable diameter which allows the conduit to be subsequently placed.

The makeup of airway tissue may require a considerable amount of force to create a channel with the piercing device. Therefore, it will generally be easier to create a channel if the device has sufficient column strength to avoid bending of the device when applying a force at the proximal end of the device.

Additional variations of the invention may incorporate a nondistensible balloon to overcome the toughness of the airway tissue. Nondistensible balloons are generally made up of relatively inelastic materials consisting of PET, nylons, polyurethanes, polyolefins, PVC, and other crosslinked polymers. The makeup of airway tissue may be very tough and resist radial expansions. Therefore it will be generally easier to expand the channel in the airway wall using high pressure nondistensible balloons (>6 atm), which generally inflate in a uniform shape.

Nondistensible balloons will occupy a greater mass than distensible balloons because they in an inelastic predetermined form. Too much balloon mass will have too large of a working diameter, which in turn will hinder entry into a channel. Working diameter is the smallest effective diameter opening the uninflated nondistensible balloon can be inserted into. Therefore it is desirable to have the uninflated nondistensible balloon to have a working diameter close to the diameter of the piercing device 604. This can be attained by using a thin walled balloon, using a balloon with a small distal profile, by using a balloon with a distal end which is close in actual diameter to the diameter of the piercing member, or by using a balloon which folds into a low profile state, or a combination of these.

Figure 4I:
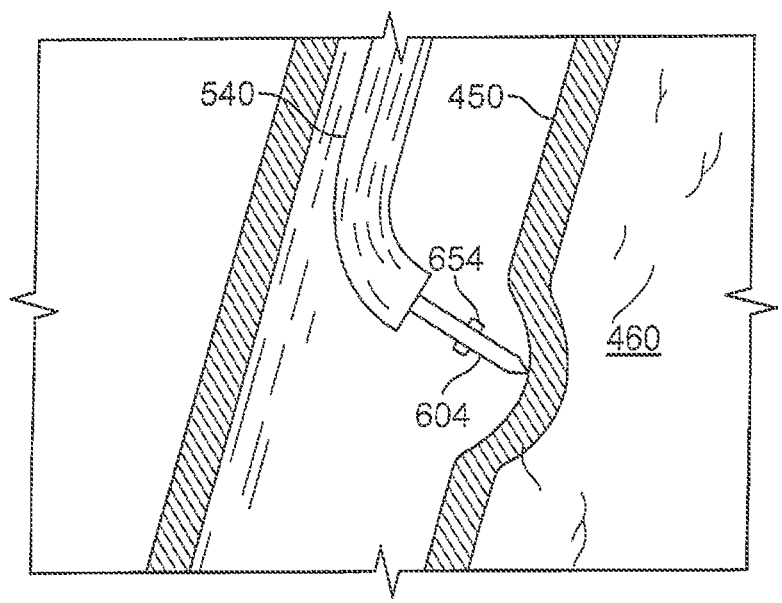

As shown in FIG. 4I, a device of insufficient sharpness will "tent" the airway wall 450. Tenting occurs when a device is placed against an airway wall with significant force but with no puncturing of the airway wall. The airway wall will deflect and become displaced until the device is withdrawn. If the tissue becomes tented there remains a significant amount of potential energy placed by the device onto the airway wall. The potential energy may unexpectedly becomes realized, when the device eventually punctures the airway, which may cause the device to suddenly plunge into the parenchyma to an unintended depth. Plunging may in turn cause unintended damage to the patient. A depth limiting feature 654 may overcome this problem.

Figure 4J:
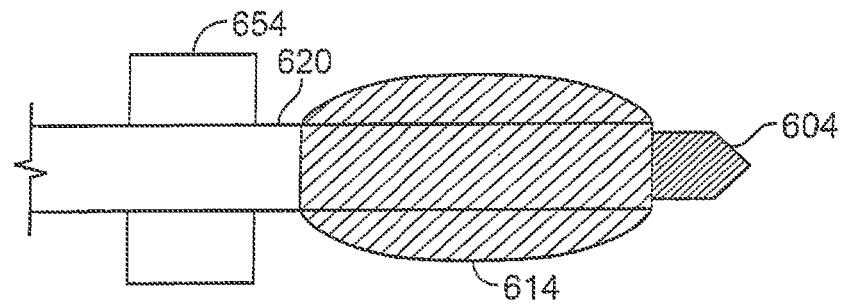

Variations of the invention include a depth limiting feature that may prevent inadvertent advancement of the device when creating the channel. One example of this may be a circular tube 654 placed over the device and set at a fixed distance (e.g. 10 mm) from the distal tip of the piercing member, proximal to the balloon, as shown in FIG. 4J. If the device does tent and plunge into the airway wall the front face of the tube may halt the plunging effect by acting as a barrier. Another example would be a secondary balloon, proximal to the channel expansion balloon, placed in a similar position to the circular tube as described above. Another example would be a folding basket formed from the outer lumen of the device, or constructed from wire.

Figure 4K:
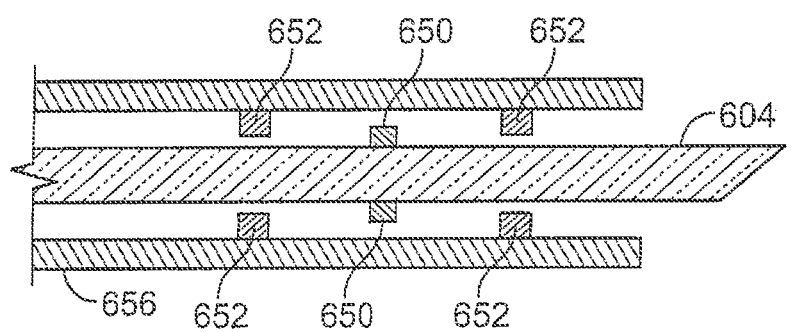

As shown in FIG. 4K, variations of the invention may include a distal collar 650 on the distal portion of the piercing member 604 to precisely limit the maximum extension and retraction of the piercing member 604. The distal collar 650 would be attached to the piercing member and travel between two set collar stops 652 which are attached to the lumen 656 the piercing member travels in. This feature has multiple benefits; first, it has the safety setting a maximum distance for the piercing member to extend, around 2-3 mm has been found to be sufficient in most cases. Thus, the maximum penetration of the piercing member 604 is limited which may prevent unintentional damage to the lung tissue.

The collar 650 protects the bronchoscope by preventing deflection of the distal tip. Deflection can take place when there is a significant amount of gap between the inner sheath 622 and the distal tip of the piercing member in the retracted mode. When the device is being maneuvered through a bronchoscope in a torturous configuration, the lumen 656 can deflect while the stiffer piercing member will not, and thus the piercing member may pierce through the deflected lumen 656 and subsequently into the bronchoscope. By setting a small gap (e.g. <1 mm) this deflection may be eliminated, and the scope protected.

The collar 650 also allows the piercing member to be reliably extended. It was found that when a similar feature was placed at the proximal section of the device the piercing member could not reliably be extended to a set distance beyond the distal tip. This is because when in a torturous configuration the outer sheath 620 of the device may have a tendency to stretch or compress. As a result the tubing may stretch to such a degree that when the piercing member is fully extended it still may not fully extend past the distal tip of the lumen 656. By locating the collar 650 in the distal portion of the lumen 656 (e.g. less than 2 inches from the distal tip) the stretching or compression is minimized or eliminated.

Conduit Deployment Devices and Methods

Figure 5A:
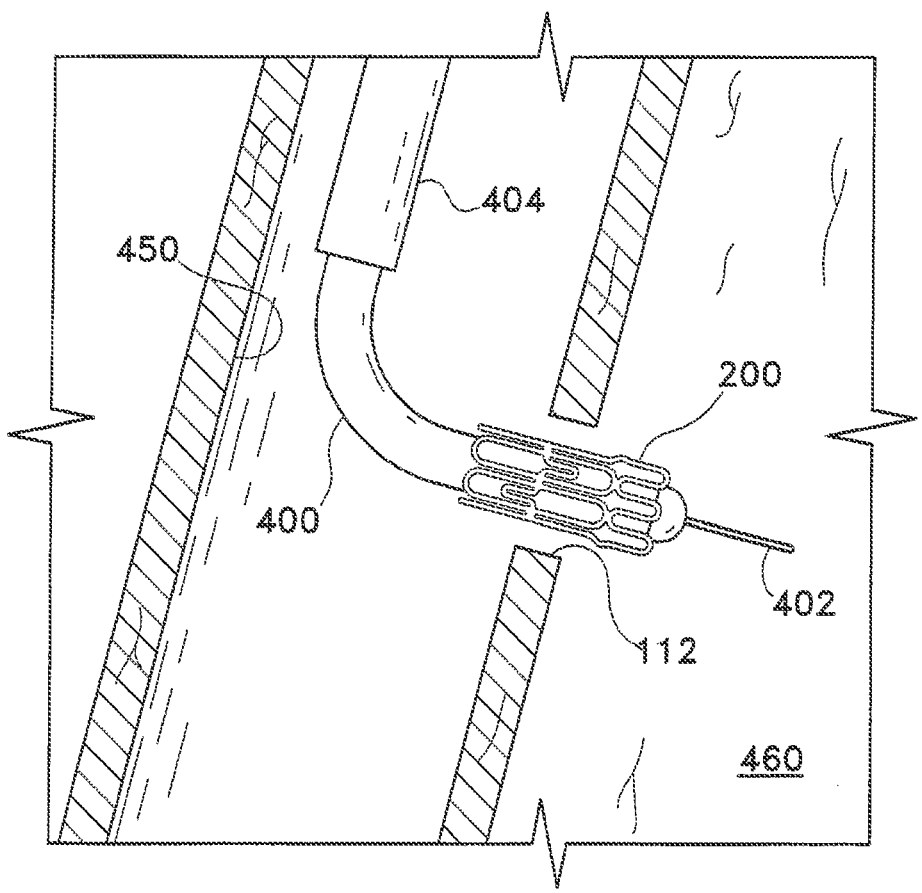
FIGS. 5A-5C illustrate a method for deploying a conduit.
Figure 5B:
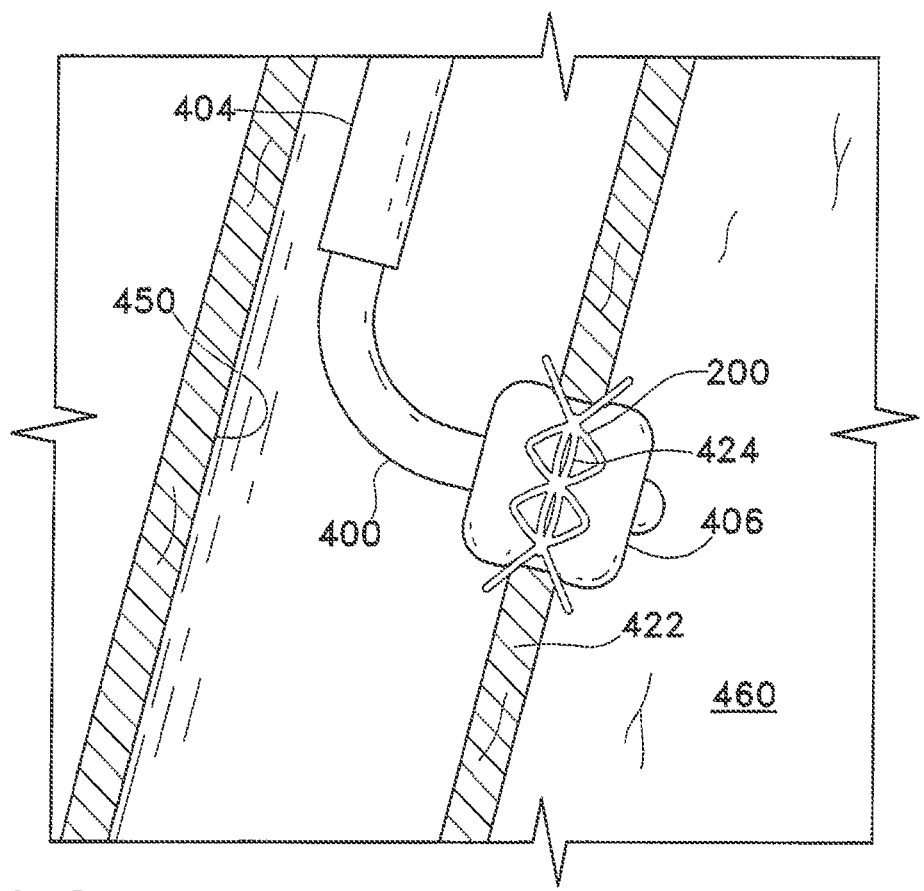
Figure 5C:
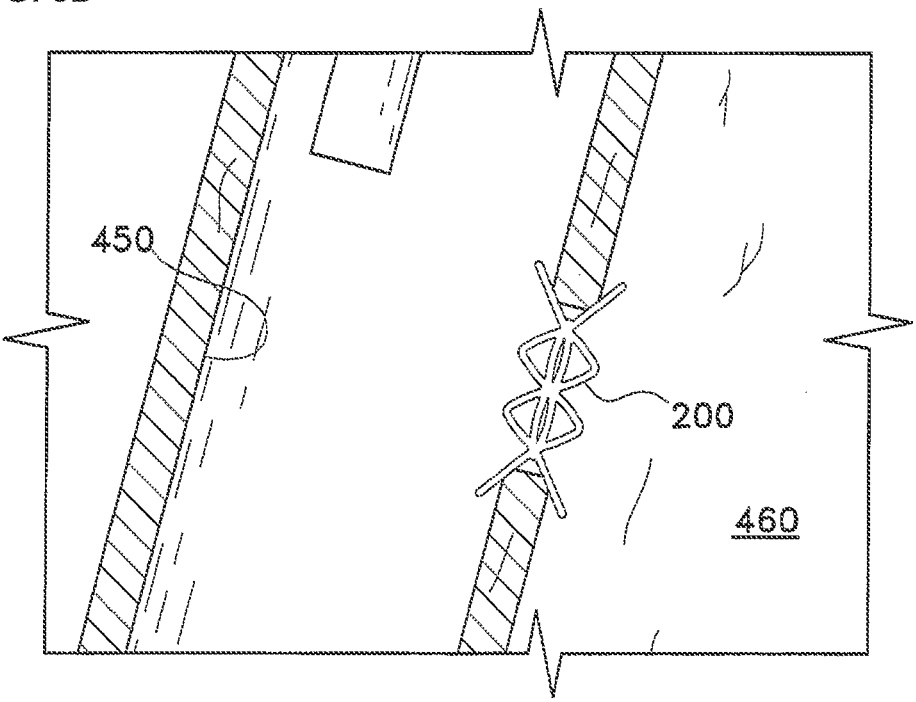

FIGS. 5A-5C illustrate a way to deploy a conduit in a channel. Referring to FIG. 5A, a delivery device 400 is loaded with a conduit 200. An access scope-type device 404 (e.g., an endoscope, a bronchoscope, or other device) may optionally be used to place the delivery device 400 into a collateral channel 112. A guide wire 402 may be used to place the delivery device 400 into the collateral channel 112. The guide wire 402 may be a conventional guide-wire or it may simply be comprised of a super-elastic material. The use of a guide wire is optional as the variations described herein contemplate placement of the conduit 200 using only the delivery device 400.

FIG. 5A also illustrates articulation (or bending) of the deliver device 400 to access the collateral channel 112. However, the one variation also contemplates articulation of the access device 404. The access device 404 may be articulated such that the delivery device 400 may advance straight into the collateral channel 112. Accordingly, the delivery device 400 may exit straight from the access device 404 or it may be articulated into the opening.

FIG. 5B illustrates deployment of the conduit 200. In particular, balloon member 406 is shown in an expanded state resulting in (1) the conduit's center section being radially expanded and (2) the conduit's extension members being outwardly deflected such that opposing extension members sandwich portions of the tissue wall 422. Diametric-control members 424 are also shown in this figure. The diametric or center-control segments limit the center section's radial expansion. In this manner, conduit 200 is securely placed in the channel to maintain a passageway through the airway wall 422.

FIG. 5C illustrates the deployed conduit 200 once the delivery device 400 is removed from the site. It should be noted that dilation of the collateral channel or opening 112 may be performed by mere insertion of the conduit 200 and/or delivery device 400.

It should be noted that deployment of conduits is not limited to that shown in FIGS. 5A-5C, instead, other means may be used to deploy the conduit. For example, spring-loaded or shape memory features may be actuated by mechanical or thermal release and unlocking methods. Additionally, mechanical wedges, lever-type devices, scissors-jack devices, open chest surgical placement and other techniques may be used to deploy the conduit. Again, the conduit 200 may be comprised of an elastic or super-elastic material which is restrained in a reduced profile for deployment and expands to its deployed state upon mechanical actuator or release.

Figure 5D:
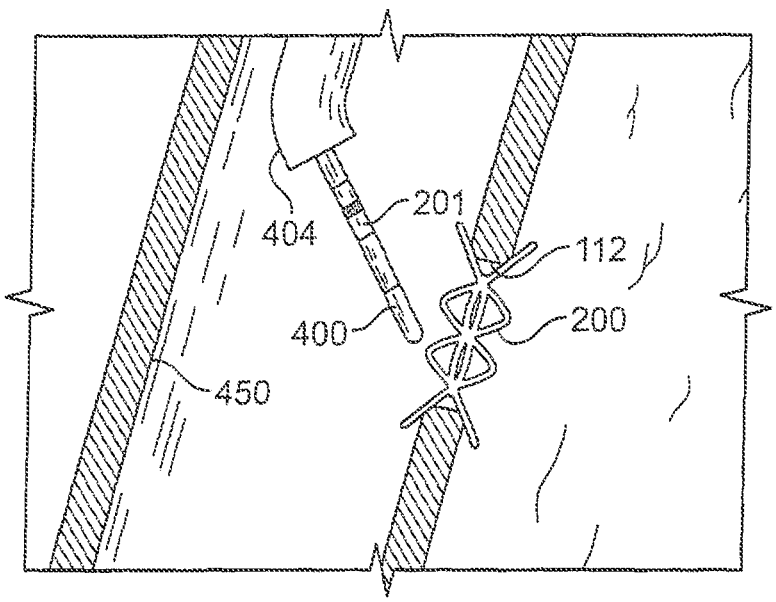
FIGS. 5D-5E illustrate a method for deploying a conduit within another implant.
Figure 5E:
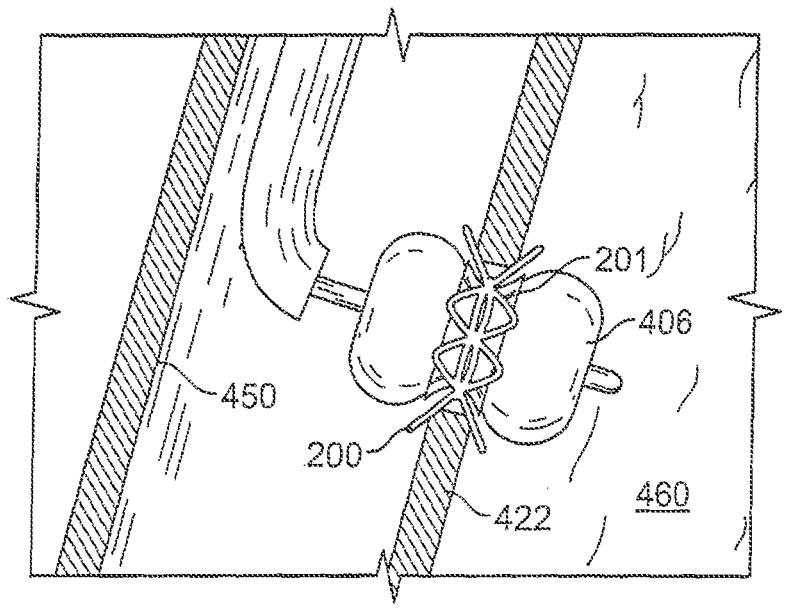

In one additional variation of the invention, as shown in FIG. 5D, a conduit 201 may be deployed within a second structure such as a second conduit or stent. Such an approach may be used to increase retention of the conduits within the channel as well as prevent closing of the channel. For example, an initial conduit 200 or stent may be deployed within the channel 112. This first conduit or stent may have certain properties that make it more acceptable to implantation within the body without generating an aggressive tissue healing response. For instance, the stent may be a drug eluting stent, or the conduit may be constructed from a bio-compatible metal without any additional tissue barrier. Once the initial stent or conduit is placed within the channel 112 a second conduit may be deployed within the first conduit. As shown in FIG. 5D, a first conduit 200 (or stent) is placed within the channel 112. FIG. 5D illustrates a second conduit 201 advanced towards the first conduit 200. FIG. 5E illustrates the second conduit 201 deployed within the first conduit 200. The second conduit 201 may have additional properties that permit the channel to remain patent. For example, the second conduit 201 my have a tissue barrier as discussed above, or other construction that generates an aggressive healing response within the lung. Therefore, the first conduit 200, being more conducive to implantation, will serve to anchor both conduits 200, 201 as the tissue either does not grow, or it grows around the outer conduit 200. The second conduit, for example, may have a tissue barrier placed thereon. Once the second conduit 201 is deployed within the first conduit 200, the tissue barrier of the second conduit 201 will prevent tissue from growing through the stent structure. It should be noted that the structure of a conduit within a conduit may be incorporated into a single composite structure.

In use, the conduit 200 is deployed with the distal side towards the parenchymal tissue 460 while the proximal side remains adjacent or in the airway 450. Of course, where the proximal and distal extension members are identical, the conduit may be deployed with either side towards the parenchymal tissue.

Figure 6A:
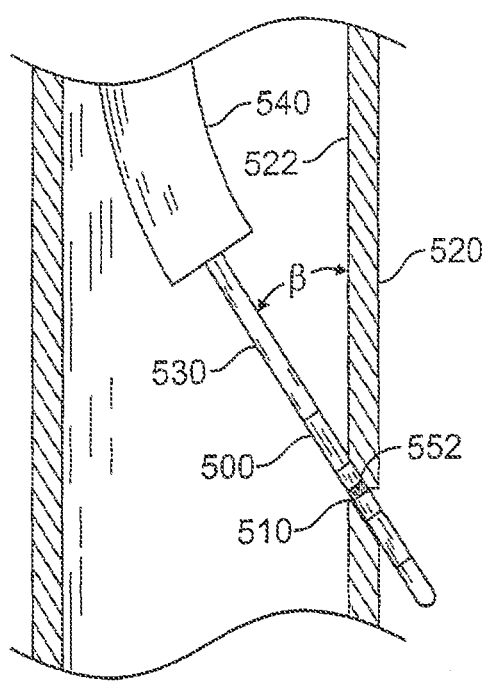
FIGS. 6A-6B illustrate a method for deploying a conduit at an angle.
Figure 6B:
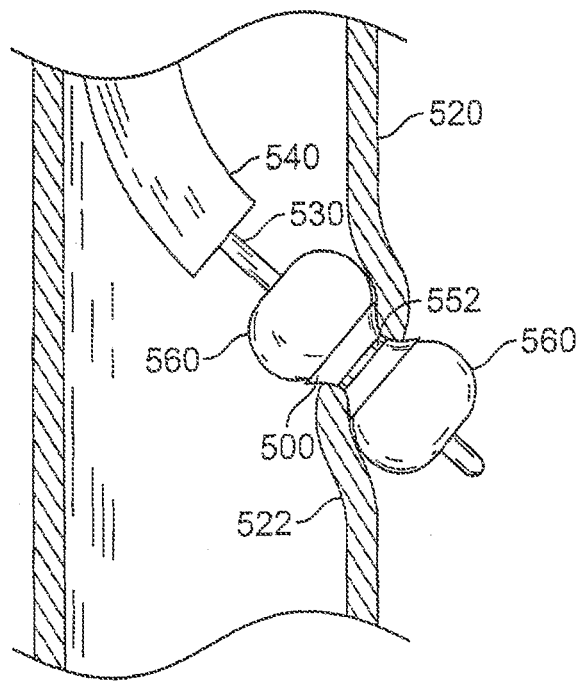

FIGS. 6A-6B illustrate another example of deploying a conduit 500 in a channel 510 (or opening) created in a tissue wall 520. Referring to FIG. 6A, a delivery tool 530 carrying a deployable conduit 500 is inserted into the channel 510. The delivery tool 530 is extended straight from an access catheter 540 such that the delivery tool forms an angle  with the tissue wall 520. It is to be understood that while the tissue wall of airway 522 is shown as being thin and well defined, one variation of a device described herein may be utilized to maintain the patency of channels and openings which have less well defined boundaries. The delivery tool is further manipulated until the conduit is properly positioned which is determined by, for example, observing the position of a visualization mark 552 on the conduit relative to the opening of the channel 510.

FIG. 6B illustrates enlarging and securing the conduit in the channel using an expandable member or balloon 560. The balloon 560 may be radially expanded using fluid (gas or liquid) pressure to deploy the conduit 500. The balloon may have a cylindrical shape (or another shape such as an hourglass shape) when expanded to 1.) expand the center section and 2.) deflect the proximal and distal sections of the conduit such that the conduit is secured to the tissue wall 520. During this deployment step, the tissue wall 520 may distort or bend to some degree but when the delivery tool is removed, the elasticity of the tissue tends to return the tissue wall to its initial shape. Accordingly, the conduits disclosed herein may be deployed either perpendicular to (or non-perpendicular to) the tissue wall.

Figure 7A:
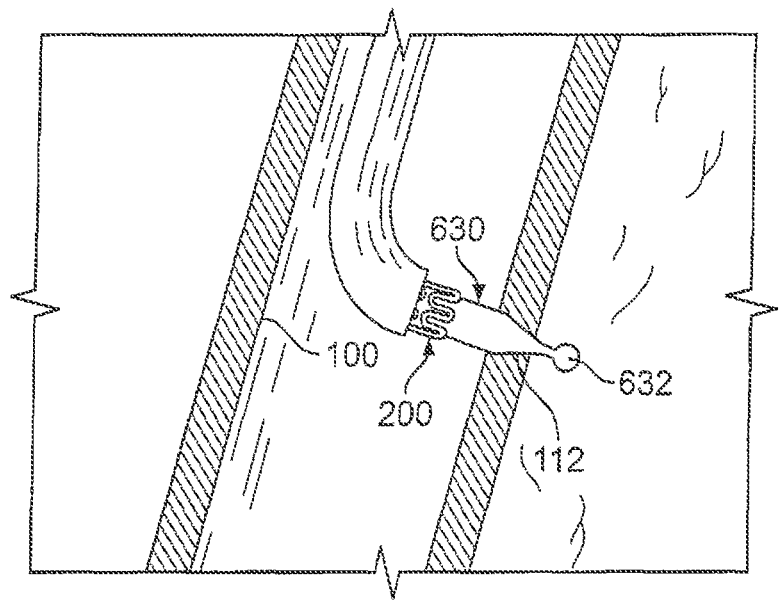
FIGS. 7A-7B illustrate placement of a conduit within a channel by using a guide member.

FIG. 7A illustrates another variation of deploying a conduit 200 into an opening 112. In some variations of the invention, prior to deployment of the conduit 200, the channel 112 may have a diameter or size that may require an additional dilation or expansion of the channel 112 for proper deployment of the conduit 200. For example, the channel 112 may be created by a piercing member, as described above, where the channel 112 nearly closes upon removal of the piercing member. However, the devices and method described herein are not limited to channels 112 of any particular size. The channels may in fact be larger than a diameter of the conduit 200 in its un-deployed state.

In any case, after creation of the channel 112 the surgeon may advance a balloon catheter 630 containing a conduit 200 towards the site of the opening 112. The variation of the balloon catheter 630 depicted in the figure also includes a guide body 632. Because the opening 112 may be difficult to locate, the guide body 632 may serve various functions to assist in locating the opening 112 and placing the conduit 200. For example, as shown in FIG. 7A, the guide body 632 may have a rounded front surface. This allows probing of the catheter 630 against the airway 100 wall to more easily locate the opening 112. The rounded surface of the guide body 632 will not drag on the airway tissue.

Figure 7B:
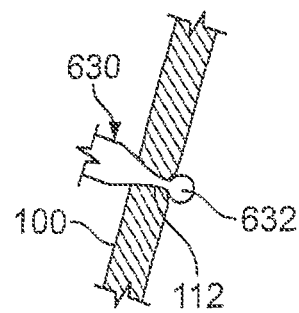

As shown in FIG. 7B, once inserted into the opening 112, the guide body 632 provides an additional function of temporarily anchoring the device 630 within the opening 112. The ability to temporarily anchor the device 630 into the opening 112 may be desirable due to the natural tidal motion of the lung during breathing. The increased surface area of the guide body 632 requires increased resistance upon remove the guide body 632 from the opening 112. Such a feature lessens the occurrence of unintended removal of the device from the site as the lung tissue moves. As shown in FIG. 7B, after insertion into the airway 100 wall, a portion of the guide body 632 serves as a resistance surface to provide the temporary anchoring function. Additional variations of the guide body 632 are shown below.

FIGS. 8A-8F illustrate additional variations of guide bodies 632 for use with certain variation herein. As shown, the guide body 632 is located on the distal end of the balloon catheter 630. The guide body 632 will have a front surface 634 that is preferably smooth such that it can easily be moved over the airway wall. Proximal to the front surface 634, the guide body 632 will have at least one resistance surface 636 which is defined as an area that causes increased resistance upon removal of the guide body 634 from the airway wall. As shown, the resistance surface 636 will be adjacent to an area of reduced diameter 638 to which allows the guide body 632 to nest within the opening 112 in the airway wall. The guide body 632 may have any number of shapes as shown in the figures.

Figure 8A:
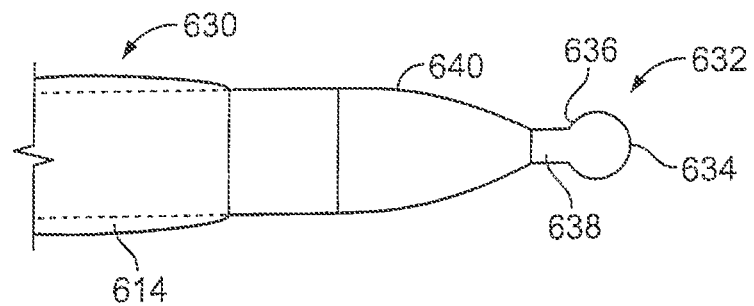
FIGS. 8A-8F illustrate additional variations of guide bodies for use a catheters
Figure 8B:
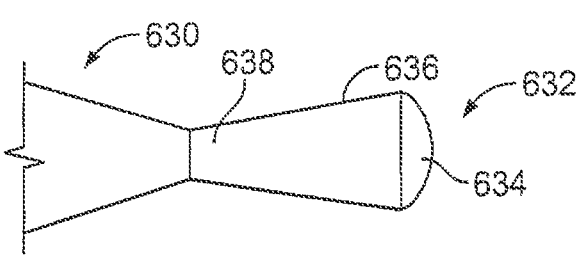
Figure 8C:
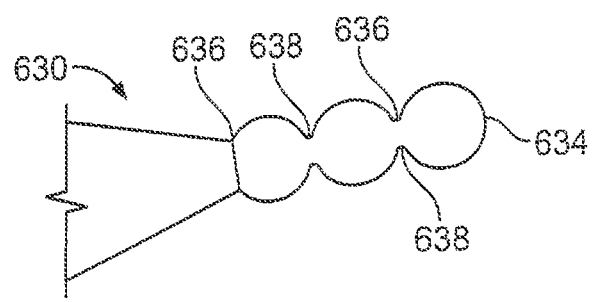
Figure 8D:
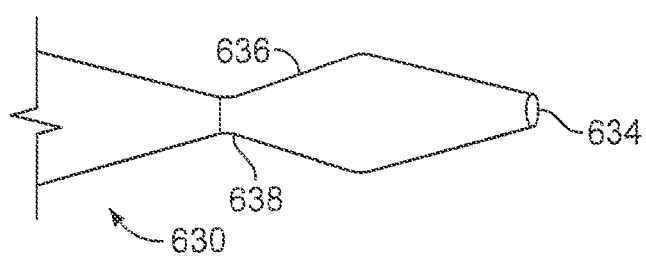
Figure 8E:
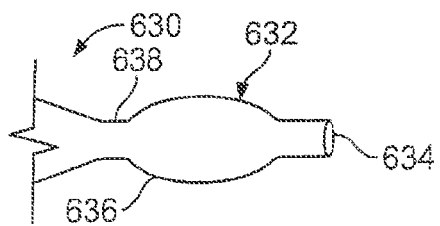
Figure 8F:
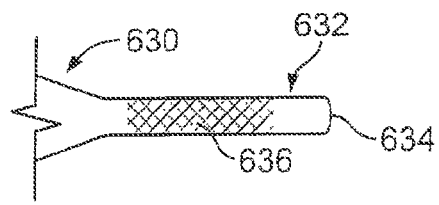

FIG. 8F illustrates another variation of a guide body 632 having a resistance surface 636 which comprises an area of increased surface roughness such that the surface will drag upon the airway wall or tissue surrounding the channel 112. Such a feature may be combined with the variations of the guide members provided above.

The balloon catheters 630 in certain variations may include a dilating member between the guide body 632 and balloon 614. In the variation shown in FIG. 8A, the dilating member comprises a tapered section. However, the invention is not limited as such. For example, the dilating member may comprise a second inflatable balloon, or other expanding device. The dilating members may also be retractable within the elongate shaft.

Figure 9A:
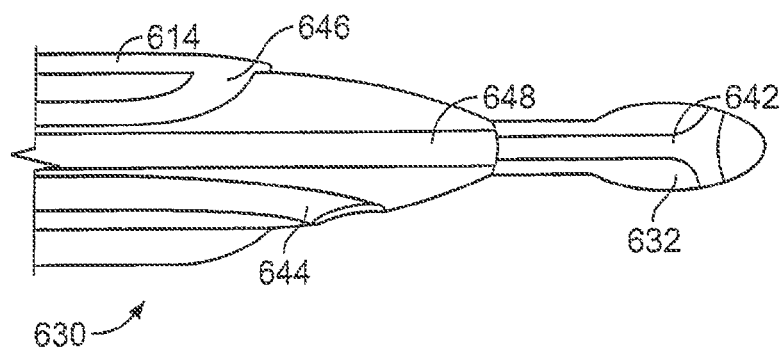
FIGS. 9A-9B illustrate additional features for use with guide bodies.
Figure 9B:
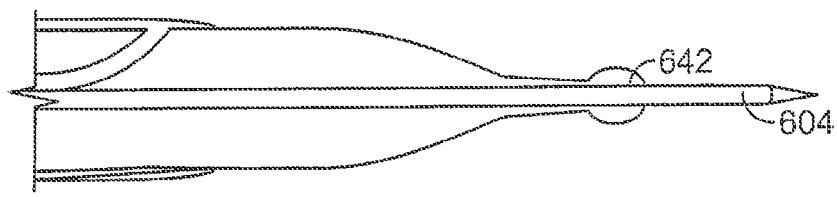

FIGS. 9A and 9B depict cross sections of examples of a balloon catheter 630 having a guide body 632 that includes a lumen 642 which terminates at a surface of the guide body 632. The lumen 642 may be used for suction, irrigation, or deliver bio-active substances, etc. The catheter 630 may also have an additional lumens 646, 646, 648 as shown, for inflation of the balloon 614 and for additional suction 644, and for communication with the guide body lumen 642. As shown in FIG. 8B, the lumen may also be used to advance a piercing member 604 to the airway wall to create the channel 112.

Any of the balloons described herein may be distensible balloons (e.g., they assume a predetermined shape upon expansion) or elastic balloons (e.g., simply expand). Use of a distensible balloon permits control in dilating the opening 112 or placement of the conduit.

Delivery of Medications/Substances to Parenchymal Tissue

In an additional variation, a medical practitioner may create a channel to delivery substances such as bioactive agents, medications, therapeutic substances, or other such materials through the airway wall and directly to the parenchymal tissue of the lung.

In such a case, the practitioner engages many of the steps outlined above such as identifying regions of having severe occurrences of trapped gas or tissue destruction. However, the methods and channel creation techniques described herein may also be suitable for a variety of other disease states affiliated with the lung (especially cancer and treatment of tumors or other growths). In the latter cases, an x-ray, ultrasound, Doppler, acoustic, MRI, PET, computed tomography (CT) scans and/or other non-invasive imaging technique may be employed to locate the region of diseased tissue (such as a tumor). In some cases, if the channel is created solely for the purpose of delivering a substance, then the channel patency techniques described herein may no longer be applicable.

Instead, after delivery of the substance, the medical practitioner may desire closure of the channel.

Once the practitioner identifies a region for creation of the channel, the practitioner may then search for a safe location to penetrate the airway wall (such as using the blood vessel detection techniques described above.

EXAMPLE

Implant

Figure 12:
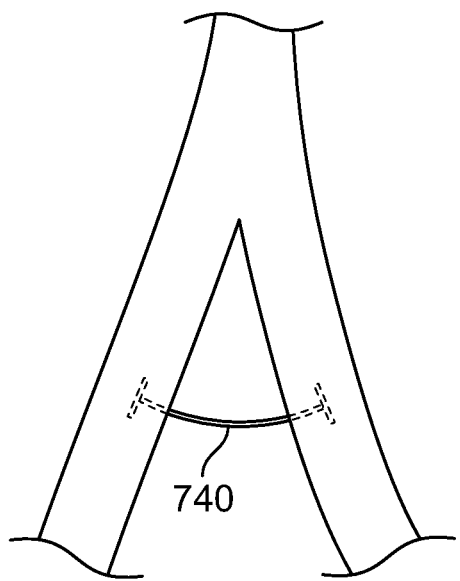
FIG. 12 illustrates another variation of a device for creating a support structure for an airway

Implants comprising stainless steel mesh frame fully encapsulated with a composition comprising silicone (as described below) and paclitaxel were implanted in several canine models. Visual observation indicated that, on average, the passage through the implants remained unobstructed and were associated with significantly reduced fibrotic and inflammatory responses, in canine models, at a considerably higher rate than an implant without any drug adjunct or coronary drug eluting stents (as shown in FIG. 12).

The composition comprised approximately a 9% paclitaxel to silicone ratio with approximately 400 micrograms of paclitaxel per implant. Measurements found that approximately 30% of the paclitaxel released after 60 days. In general, for implants with the paclitaxel/silicone composition, observations of chronic inflammation, epithelial metaplasia and fibrosis were all very mild.

For paclitaxel as the bioactive substance, polymers with solubility parameters between 5-25 (MPa) ^½ were believed to provide sufficient elution rates. The polymer used in the example device has good diffusivity for lipophilic drug (such as paclitaxel) because the side methyl group on the silicone may be substituted with more lipophilic hydrocarbon molecules containing vinyl group or groups in addition polymerization by platinum catalyst.

The composition for the example may be as follow: polymer part: polydimethylsiloxane, vinyldimethyl terminated, any viscosity; and/or polydimethylsiloxane, vinylmonomethyl terminated, any viscosity. The cross-linker part: polydimethylsiloxane, any viscosity; and or polymonomethylsiloxane, any viscosity. Platinum catalyst part and/or cross-linker part: platinum; and/or platinum-divinyltetramethyldisiloxane complex in xylene, 2-3% Pt; and/or platinum-divinyltetramethyldisiloxane complex in vinyl terminated polydimethylsiloxane, 2-3% Pt; and/or platinum-divinyltetramethyldisiloxane complex in vinyl terminated polydimethylsiloxane, ~1% Pt; platinum-Cyclovinylmethylsiloxane complex, 2-3% Pt in cyclic vinyl methyl siloxane.

These components may be combined in different ratios to make the polymer. The hydrocarbon side chain off the silicone back bone makes this polymer system unique and may result in a "zero-order"-like release profile. The amount of vinyl siloxane cross-linker may determine the rate of the drug release and diffusivity of the polymer to the drug. There are other types of polydimethylsiloxanes such as: trimethylsiloxy terminated polydimethylsiloxane in various viscosities, (48-96%) dimethyl (4-52%) diphenylsiloxane copolymer in various viscosities, dimethylsiloxane-ethylene oxide copolymer, dimethyl diphenylsiloxane copolymer, polymethylhydrosiloxane, trimethylsilyl terminated at various viscosities, (30-55%) methyldro-(45-70%) dimethylsiloxane copolymer at various viscosities, polymethylphenylsiloxane, polydimethylsiloxane silanol terminated at various viscosities, polydimethylsiloxane aminopropyldimethyl terminated at various viscosities. For paclitaxel a release profile was found to be acceptable with a polymer system consisting of polydimethylsiloxane vinyl terminated at various viscosity and a range of platinum-mono, di, tri and/or tetramethyldisiloxane complex.

Figure 10A:
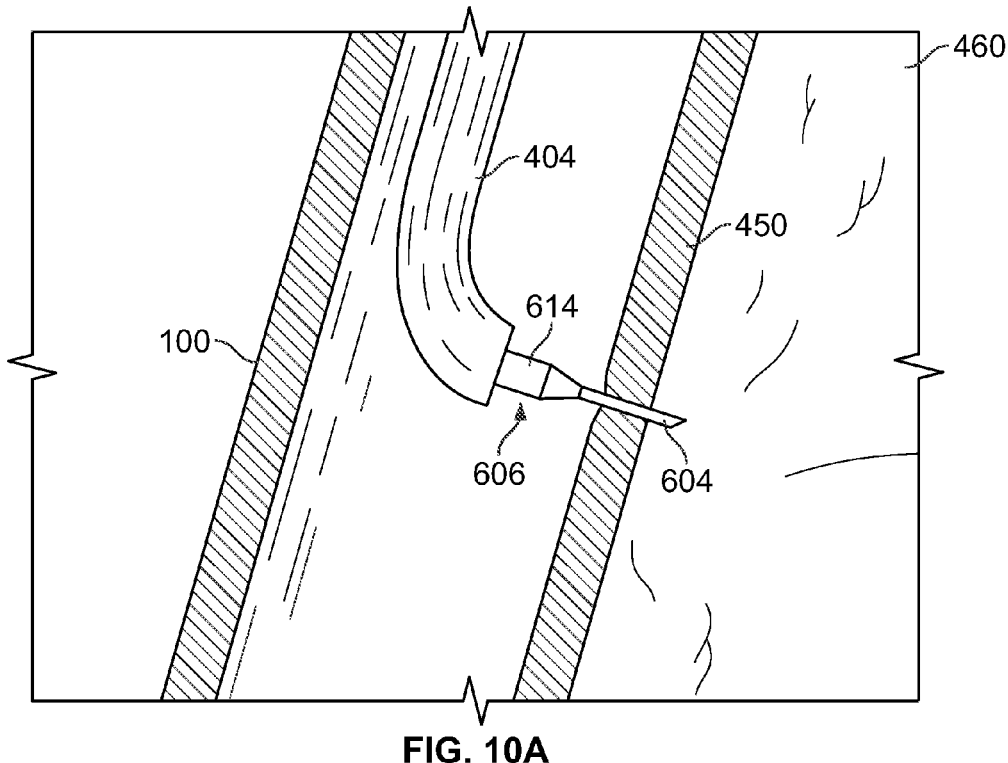
FIGS. 10A-10B respectively illustrate delivery of substances through an opening in the airway and through a conduit placed within the opening.

After finding a suitable location, the practitioner creates the opening or channel. Again, any technique described herein may be used to create the channel. However, FIG. 10A illustrates an example in which a substance may be delivered during creation of the channel. In this example, a similar balloon catheter 606 as described above may have a piercing member 604 that penetrates the airway wall 450. Once through, the practitioner may inject the desired substance into parenchymal tissue 460. Although the illustration shows the piercing member 604 as extending slightly past the airway wall 450, variations of the method include delivering a substance to any location beyond the wall.

Figure 10B:
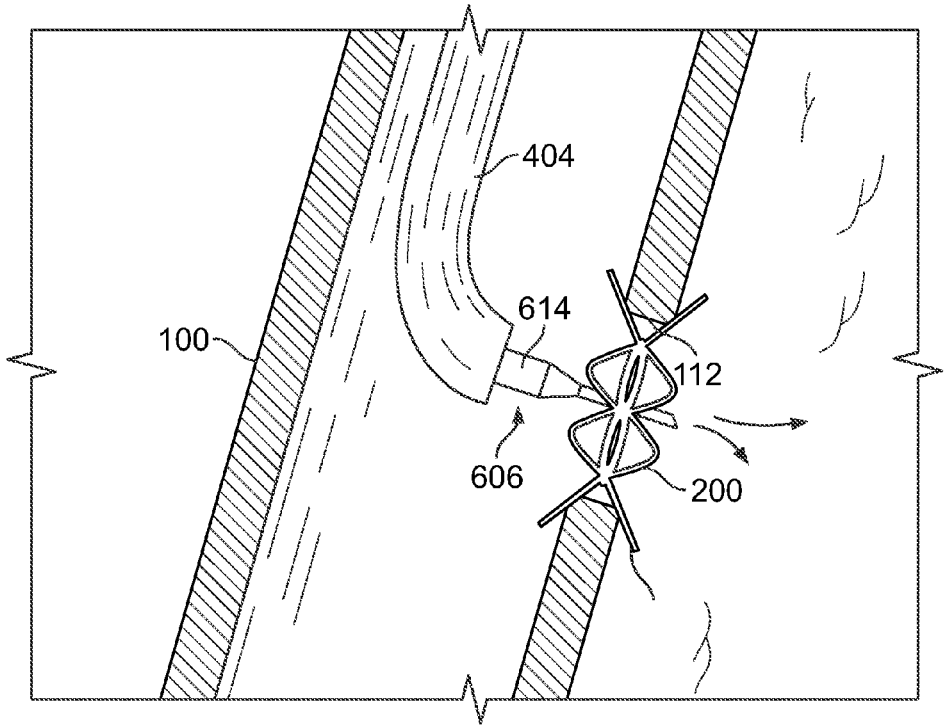

FIG. 10B illustrates another variation of the method. As shown, a substance may be delivered through an existing channel/opening 112. While method may include delivering the substance through a opening 112 with or without an implant 200. In this variation, the channel 112 also includes an implant 200 within the opening 112 with the substance being delivered through the implant 200. Use of an implant 200 may be desirable in those cases where trapped gasses must be evacuate as well as those cases where repeat treatment of a site is planned (e.g., tumor treatment). In addition, the implant 200 may be removed from the channel 112 to either promote or inhibit healing depending on the desired benefit. Naturally, this treatment may be performed in more than one location in the lung, depending on the areas of intended treatment and/or diseased tissue.

The substances that may be delivered as described above may include any of the substances described herein. In addition, examples of bioactive substances include, but are not limited to, antimetabolites, antithrobotics, anticoagulants, antiplatelet agents, thorombolytics, antiproliferatives, antinflammatories, agents that inhibit hyperplasia and in particular restenosis, smooth muscle cell inhibitors, growth factors, growth factor inhibitors, cell adhesion inhibitors, cell adhesion promoters and drugs that may enhance the formation of healthy neointimal tissue, including endothelial cell regeneration. The positive action may come from inhibiting particular cells (e.g., smooth muscle cells) or tissue formation (e.g., fibromuscular tissue) while encouraging different cell migration (e.g., endothelium, epithelium) and tissue formation (neointimal tissue).

Still other bioactive agents include but are not limited to analgesics, anticonvulsives, anti-infectives (e.g., antibiotics, antimicrobials), antineoplastics, H2 antagonists (Histamine 2 antagonists), steroids, non-steroidal anti-inflammatories, hormones, immunomodulators, mast cell stabilizers, nucleoside analogues, respiratory agents, antihypertensives, antihistamines, ACE inhibitors, cell growth factors, nerve growth factors, anti-angiogenic agents or angiogenesis inhibitors (e.g., endostatins or angiostatins), tissue irritants (e.g., a compound comprising talc), poisons (e.g., arsenic), cytotoxic agents (e.g., a compound that can cause cell death), various metals (silver, aluminum, zinc, platinum, arsenic, etc.), epithelial growth factors or a combination of any of the agents disclosed herein.

Examples of agents include pyrolitic carbon, titanium-nitride-oxide, taxanes, fibrinogen, collagen, thrombin, phosphorylcholine, heparin, rapamycin, radioactive 188Re and 32P, silver nitrate, dactinomycin, sirolimus, everolimus, Abt-578, tacrolimus, camptothecin, etoposide, vincristine, mitomycin, fluorouracil, or cell adhesion peptides. Taxanes include, for example, paclitaxel, 10-deacetyltaxol, 7-epi-10-deacetyltaxol, 7-xylosyl-10-deacetyltaxol, 7-epi-taxol, cephalomannine, baccatin III, baccatin V, 10-deacetylbaccatin III, 7-epi-10-deacetylbaccatin III, docetaxel.

In addition, the substances may be selected to induce a biologic lung volume reduction such as by using a talc compound, lung irritant, or fibrin hyrogels containing fibroblast growth factor −1. The use of such compounds may be found in: U.S. patent application Ser. No. 09/590,790, filed Jun. 8, 2000, now abandoned, entitled MINIMALLY INVASIVE LUNG VOLUME REDUCTION ASSEMBLY AND METHOD; U.S. patent application Ser. No. 10/679,065 filed Oct. 3, 2003, now abandoned, entitled MINIMALLY INVASIVE LUNG VOLUME REDUCTION ASSEMBLY AND METHOD; and FIBROBLASTS GROWTH FACTOR-1 THERAPY FOR ADVANCED EMPHYSEMA—A NEW TISSUE ENGINEERING APPROACH FOR ACHIEVING LUNG VOLUME REDUCTION to Ingenito et al. *J. Bronchol, Vol.* 1, 3 Jul. 2006.

Various procedures described herein and below may be performed through an extra-anatomic opening, opening, port or channel through an airway wall in the lung or respiratory system. Various devices or instruments may be advanced within or to the airway and out through an extra-anatomic opening or port or surgically created opening, port or channel through an airway wall, into the lung tissue, parenchyma or other tissue in the body, where the devices or instruments may be used to perform a variety of procedures on various tissues within the body. Various methods, devices and systems for diagnosing, monitoring, and/or treating medical conditions through an extra-anatomic opening or port through or in an airway wall are described in detail below. In certain variations, the opening, port or channel may be held open by placing a temporary or permanent structure such as a stent, shunt, or sheath in the opening, through which to operate and/or advance other devices, instruments, compositions and/or drugs. One or more, e.g., multiple, openings, ports and/or channels may be created (with or without multiple temporary or permanent structures) to provide different access points to the target regions, e.g., to access a tumor, nodule, lymph node or other tissue for assessment, monitoring, destruction, or removal.

A variety of procedures may be performed through an extra-anatomic opening or port through an airway wall including for example: diagnostic sampling; visual imaging; instilling or delivering drugs; microscopic imaging such as optical coherence tomography (OCT); tissue ablation, e.g., cryo, ultrasound, microwave, laser, radiofrequency (RF), etc.; injection of various substances, e.g., stem cells, antibiotics, antiproliferitives, chemo therapy agents; use of an excision or cutting snare; removal; resection; use of forceps; placing markers or fiducials; tissue or organ modification, implantation of various artificial structures, and hypothermia procedures.

Figure 11:
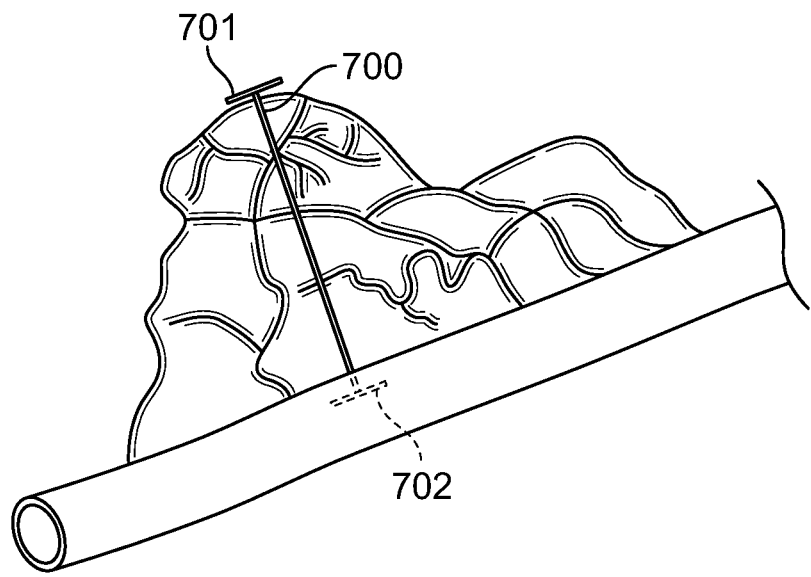
FIG. 11 illustrates a variation of a device for creating a support structure for an airway.

FIG. 11 illustrates one variation of a device for creating a support structure for an airway, such as a floppy airway, which expands and/or holds or stents open the lumen of an airway. Various conditions, e.g., emphysema, cause lung tissue and parenchyma destruction, which results in airways becoming floppy and losing their rigidity. When air is drawn through an airway having these conditions, the airway tends to collapse due to the Bernoulli effect, trapping gas and causing the lungs to become hyperinflated.

As shown in FIG. 11, a clamp 700 may have a grasping end 701 and an anchoring end 702. In use, the clamp may be advanced through the extra-anatomic opening or port in the airway wall, into the parenchyma where the grasping end is used to capture or grab healthier parenchyma, which is not immediately adjacent to the airway wall, but sits beyond the destructed tissue. The anchoring end 702 of the clamp remains within the airway lumen, allowing the clamp 700 to tether the captured parenchyma to the airway wall. As a result of the tethering, the captured parenchyma will exert a pulling force on the anchored clamp, pulling on the airway wall such that the airway lumen remains open and does not collapse on itself. The tethering may prevent the airway lumen from collapsing or substantially narrowing in diameter.

Any device or mechanism that may be used to capture and tether parenchyma to an airway wall may be utilized. Examples include but are not limited to, clamp made from various materials, e.g., nitinol, or a suture for anchoring parenchyma to an airway wall. The anchoring end 702 may include a t-bar or other design for anchoring the clamp 700 to the airway wall, preventing the clamp 700 from being pulled completely through the extra-anatomic opening or port and out of the airway. Any device that applies enough force to break the Bernoulli effect on the airway walls and prevent collapsing of the airway lumen on itself may be utilized. In certain variations, the grasping end of the clamp may be a t-bar, a barb, or a hook.

FIG. 12 illustrates another variation of a device for creating a support structure for an airway or floppy airway, which expands and/or holds or stents open the lumen of an airway. An anchor 740 is provided, the first end of the anchor includes a t-bar and the second end includes a t-bar. The anchor may also be in the form of a hook, barb, suture, loop, or plate. The anchor 740 may be advanced through an extra-anatomic opening or port of a first airway and into a second airway, advancing through destroyed lung tissue or parenchyma in between, and anchoring the first and second airways to each other. The t-bars at either end of the anchor will be forced against the inner airway wall of the respective airways in which they are positioned, pulling the airways toward each other. As a result, the airway walls may be pulled away from the center of the respective airway lumen, and the airway lumen of each airway may be held open, preventing the airway walls from collapsing on themselves and preventing the airway lumen from collapsing or substantially narrowing in diameter.

Figure 13:
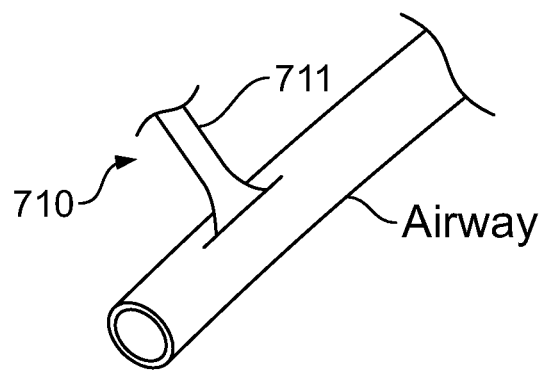
FIG. 13 illustrates a variation of a device for creating a channel or pathway through an opening or port in an airway wall.

FIG. 13 illustrates one variation of a device for creating a channel or pathway through an extra-anatomic opening or port in an airway wall, through which instruments or tools may be passed. The device 710 may include an outer tube 711 and an inner tube (not shown). In use, the outer tube 711 is passed through an extra-anatomic opening or port in the airway wall. The inner tube is advanced through the outer tube 711. The device 710 is clamped to the airway wall, providing a passage through which various instruments or tools may be passed. The passage may extend any distance beyond the extra-anatomic opening or port into the lung tissue and may also extend from the airway wall back into the airways some distance including up to the mouth or nose, or it may be positioned inside a scope. The device 710 may provide an artificial channel for the advancement of an instrument, e.g., for procedures where several passes of an instrument are required to effect treatment. In one variation, an instrument may make several passes through the artificial channel created by device 710 in order to break up and/or remove a large mass of tissue. In another variation, it may be used to reliably return to a site so that multiple tissue samples can be taken. In yet another variation, it may be used to deliver multiple doses of a substance or substances to the lung tissue. In all of these cases, it may be left in place temporarily, e.g. during a single procedural, or for longer periods of time, e.g. over multiple procedures across several or many days.

Figure 14:
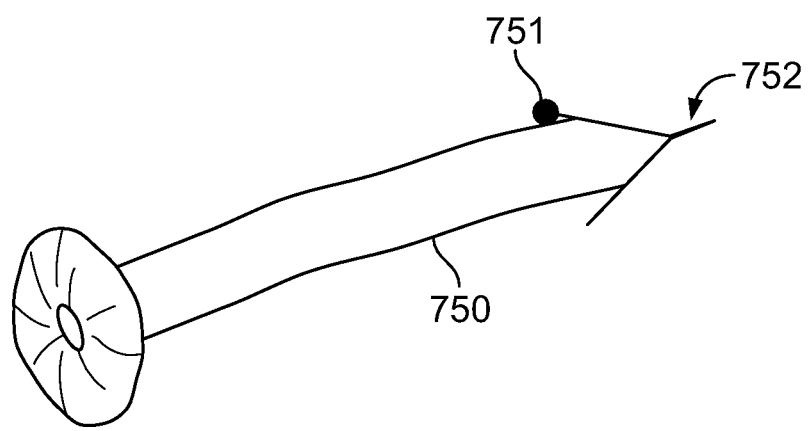
FIG. 14 illustrates a variation of a device for delivering instruments or tools through an opening or port in an airway wall.

FIG. 14 illustrates another variation of a device for delivering instruments or tools through an extra-anatomic opening or port in an airway wall. A device in the form of a catheter 750 or other elongate instrument, such as a steerable or non-steerable catheter, delivery catheter, or guide sheath may be provided and advanced through an extra-anatomic opening or port in an airway wall. The catheter may include a needle 752 or sharpened tip at its distal end, allowing the catheter to be advanced or driven through tissue to reach a target destination. It may also include a rounded tip to dissect through less dense tissue. The catheter may include an electromagnetic or magnetic chip 751, sensor or other tracking device at its distal end to facilitate navigation and/or tracking of the catheter to position the catheter at the target destination. For example, an external electromagnetic field or electromagnetic sensor may be utilized to guide and/or track the catheter or any other devices or substances delivered from the elongate instrument or catheter. The electromagnetic field may be movable.

In certain variations, navigation technology that incorporates other forms of real time imaging such as ultrasound, fluoroscopy, CT, MRI, or PET may be utilized to guide or track the catheter as it is moved or advanced through tissue. Once the catheter is positioned at the target destination, the catheter may act as a platform through which various instruments and/or tools may be delivered. For example, biopsy forceps, forceps, injection needles, ablation and/or cryoablation catheters may be delivered through the catheter and through the extra-anatomic opening or port in the airway wall, to a target site to perform the desired procedure.

In certain variations, the electromagnetic field may be registered to a 3D model of the lung which has been reconstructed from a set of radiographic images. The radiographic images may be from a CT scan.

In one example, a target tumor may be identified and/or tracked using the aforementioned navigation technology. The catheter may be navigated through an extra-anatomic opening or port in an airway wall, toward the target tumor, using an electromagnetic field. An instrument may then be advanced through the catheter, guide sheath or delivery catheter, to the tumor to perform the desired procedure.

Various devices or methods for collapsing lung tissue or parenchyma and/or providing a compression system for a damaged or injured lung tissue where the lung tissue or parenchyma is accessed through an extra-anatomic opening or port in an airway wall are provided. A clamp made from a shape memory metal and having a variety of shapes may be utilized. In use, the clamp may be advanced through an extra-anatomic opening or port in an airway wall and into parenchyma or lung tissue. The clamp may expand upon exiting the extra-anatomic opening or port and it may grab, push, pull, compress, extend, collapse, or reshape parenchyma or lung tissue.

Figure 15:
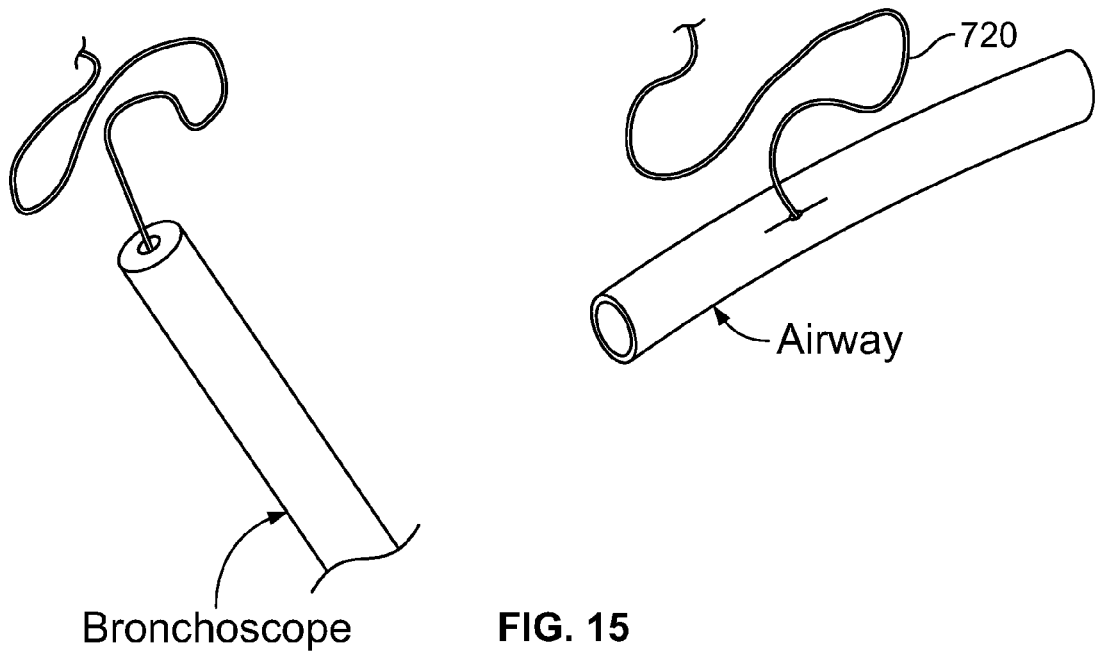
FIG. 15 illustrates a variation of a clamp for collapsing tissue.

In one variation, as illustrated in FIG. 15, the clamp may be in the form of a butterfly clamp 720. The butterfly clamp 720 may be made from a shape memory material. The butterfly clamp 720 is advanceable through the airway and through the extra-anatomic opening or port in the airway wall in a straight wire configuration. In order to maintain the clamp in a straight wire configuration, it may be deployed from a semi rigid tubular member which has been fed into the airways from the mouth or nose with or without the use of a bronchoscope. Upon exiting the airway via the extra-anatomic opening or port, the butterfly clamp 720 becomes unconstrained and reverts to a predetermined expanded shape. The end of the clamp that remains inside the airway lumen may include one or more anchors or barbs which may penetrate into the airway wall.

In use, the butterfly clamp 720 is advanced through the extra-anatomic opening or port in the airway wall and into the lung tissue or parenchyma. The butterfly clamp expands into a predetermined shape upon exiting the extra-anatomic opening or port. The butterfly clamp grasps or attaches to destructed lung tissue or parenchyma. The clamp may be screwed, twisted or cranked down, bringing the opposing ends of the clamp toward each other and toward the airway wall. As the butterfly clamp is cranked down, it compresses and/or collapses the grasped destructed lung tissue or parenchyma, and the anchors are forced into the inner airway wall. The anchors insert themselves into the airway wall, anchoring down the clamp and preventing the clamp from untwisting or unwinding.

In any of the variations described herein, the device may be advanced through an extra-anatomic opening or port in an airway wall, into lung tissue or parenchyma and return into the airway via a second site or second extra-anatomic opening or port located at a different position on the airway wall. Accordingly, a first end and second end of a device could both be positioned within the airway. In certain variations, one or both ends may include an effector element, e.g., an electrode for providing stimulation to tissue, and a center portion of the device, which remains outside of the airway and within the lung tissue or parenchyma, may include an effector element for treating, collapsing, and/or compressing destructed lung tissue or parenchyma. In one variation, a device may be in the form of a vent tube which extends outside of the airway at a first location, through lung tissue or parenchyma, and back into the airway at a second location. The vent tube may act as a French drain. Optionally, a device may return to the airway lumen through the same extra-anatomic opening or port through which the device exited.

In another variation, a method for reducing the volume of bullae or other tissues or portions in the lung, via an extra-anatomic opening or port in an airway wall is provided. A needle may be advanced through an extra-anatomic opening or port in an airway wall to a bulla where the needle is used to suck fluid or air from the bulla. A sclerosing agent, e.g., talc, hypertonic saline, sodium neododeclyl chloride, or tetracycline aqueous solution, may be inserted into the bulla to coat the inside surface of the bulla to keep the bulla collapsed, flat, or closed. The suction step and the step of injecting a sclerosing agent may take place in any order or simultaneously. In certain variations, a sealant or sealer may be injected into a bulla prior to sucking air out of the bulla, to seal any holes or leaks that may exist in the bulla. A bulla may be located or targeted using a CT scan or other visualization technique.

Another variation of a method for reducing the volume of bullae via an extra-anatomic opening or port in an airway wall includes injecting or inserting a sclerosing agent, e.g., talc, hypertonic saline, sodium neododeclyl chloride, or tetracycline aqueous solution, and optionally a visualizing agent, e.g., contrast agent into a bulla. The sclerosing agent and visualizing agent may be mixed to form a slurry or solution and the solution may be injected into a bulla. The solution may seal off any collateral ventilation or openings in the bulla, while optionally allowing for visualization of the bulla. The bulla may then be suctioned and/or flattened down, leaving all or some of the sclerosing agent to remain in the bulla, which sclerose or adhere the inner surfaces of bulla to each other to keep it flattened and compressed down.

In certain variations, a sclerosing agent/contrast solution may be injected into a bulla and visualized, e.g., under fluoroscopy. By observing or visualizing where the solution migrates in the lung, it may be determined whether the bulla is closed off to collateral air channels or not. If visualization shows that the solution remains in a closed off or confined area, suction may be applied to the bulla to suck down or flatten the bulla. In certain variations, a rigid bronchoscope, custom rigid scope, or flexible bronchoscope or other scope may be utilized to reach an extra-anatomic opening or port in an airway or to reach the upper lobes of a lung for delivery of the solution and suction device. A large lumen needle may be utilized to suction and remove air or other fluid from the bulla.

Figure 16:
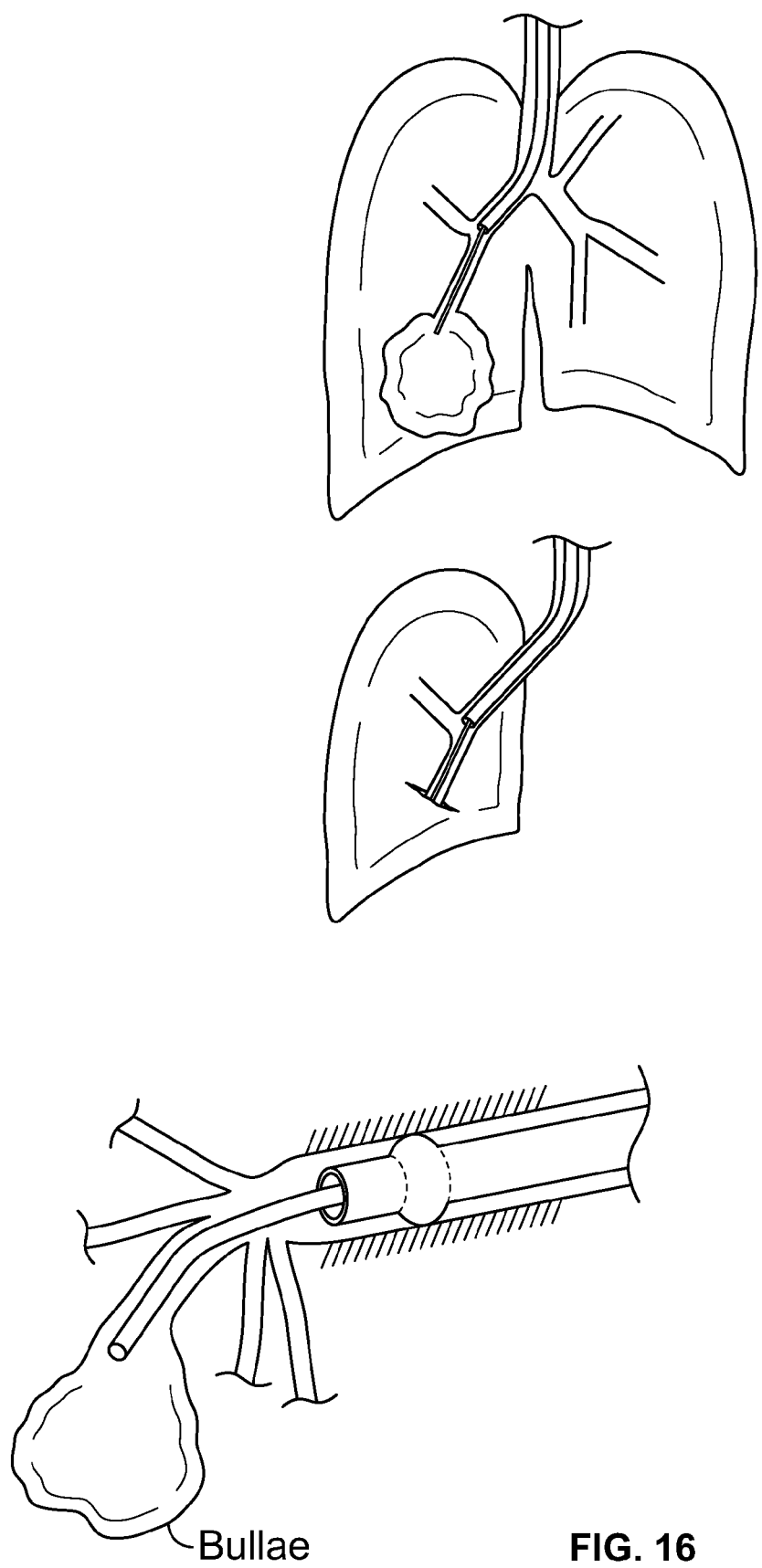
FIG. 16 illustrates method for reducing the volume of bullae in the lung, via an opening or port in an airway wall.

In another variation, as shown in FIG. 16, the inside surface of a bulla may be coated with an adhesive or wound closing or sealing material. The bulla may be collapsed with vacuum and the adhesive or wound closing or sealing material may maintain the bulla in a collapsed state or permanently collapse the bulla. The adhesive or wound closing or sealing material may be delivered into the bulla from the distal end of a catheter via an extra-anatomic opening or port in an airway wall. A proximal end of the catheter may have an interface to deliver and/or remove adhesive or wound closing or sealing material. In one variation, a multi-lumen catheter may include a lumen for delivery or removal of an adhesive, wound closing or sealing material, or other material; the other lumen may comprise a vacuum lumen. Also, a balloon or expandable member on the outer surface of the catheter may be expanded to seal proximal to a treatment site. In one variation, a bulla may be accessed via an extra-anatomic opening or port in an airway wall. Adhesive may be delivered into a bulla and then excess adhesive may be removed and vacuum is applied to collapse the bulla. The vacuum may continue to be applied until the adhesive sets.

In another variation, methods and devices are provided for treating emphysema or other conditions by trapping or compressing destructed lung tissue in hyperinflated areas of the lung and reducing the amount of trapped air in the hyperinflated areas of the lung. A barbed wire, e.g., a nitinol wire, may be inserted through an extra-anatomic opening or port in an airway wall and into a hyperinflated area of the lung. The lung tissue attaches or sticks to the barbed wire. The tissue is closed down around the wire and the tissue necroses to the wire over time. This results in less tissue and air filling up a patient's lung, which allows the diaphragm to raise up, so the patient can breathe more efficiently. In an alternative variation, an adhesive or sticky substance or fly paper may be used to grab and close down or reduce the size of the hyperinflated tissue. The respiratory function of the lung may create a suction that continuously pulls down areas of tissue, causing the tissue to glob together on the barbed wire or adhesive, thereby reducing the size of the large hyperinflated area.

In another variation, a lapband or other cinching device may be introduced through an extra-anatomic opening or port in an airway wall to compress hyperinflated segments of a lung. The lapband or cinching device may be placed around a lobe or section of a lobe of the lung and cinched down to condense or reduce the amount of hyperinflated tissue in the lung.

Another method for compressing hyperinflated segments of a lung includes filling at least part of the pleural space with an expandable material. The expandable material provides as an external compression force. For example, where an upper anterior segment of the left lung is hyperinflated, the lung may be accessed via an extra-anatomic opening or port through an airway wall (or alternatively from outside the lung) and an extrapulmonary blob of silicone or other material may be injected into the pleural space. This results in compression of that segment of the lung and prevents the lung segment from reexpanding or hyperinflating.

Figure 17:
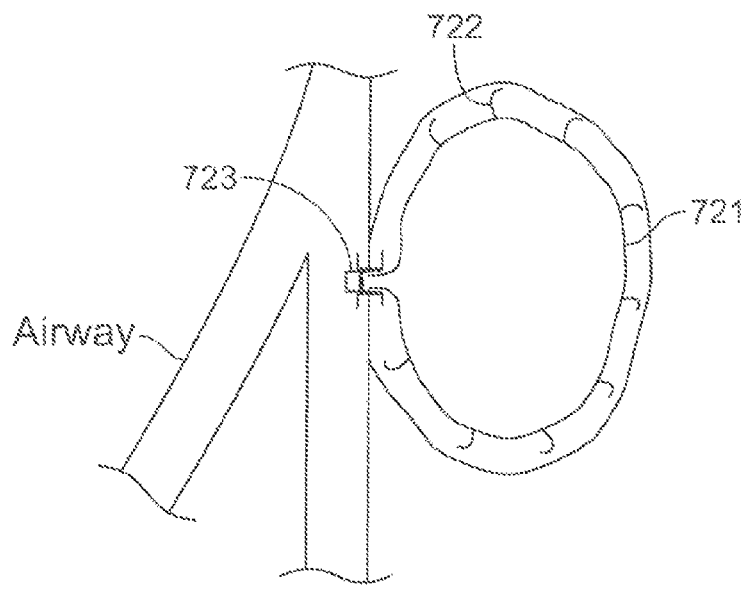
FIG. 17 illustrates a variation of a device and method for compressing hyperinflated segments of a lung.

FIG. 17 illustrates another device and method for compressing hyperinflated segments of a lung, which includes inserting a collapsible balloon 721 (elastic or inelastic) through an extra-anatomic opening or port through an airway wall and into the lung. The outside of the balloon may be covered with barbs 722 or an adhesive for grabbing tissue. The balloon 721 is expanded in the lung bulla or segment, and the outer surface of the balloon 721 sticks to and grabs the inner surface of the wall of the lung bulla or segment. The balloon 721 is allowed to collapse, deflated or suctioned down—the entry port of the balloon may optionally be sealed to prevent re-expansion—causing the lung bulla or lung segment or tissue to collapse and compress down with the balloon. The balloon 721 coats the inner wall of a bulla or lung segment and prevents collateral ventilation from refilling the collapsed portion of the lung.

The balloon 721 may break up lung tissue or parenchyma as it is expanded. In one example, a glutaraldehyde based adhesive may be applied to the outer surface of the balloon. Optionally, a grommet 723 or plug may be used to plug the airway opening or port to the collapsed bulla or segment of the lung to keep the segment collapsed and sealed. The plug may be inserted through the opening in the airway wall. A variety of balloons or other structures may be used to collapse the lung segment. For example, the balloon may be porous, able to secrete an adhesive or other substance. The balloon may be made of collagen, e.g., where the balloon is nonelastic and folded down on itself. Optionally a cage which is mechanically expandable and collapsible may be used instead of a balloon. A balloon may be allowed to collapse or the air may be sucked from the balloon.

Another method for compressing hyperinflated areas of a lung includes inserting one or more anchors with lines connecting the anchors through an extra-anatomic opening or port in an airway wall, into a bulla or lung segment. The anchors insert into the bulla or lung segment wall or tissue and the lines are pulled down to collapse and hold down the bulla or lung segment. Alternatively, a lobe or section of a lobe may be collapsed or folded over on itself and closed off by inserting a bendable wire or rod through an opening or port in an airway wall and/or through the pleura. The wire or rod may be bended to mechanically fold down and retain the lobe in a collapsed state, preventing it from refilling with air. Alternatively, a lobe may be removed through an extra-anatomic opening or port in an airway, e.g., after the lobe has been excised, cut up, or broken down by morcellation.

Methods for performing minimally invasive lung volume reduction surgery via an extra-anatomic opening or port in an airway wall, to remove trapped gas and prevent gas from refilling the lung or re-accumulating in the lung, is provided.

In another variation for reducing the volume of a tissue mass or tissue void or bulla in a lung via an extra-anatomic opening or port in an airway wall thermal energy may be applied to shrink tissue, where the thermal energy may be delivered via an extra-anatomic opening or port in an airway wall. Thermal energy may be applied to various lung tissues, including, airway walls, blood vessels, parenchyma tissue, other collagen tissue and other components of the lung in a manner sufficient to cause the tissue to shrink. For example, the thermal energy may be delivered at 75° Celsius for about 20 seconds or greater to effect tissue shrinkage. After the tissue is reduced in size, the smaller "at rest" size of the tissue may act as though its spring constant has been increased, restoring driving force and/or force balance of the tissue. Various forms of thermal energy at various frequencies may be utilized, including, for example, light energy, laser light energy, microwave energy, radio frequency, direct electrical resistivity of tissue (e.g., DC, AC, or RF), conductive heat transfer from a heated probe or instrument, hot fluid or gas, frictional thermal energy (e.g., ultrasonic, RF, or slower oscillating motion probe), and/or chemical reactions which release heat. The application of thermal energy may be localized and used for treating specific segments of the lung or airway or the energy may be applied grossly to treat an entire lung or lobe, e.g., with microwave.

Figure 18A:
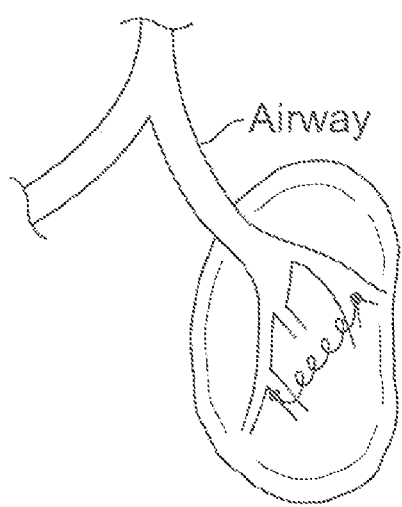
FIGS. 18A-B illustrate variations of elastic members to be affixed to tissue within a lung.
Figure 18B:
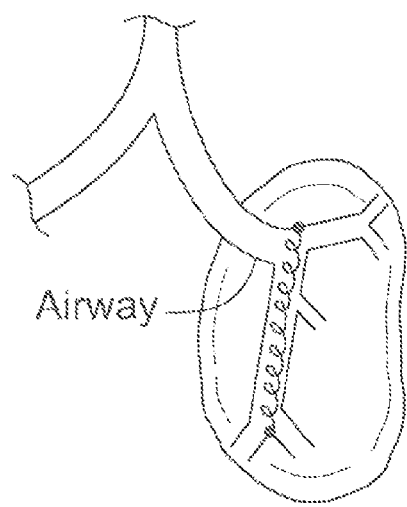

In another variation for reducing the volume of a tissue mass in a lung a mechanically elastic or elastic member may be applied to a lung, via an extra-anatomic opening or port in an airway wall. An elastic member may be affixed to tissue within a lung. For example, an elastic band or spring may be anchored at two points within a lung to compress the tissue therebetween. An elastic member or spring may have each end affixed or anchored to a different branch of an airway or to separate locations on or within an airway (See FIGS. 18A-18B).

The methods and devices described above and herein may be used for treating emphysema and/or other conditions.

Figure 19:
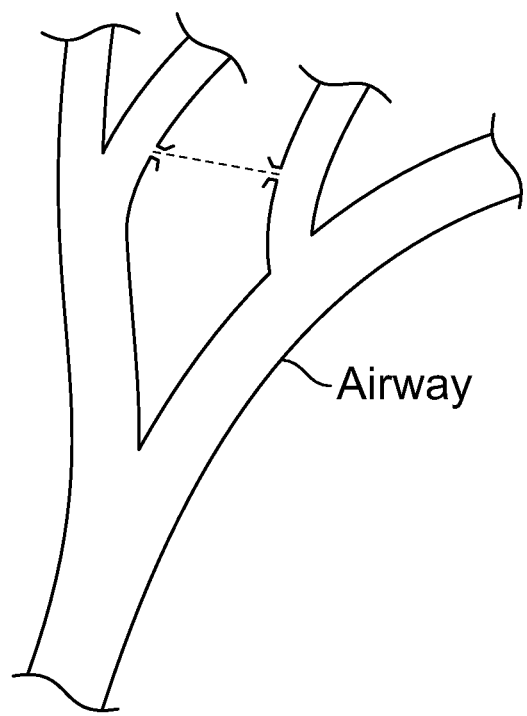
FIG. 19 illustrates a variation of a system or method utilizing multiple extra-anatomic openings or ports in an airway wall.

In another variation, a method for performing a minimally invasive procedure through one or more extra-anatomic openings or ports in an airway wall is provided. For example, as illustrated in FIG. 19, multiple extra-anatomic openings or ports may be provided at different locations in airway walls where one or more devices may be advanced through each of the extra-anatomic openings or ports. The devices may be triangulated through the various openings or ports to a target location or position to perform a desired procedure on a target tissue. The devices may be triangulated, positioned or located using a variety of imaging technologies or methods, including, e.g., video assistance, similar to the technique used for VAT procedures.

Figure 20:
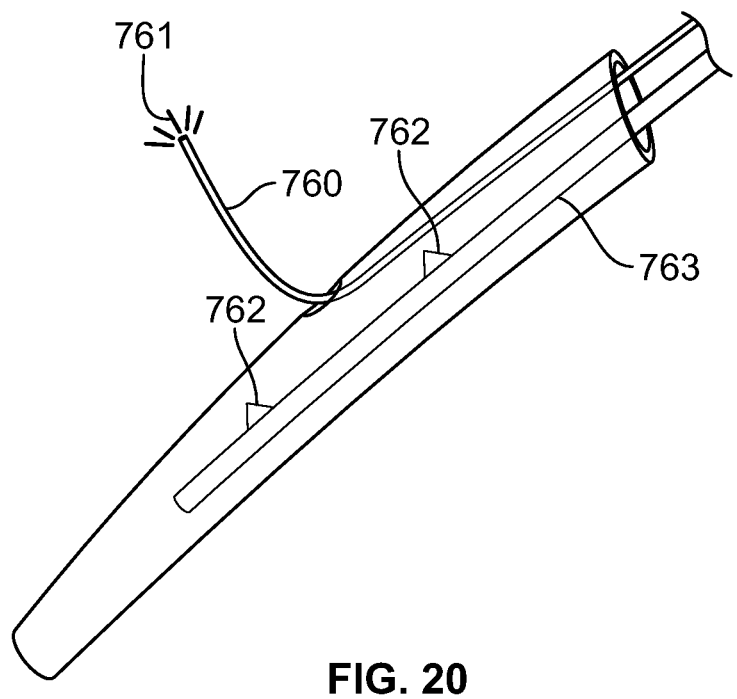
FIG. 20 illustrates a variation of a device and method for performing imaging.

FIG. 20 illustrates a variation of a device and method for performing imaging which can be used to determine the position of devices when performing procedures through a port in an airway wall. A coherent light source 761, e.g., a diode laser, may be placed on the tip of a first catheter 760 (e.g., a tx catheter) or treatment catheter, which catheter is advanced through an extra-anatomic opening or port in an airway wall. One or more sensors 762, e.g., two sensors, may be positioned on a second catheter 763, which catheter is positioned within an airway.

In use, differential light power may be utilized to triangulate in on the location of the tip of the first catheter 760. The sensors 762 may each sense a brightness of the light emitted from the light source 761 on the first catheter 760, through tissue, and the sensed brightness may be utilized to calculate the distance and direction of the first catheter 760, through tissue. Bright light can go through the airway wall, and tissue in general, allowing the sensors 762 to sense or detect the emitted light. Where the emitted light is coherent, wavelengths of the light may be measured to determine the distance of the catheter 760 and may provide an exact measurement of the distance of the first catheter 760 relative to the sensors 762. In certain variations, differential sensing with a or of a pulsing coherent light source may provide an exact distance measurement from the sensors, e.g., a distance measurement of the first catheter 760 relative to the sensors 762.

Figure 21:
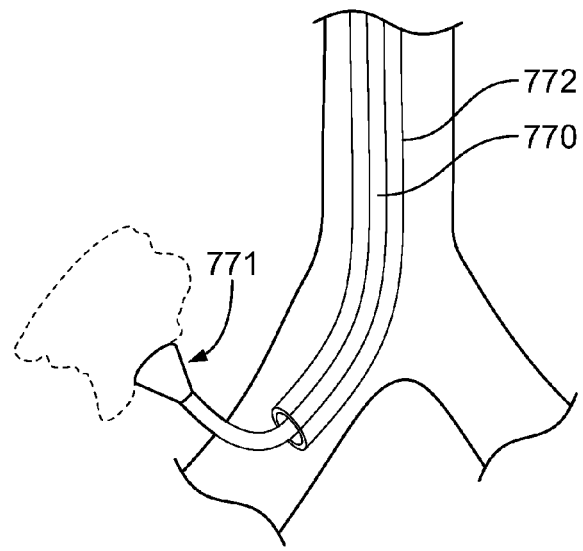
FIG. 21 illustrates a variation of a device and method for performing an ultrasound through an opening or port in an airway wall.

FIG. 21 illustrates a variation of a device and method for performing an ultrasound or other imaging through an extra-anatomic opening or port in an airway wall. A guided probe 770 having a front facing ultrasound transducer 771 may be advanced within an airway via a scope 772. The probe and/or ultrasound may be advanced through an extra-anatomic opening or port in an airway wall, and out of the airway into the lung tissue or parenchyma. The ultrasound may be used, e.g., to guide a biopsy procedure, or to visualize or guide other procedures, extraluminally or outside of the airway. The ultrasound may be utilized to take an image or shot of the tissue or parenchyma outside and/or behind the airway wall and/or to identify any areas for treatment. In another variation, one or more parameter of the ultrasound may be varied to improve the image or to deliver therapeutic doses of ultrasound to the tissue to change the properties of the tissue. In certain variations, an ultrasound guided extraluminal device may be provided.

In certain variations, a working channel may be established through an extra-anatomic opening or port in an airway wall and/or through lung tissue or parenchyma outside of the airway for performing procedures or extraluminal procedures. For example, after advancing ultrasound through an extra-anatomic opening or port in an airway wall and visualizing and identifying an area of interest in the lung tissue or parenchyma, a working channel may be established through the lung tissue or parenchyma, such that other instruments or tools may be advanced or returned to the area of interest for performing various extraluminal procedures, e.g., biopsy.

In another variation, a device and method for removing a nodule from lung tissue or parenchyma via an extra-anatomic opening or port in an airway wall is provided. The device may include an elongated member, e.g., a catheter or coil, having a cutter, e.g., a rotational cutter, at its distal end. In use, the catheter may be advanced through an extra-anatomic opening or port in an airway wall to a target nodule, tumor or other tissue. The cutter may morcellate, chew, or breakup the nodule or tumor. Chunks of the tumor are then pulled through the catheter and removed through the extra-anatomic opening or port in the airway wall. The nodule or other tissue may be removed via a catheter and/or bronchoscope.

Figure 22:
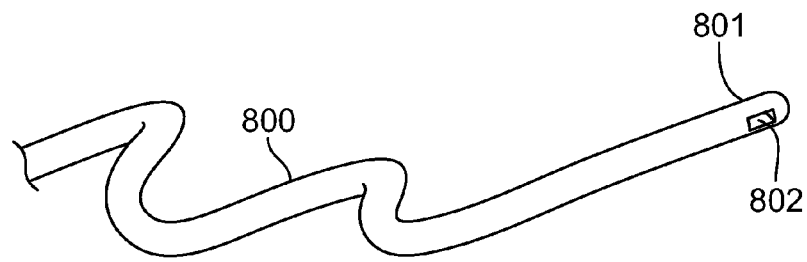
FIG. 22 illustrates one variation of a cutting catheter which may be advanced through an opening or port through an airway wall for the removal of various tissue.

FIG. 22 illustrates one example of a cutting catheter which may be advanced through an extra-anatomic opening or port through an airway wall for the removal of nodules, cancerous tissue or other tissue. Flexible catheter 800 includes a cutting tip 801 and may have a catheter housing (not shown), providing a tube within a tube configuration. The cutting tip may include a cutting window 802. For example, a sharpened cutting window 802 may be opened upon rotation of the cutting catheter within a housing, which causes tissue in the window to be cut. Cut tissue may then be suctioned through the catheter lumen. Fluid may be used to assist in the removal of cut tissue. The catheter may be flexible with rotational stiffness. A rotating member may rotate the catheter 800 within the catheter housing. The catheter may provide cutting action in multiple directions. For example, a catheter may provide rotational cutting action and/or front facing cutting action (e.g., where the catheter has an auger tip. Tissue may be captured between an exposed auger and a cutting edge. A catheter may be made of nitinol and/or include coil springs. In certain variations, rotation of the catheter may transport removed material axially down and through a catheter lumen for removal from a patient's body.

Figure 23:
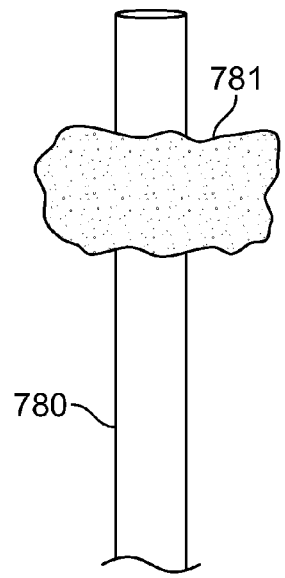
FIG. 23 illustrates a variation of a catheter for delivering a sealant.

FIG. 23 illustrates a variation of a device and method, including a catheter 780 and a sponge 781 attached to the catheter 780. A sealant material, e.g., a glutaraldehyde based cement may be placed on the sponge 781. In use, the catheter 780 with sponge 781 having a sealant material may be advanced through an extra-anatomic opening or port in an airway wall and into a track made previously in the lung tissue or parenchyma by a catheter or other instrument to take a biopsy, or bx sample or to remove tissue. Delivery of the sealant material along the track seals the track in order to prevent the occurrence of a pneumothorax or air leak in the lung. Alternatively, the sealant material may be delivered from the tip of a catheter inserted through the extra-anatomic opening or port. The tip of the catheter may include small holes to allow the sealant to be dispersed evenly. The holes may also be disposed about the circumference of the distal end of the catheter.

Figure 24:
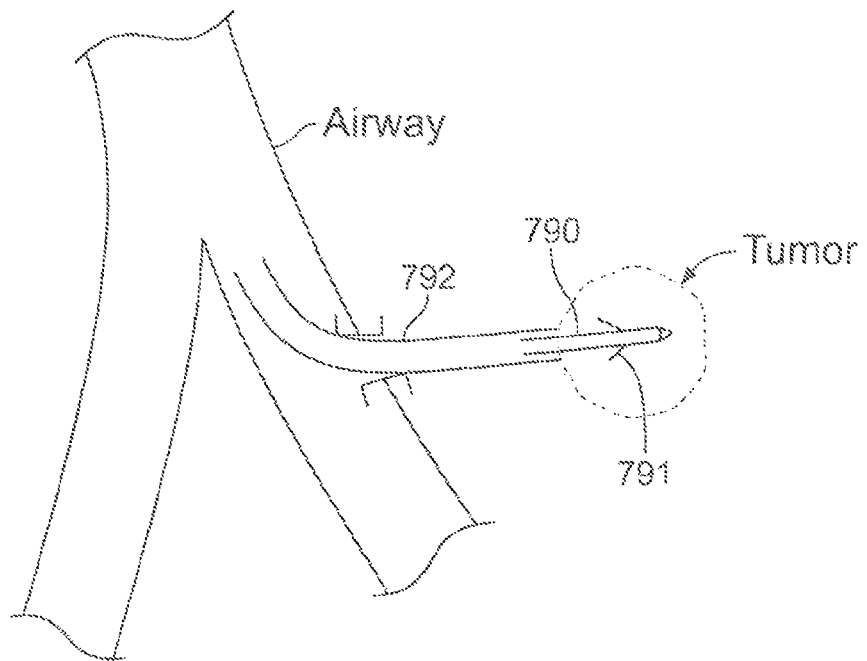
FIG. 24 illustrates a variation of a biopsy or tissue sampler.

FIG. 24 shows a variation of a biopsy sampler. The biopsy sampler has a catheter 790. Actuateable anchors 791 or barbs are positioned at the distal end of the catheter 790. In use, the catheter 790 may be advanced through an airway and introduced through an extra-anatomic opening or port in an airway wall, into the lung tissue or parenchyma. The catheter 790 may be introduced through a sheath 792 positioned through the extra-anatomic opening or port in the airway wall. The catheter 790 is advanced into a target tumor and the anchors 791 or barbs or scoops at the distal end of the catheter 790 are actuated or popped-out either before or after entry into the tumor. The catheter 790 is then pulled or drawn back toward the extra-anatomic opening or port in the airway wall, with the anchors 791 or barbs capturing the tumor or samples of the tumor, pulling the tumor or tumor sample back toward the extra-anatomic opening or port, or through the extra-anatomic opening or port and into or through the airway for removal. Optionally, the anchors or barbs may be retracted or collapsed and the tumor, tumor sample or other tissue may be pulled out or removed through the extra-anatomic opening or port and/or through the airway.

In another variation, a platform for accessing tumors or other tissue in the lung through an extra-anatomic opening or port in the airway wall is provided. Various forms of real time imaging may be utilized such as CT, MRI, PET, ultrasound, or fluoroscopy. A catheter, e.g., a 21 Ga needle sampling (TBNA) catheter, may be fed through a working channel of a bronchoscope. A small needle size may minimize the risk of bleeding. A steerable or non-steerable sheath (e.g., 2.0 mm to 3.0 mm OD) may be fed over the needle, but also within the scope working channel to provide steering and protection against seeding cancerous cells back into the non-cancerous tissue as the needle is withdrawn from the tumor. Optionally, a Doppler probe may be fed through or next to the needle lumen and may be utilized to sense and/or avoid blood vessels.

Lung tumors may be located deep in the lung tissue where they may require the winding or snaking of catheters through very tortuous airways or around various structures to access the tumor. When a catheter is fed deep enough in the airways to be as close as possible to a tumor, it may not be possible to articulate the catheter to point it directly at or in the direction of the tumor because the airway at that point is very narrow.

Therefore, in certain variations, an access platform for accessing target tissues (e.g., diseased tissue, tumors, parenchyma or other tissues or structures) in a lung or other area of the body, through an opening, extra-anatomic opening or port through the airway wall is provided. The target tissue or structures may be located outside of the airway in which the opening is created or beyond the airway wall, e.g., in the parenchyma of the lung.

In one variation, an approach to access a target tissue (e.g., diseased tissue, tumors, parenchyma or other tissues or structures) in the lung may utilize a more "straight-line" or substantially straight path. A path may be straight or substantially straight, allowing for some or no turns. Access to the central airways may be achieved by using a standard bronchoscope or other scope or elongate instrument. Instead of feeding the bronchoscope deep into the smaller airways of the lungs where manipulation or articulation of the scope may be reduced or eliminated, a target site or point in a larger airway or central airway may be determined or selected, which may allow a straight, semi-straight or substantially straight tunnel, channel or path to be created leading directly to the target tissue, parenchymal tissue or tumor. The target site or point on the airway wall may be located in an area of the airway where a standard scope or access tool, e.g., one having a diameter from about 0-5 mm, may be articulated, manipulated or turned at various degrees, e.g., 90 degrees, such that within the airway the scope or access tool may be oriented to point or face in the direction of or directly at the target tissue in the lung, e.g., a tumor. From this target site on the airway wall, an elongate instrument or other tool may be advanced through an opening in the airway wall to the target tissue or tumor in the lung in a substantially straight path or path that minimizes or reduces the number of turns and twists required to reach or access the target tissue or tumor while traveling through the parenchymal or lung tissue.

The target site or point, which also may be called a point of entry or POE, may be determined by taking into account or considering one or more of the following factors: (1) the size of the airways; (2) the outer diameter of a bronchoscope or other scope used to advance an elongate instrument or other tool or instrument in the airway; (3) the amount of room or space available within the airway to articulate the scope so that the scope working channel or elongate instrument can point towards the target tissue or tumor, (4) the position of blood vessels in the lung; (5) the location of pleural surfaces within the lung; (6) the location of other airways in the lung, and/or (7) the location, size, and shape of the target tissue or tumor. The POE location may be calculated by software algorithms or determined by visually assessing the factors stated above. Software algorithms may also be utilized to determine the direction or orientation of the tunnel, channel or path from the POE to the target tissue in 3D space.

Once the POE and tunnel, channel or path direction or orientation is determined, a needle or other piercing member may be fed from the working channel of the scope to make a hole through the airway wall at the POE. This may be followed by a balloon catheter or mechanical dilator to dilate the hole or opening. Alternatively, other means may be used to create a hole big enough to allow subsequent passing of other larger diameter tools. For example, a circular punch, a flat blade with a pointed tip, a cross shaped blade with a sharpened tip, an RF probe, or an RF snare may be used to create a slit, slits, or a larger opening in the airway wall without employing a dilation balloon. Once the hole has been dilated, a sheath or other elongate instrument may be fed through the hole or opening and into the lung tissue. The sheath may contain a dissecting catheter which may fill the entire or substantially entire internal diameter of the sheath so that when the sheath is fed through lung tissue, matter does not accumulate inside the sheath. The tip of the dissecting catheter may be sharp to tunnel through tissue or it may be rounded to allow it to tunnel without perforating blood vessels or other structures. The rounded tip may easily push through the less dense parenchymal tissue, and simply push more dense vessels or other structures out of the way without damaging them. The tip may tunnel or advance through the lung tissue in substantially straight path where turns are minimized or eliminated. Once the sheath and dissecting catheter are fed to the target tissue or tumor, the dissecting catheter may be removed, leaving the sheath in place to be used to access the target tissue or tumor for monitoring, diagnostic, or therapeutic procedures or for the delivery of other tools to the target tissue to perform various procedures.

In the variations above, the order of introducing each of the devices may vary. For example, the needle and sheath may be fed through a bronchoscope or scope or other delivery instrument simultaneously. Once a needle is used to make the hole or opening in the airway wall, the needle may be replaced by a balloon, and then a balloon may be replaced by a dissection catheter while the sheath remains in place. Various features of these devices may be combined into a single device, for example, the balloon may be mounted to the outside diameter of the needle.

In the variations above, various forms of real time imaging may be used to guide the sheath to the target tissue or tumor. For example, CT, MRI, PET, ultrasound, fluoroscopy or electromagnetic fields may be used. The sheath or other devices may be rendered radiopaque, or radiopaque marks may be placed on the sheath or other devices to provide visibility while utilizing these imaging modalities. Also visible marks may be placed on the outside of the devices so that the physician using the devices may measure the depth that the devices are fed into the lung tissue by watching the marks as they are fed into the hole in the airway wall.

In the variations above, steerability may be designed into any or all of the devices. For example, the sheath may be made steerable by including off-center-axis pull wires to allow the tip or distal end to be steered in one or multiple planes.

In the variations above, various methods may be used to avoid perforating blood vessels. Catheter, sheath or other elongate instrument mounted transducers may be used to listen for blood using the Doppler principle or ultrasound imaging may be employed. These methods may be fed through the channel of a piercing member or needle, or through the elongate instrument or sheath prior to introduction of the piercing member or needle. Alternatively, the methods or devices for avoiding or detecting blood vessels may be fed next to the piercing member or needle or be incorporated into one or more of the other elongate instruments or devices described.

In an alternative variation, the elongate instrument or sheath device and/or method described above may be used in therapeutic procedures. For example, an RF snare catheter may be fed through the sheath, where the sheath prevents cancerous cells from being seeded into healthy tissue as they are removed with the RF snare catheter. In another variation, a catheter having a rotating morcellating tip may be fed through the sheath and used to remove the tumor through the sheath. The sheath prevents cancerous cells from being seeded into healthy tissue as they are removed. The access sheath may also be used to introduce a needle or blunt catheter for injecting agents, e.g. chemotherapy drugs, directly into or the tumor or infusing the local space around the tumor with these agents. The access sheath may also be used to introduce a radioactive substance, e.g. seed, fluid, etc. directly into the tumor or infusing/implanting the local space around the tumor with these substances.

Additional diagnostic procedures that may be performed through an extra-anatomic opening or port through an airway wall include (1) injecting dye which is taken up by tumors (e.g., a radioactive dye linked to an antibody) to visualize and locate a tumor, (2) injecting a photodynamic therapy agent (PDT) directly into a tumor and illuminating the tumor with an LED mounted on a catheter, positioned in close proximity to the tumor to visualize the tumor, (3) implanting a device or beacon or tracking device or RFID into a tumor or target tissue that detects changes in the tumor or tissue growth or properties and reports back such that tumor or tissue may be monitored or tracked over time.

In certain variations, brachytherapy may be performed or a radiation seed may be placed through an extra-anatomic opening or port in an airway wall and positioned in lung tissue, parenchyma, or other tissue. For example, a small radiation or energy capsule may be advanced through an extra-anatomic opening or port in an airway wall and into or next to a target tumor, lung tissue, or parenchyma where the capsule may be activated to release energy or radiation. The capsule may be activated chemically, electronically, or may be activated from the outside with energy, causing the capsule to release local energy to treat a target tissue or tumor. In certain variations, focused energy may be delivered to the capsule, magnifying the release of energy from the capsule to treat target tissue. Optionally, a regimen may be utilized where the delivery of energy causes the release of different forms of energy or therapeutics locally to a target tissue at varying times or simultaneously and/or in different amounts.

In another variation, methods and device are provided for treating lung tumors performed through an extra-anatomic opening or port through an airway wall. A coil or electrodes from a coil or another device which can generate an alternating current is implanted into the tumor and excited or activated by an external electromagnetic or magnetic field. The coil or other device delivers energy into the tumor and heats or ablates the blood vessels supplying blood to the tumor. A repetitive localized heating of the tumor may be provided. The coil may be excited periodically, e.g., every few days, and eventually the tumor may be killed as the blood vessels are destroyed and can no long supply blood to the tumor. Microwaves or a lower frequency, e.g., 30-60 hertz may be used to destroy the tumor blood vessels. The device and method may allow for repetitive localized heating of a tumor. The procedure may take a few seconds and may cause minimal to no pain.

In another variation, immunotherapy may be performed through an extra-anatomic opening or port in an airway wall where an immune response is stimulated by activating tumor tissue with RF or another energy source. The immune system will then be activated and destroy any remaining tumor cells. The body becomes immunized against that tumor cell wherever else it may reside in the body.

In another variation, a capsule with a chemotherapy drug may be positioned at a target tissue and a magnetic or electromagnetic field may be applied which causes the capsule to release a desired amount of the drug. In another variation, an implantable drug pump, e.g., for delivering a chemotherapy drug, or an implantable stimulation device for delivering a stimulating or destructive current to a target tissue or tumor may be advanced through an extra-anatomic opening or port in an airway wall and implanted in tissue or parenchyma. The stimulation device may be powered by varying sources, e.g., battery powered or powered by an external power source or electromagnetic or magnetic field. Optionally, the stimulation device may deliver RF, laser, or another energy source to the target tissue or tumor.

Figure 25A:
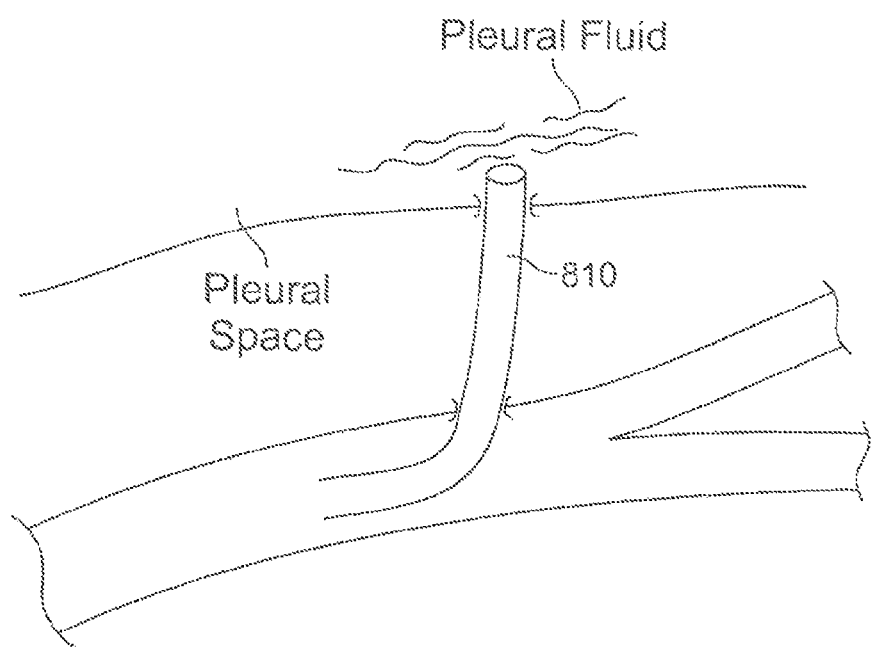
FIGS. 25A-B illustrate variations of a method and a device for performing a pleurocentesis.

In another variation, a method and a device for performing a pleurocentesis are provided. The pleurocentesis may be performed by entering the lung through an extra-anatomic opening or port in an airway wall. A drainage channel 810 may be created to drain fluid from the pleural space. As illustrated in FIG. 25A, the drainage channel 810 may be created by advancing a catheter or tube into the periphery airways and through an extra-anatomic opening or port in an airway wall, where the opening or port is positioned in close proximity to a fissure. The catheter or tube is advanced into the fissure and fluid in the pleural space may be suctioned or drained out via the catheter or tube.

Figure 25B:
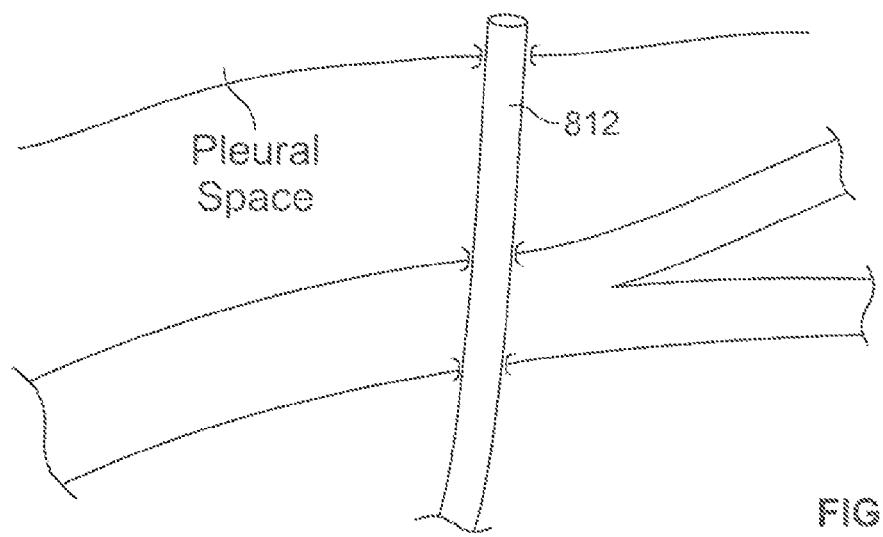

Alternatively, as illustrated in FIG. 25B, instead of sucking fluid from the pleural space, a first end of a catheter or tube may be inserted into a fissure and a second end of the catheter or tube may be inserted into the venous or lymphatic system to create a bypass drainage channel 812, directing or draining the fluid from the pleural space into the venous or lymphatic system. The bypass drainage channel prevents fluid collection in the pleural space, allowing the fluid to automatically drain. This device and method may be useful for treating conditions where the recurring build up of fluid in the pleural space is common, e.g., in patients suffering from lung cancer.

In other variations, various devices and methods are provided for treating pulmonary hypertension through an extra-anatomic opening or port in an airway wall. In one variation, a vasodilator, e.g., Viagra®, may be delivered to the lung to cause vasodilatation and reduce pulmonary hypertension. In another variation, a fistula or shunt may be positioned between a vein and artery inside the lung, either peripherally or centrally. The fistula provides a bypass between the artery and vein, which reduces resistance to blood flow through the artery and thereby reduces pressure in the artery. The artery and vein are positioned next to each other and a connector or shunt may be used to connect the vein and artery. In another variation, blood may be perpetually shunted from an artery to a vein according to the approach used by Rox Medical as follows: The ROX CO2UPLER™ device, a small metallic stent-like implant, couples two blood vessels together in the pelvic region. The implant creates a fistula, a calibrated passage, between the artery and vein, which allows a calculated amount of oxygen-rich blood to be rerouted from the artery to the vein, returning back to the heart and lungs for further increased oxygen saturation. The ROX FLO2W™ Procedure is a percutaneous interventional approach intended for treatment of patients with COPD.

Optionally, the above methods may be utilized for diagnosis. For example, while in the artery, blood pressure may be measured directly. Also, Doppler may be utilized to determine the distension range of an artery.

In other variations, devices and methods are provided for diagnosing, monitoring, or treating diabetes via an extra-anatomic opening or port in an airway wall. A device and method for performing noninvasive glucose monitoring may include an implantable glucose sensor positionable on an airway. A sensor may be positioned on the inside of the airway wall or the sensor may be advanced through an extra-anatomic opening or port in the airway wall and attached, anchored or clamped to the outside airway wall next to a vessel, e.g., a pulmonary artery or capillary. A sensor may be placed anywhere along the airway (inside or outside) in proximity to capillaries, arteries, blood vessels or other blood supply. The glucose levels may be detected and the sensor may send, transmit, or broadcast a signal to an external device, e.g., a cell phone, to collect and/or analyze the glucose related data. The glucose reading may be performed at preset time intervals or in response to an event, e.g., a skin prick or after food consumption. Optionally, an external energy source, e.g., a coil, may be coupled to a sensor or other internal device to supply energy so the sensor or internal device doesn't need its own energy source.

In other variations, a variety of sensors for taking various measurements by be utilized through extra-anatomic ports in the airway wall. For example, a sensor for measuring lactate levels, to detect infection or early warning indicators for pneumonia, or other respiratory problems may be utilized.

Pulmonary arterial hypertension may result from the proliferation and thickening of smooth muscle in the pulmonary artery, which may reduce the diameter of the arterial lumen and increase the pressure of the blood flow through the lumen. In another variation, an RF catheter may be advanced through an extra-anatomic opening or port in the airway wall, to a pulmonary artery. The RF catheter may be introduced into a pulmonary artery to reduce smooth muscle in the pulmonary artery, to thereby increase the diameter of the artery lumen and treat pulmonary hypertension. The RF catheter may be used to treat the smooth muscle, eliminating smooth muscle which is replaced with fibrotic cells. Use of the RF catheter on narrow segments of the pulmonary artery may increase the luminal area in the artery or vessel and decrease the pressure of arterial flow. The RF catheter may include electrodes in an angioplasty style balloon to treat the arterial or vascular wall. This may reduce the creation of thrombosis that could result from direct contact between the electrode and the blood. The configuration of the electrode(s) on the RF catheter may be monopolar, bi-polar and may include a variety of array designs (baskets, mesh, electrode pairs, point electrodes, etc.).

In another variation, a device and method for stimulating a diaphragm or respiration is provided. The device may include an implantable pulse generator or pacer having leads or electrodes. The device is advanced through an extra-anatomic opening or port in the airway wall and implanted in the lung. The device includes CO2 sensors, such that the device stimulates breathing in response to detected CO2 levels. This device may be used in patients suffering from emphysema, increasing the patient's respiratory effort when their CO2 levels start to rise. The device may also be used in patients who have suffered spinal cord injuries, paralysis, or who have MS, or other conditions where the patient requires a stimulated increase in respiration.

In another variation, a device and method for treating patient's having esophageal motility issues, where their esophagus doesn't squeeze or constrict properly causing food to get lodged in the esophagus, is provided. For example, a method for treating esophageal motility problems includes performing electronic pacing or stimulation of the esophagus through an extra-anatomic opening or port in the airway wall and through the pleura of the lung, which sits in proximity to or along the esophagus.

In another variation, a lapband or other restrictive device may be advanced through an extra-anatomic opening or port in the airway wall and through the lung or through the trachea, and positioned around the esophagus to constrain the esophagus and restrict the rate at which food may pass through the esophagus. Such a device may assist in the treatment of obesity or other conditions related to obesity.

In another variation, methods and devices are provided for facilitating improved VQ (V=perfusion; Q=ventilation) matching. Blood vessels may be accessed via an extra-anatomic opening or port through an airway wall. The blood vessels that are feeding areas of the lung that are poorly ventilated may be partially or completely closed off, redirecting blood to areas of the lung that are better ventilated. As a result, lung efficiency and overall perfusion/ventilation may be improved. In certain variations, blood vessels may be cauterized, closing off the blood vessel. In other variations, a wire, e.g., a nitinol wire, may be used to close off a blood vessel. Optionally, a U loop may be advanced through a first extra-anatomic opening or port in the airway wall, around a blood vessel, and back into the air way though the first or a second extra-anatomic opening or port in the airway wall. The U loop is cinched down, closing off or partially closing off the blood vessel.

In another variation for applying a therapeutic treatment via an extra-anatomic opening or port in an airway wall, a drug delivery capsule, pump, patch, or sponge may be advanced through the opening or port and implanted into parenchyma or other tissue. The capsule, etc. may deliver drugs over a period of time and may include a refillable or reloadable reservoir.

Figure 26:
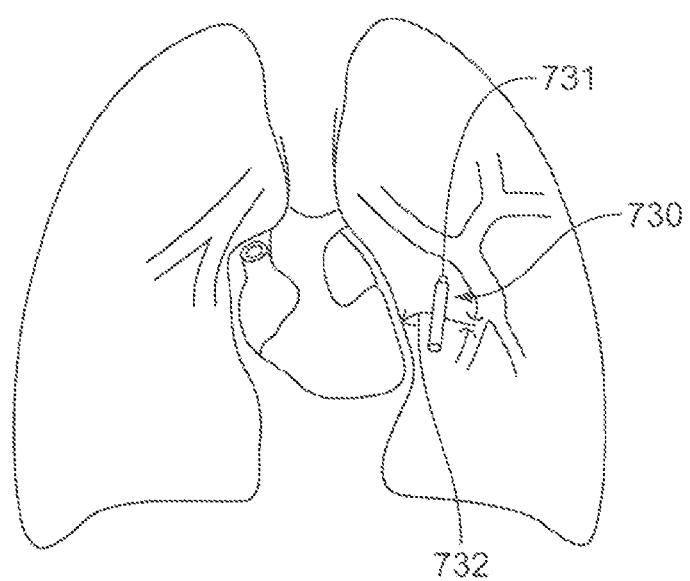
FIG. 26 illustrates a variation of a pacing device which may be advanced through an opening or port through the airway wall.

FIG. 26 illustrates a variation of a pacing device which may be advanced through an extra-anatomic opening or port through the airway wall. The device may be in the form of a leadless pacemaker 730 or defibrillating device. The leadless pacemaker may use the pacemaker metal case or can as a first lead and the pleura, which rests against or in close proximity to the heart, as a second lead. FIG. 26 shows a first electrode 731 placed on the metal case or can and a second electrode 732 placed on the pleura. In use, the pacemaker 730 may be advanced through an extra-anatomic opening or port in an airway wall and positioned in the lung to provide stimulation through the pleura, into the heart.

A variety of other procedures may be performed through an extra-anatomic opening or port or channel through an airway wall including for example: In one variation, a catheter may generate ultrasound and an image may be obtained from behind the catheter or tumor to localize a tumor. In another variation, markers could be placed on a periphery of a tumor or nodule and the volume of the nodules may be detected based on the fact that if the tumor or nodule is growing, the markers will separate from one another. In another variation, a sensor may be positioned outside of the body and catheter on the inside of the body that generates x-rays, ultrasound, light or other modality which provides a shadow of a mass, which you can then use to localize the mass. The generating catheter may be moved closer and closer to the tumor to localize the mass by observing how the shadow moves. In another variation two catheters may be positioned in two different areas of the lung. One catheter may shine light toward the other such that the size of the shadow cast by the light emitting catheter on the other catheter may be seen. This would provide a way to track size or locate a target tissue, mass or object. In certain variations, a tumor may be encapsulated or frozen by cryogenic procedures. In certain variations, blood vessels feeding a tumor or other tissue may be located and ablated, e.g., using hot biopsy forceps or a cauterizing knife or other ablation tool. Feeding vessels to a heterogeneous lobe may be ablated. In certain variations, a ziptie or gastro-type band may be positioned around a nodule or a vessel leading to a poorly ventilated area of the lung.

In any of the variations described therein, elongate instrument may refer to a catheter, sheath, scope, bronchoscope piercing member or any other medical device for insertion into the body. Optionally, any of the procedures described herein may be performed during or after the creation of a channel, opening, extra-anatomic opening or port through an airway wall.

In certain variations, a method of accessing target tissue in a lung is provided which includes locating a target site on an airway wall, wherein the target site is in a location that allows for creation of an opening leading to the target tissue and for advancement of an elongate instrument through the opening to the target tissue. The opening may be made through the airway wall at the target site. The target tissue may be located outside of the airway or beyond the airway wall through which the opening is made. The target site may be in a location that allows for advancement of an elongate instrument to the target tissue along a substantially straight path. The target site may be in a location that allows for advancement of an elongate instrument from the opening in the airway wall to the target tissue along a substantially straight path.

In certain variations, the target site may be determined or selected by considering one or more of the following factors: a size of the airway; an outer diameter of a scope used to advance the elongate instrument in the airway; space available within the airway to articulate a scope so that the scope working channel can point towards the target tissue; a position of blood vessels in the lung; a location of pleural surfaces within the lung; a location of other airways in the lung; and/or a location, size, and/or shape of a target tissue. The target site may be in a location that allows for the creation of a substantially straight tunnel or channel leading from the target site or opening to the target tissue. Locating a target site on the airway wall may include determining a direction or orientation of a tunnel or channel in space, the tunnel or channel leading from the airway wall to the target tissue in a substantially straight line or path.

In certain variations, a method of accessing target tissue in a lung may include: advancing an elongate instrument to a target site in an airway of the lung; creating an opening through the airway wall at the target site, where the opening leads to the target tissue; and advancing the elongate instrument through the opening to the target tissue. The elongate instrument may be advanced to the target tissue along a substantially straight path. The elongate instrument may be advanced from the opening in the airway wall to the target tissue along a substantially straight path. A method of accessing target tissue in a lung may include: locating a target site on an airway wall, wherein the target site is in a location that allows for creation of an opening through the airway wall, that leads to the target tissue, and for advancement of the elongate instrument through the opening to the target tissue. The elongate instrument may be advanced to the target tissue along a substantially straight path.

In certain variations a method of accessing target tissue may include one or more of the following: creating an opening through the airway wall at the target site by advancing a piercing member to the target site and through the airway wall; dilating the opening with a balloon catheter or other expandable device; advancing an elongate instrument through the opening to the target tissue; articulating the elongate instrument within the airway such that a distal end of the elongate instrument points in a direction facing the target tissue before the elongate instrument advances through the opening; advancing a dissecting catheter having a sharp or rounded tip positioned within the elongate instrument through the opening and to the target tissue; leaving the elongate instrument in place to provide access to the target tissue for performing monitoring, diagnostic or therapeutic procedures or for delivering instruments or tools to the target tissue; performing imaging to guide the elongate instrument to the target tissue. The imaging method used may be comprised of at least one of: fluoroscopy, computed tomography, positron emission technology, magnetic resonance imaging, or ultrasound. The target tissue may be a tumor or diseased tissue.

In certain variations, a method of accessing target tissue in a lung may include selecting or locating a target site in an airway of the lung wherein the target site is in a location that allows for creation of an opening through the airway wall, the opening leading to the target tissue, and/or wherein the target site is in a location that allows for advancement of an elongate instrument through the opening to the target tissue along a substantially straight path; advancing an elongate instrument to a target site in an airway of the lung; creating an opening through the airway wall at the target site, the opening leading to the target tissue; advancing the elongate instrument and a blunt tipped dissecting catheter positioned within the elongate instrument through the opening and to the target tissue; leaving the elongate instrument in place to provide access to the target tissue for performing monitoring, diagnostic or therapeutic procedures.

In certain variations a system for accessing target tissue in a lung may include: a piercing member configured to create an opening through an airway wall at a target site on the airway wall, the opening leading to the target tissue; a dissecting catheter configured for advancement through the opening and for creating a channel through the lung to the target tissue; and an elongate instrument configured for advancement through the opening and the channel to the target tissue, wherein the elongate instrument is configured to provide access to the target tissue for performing monitoring, diagnostic or therapeutic procedures.

In certain variations, a method of navigating an elongate instrument through an opening in an airway wall to target tissue in the lung may include advancing an elongate instrument within an airway of the lung; advancing the elongate instrument through an opening in the airway wall; and providing an electromagnetic sensor to guide or track the elongate instrument.

In certain variations a method of accessing target tissue in a lung, may include locating a target site on an airway wall, wherein the target site is in a location that allows for creation of an opening leading to the target tissue and for advancement of an elongate instrument through the opening to the target tissue; and providing an electromagnetic sensor to guide or track the elongate instrument.

In certain variations the methods may also include applying an electromagnetic field in a vicinity of the electromagnetic sensor to guide or track the elongate instrument. The electromagnetic field may be registered to a 3D model of the lung which has been reconstructed from a set of radiographic images and the radiographic images may be from a CT scan. The electromagnetic sensor may be positioned at a distal end of the elongate instrument. The target site may be in a location that allows for advancement of an elongate instrument to the target tissue along a substantially straight path. The target site may be in a location that allows for advancement of an elongate instrument from the opening in the airway wall to the target tissue along a substantially straight path.

In certain variations the target site may be determined or selected by considering one or more of the following factors: a size of the airway; an outer diameter of a scope used to advance the elongate instrument in the airway; space available within the airway to articulate a scope so that the scope working channel can point towards the target tissue; a position of blood vessels in the lung; a location of pleural surfaces within the lung; a location of other airways in the lung; and/or a location, size, and/or shape of a target tissue. The target site may be in a location that allows for the creation of a substantially straight tunnel or channel leading from the target site or opening to the target tissue. Locating a target site on the airway wall may include determining a direction or orientation of a tunnel or channel in space, the tunnel or channel leading from the airway wall to the target tissue in a substantially straight line or path.

In certain variations a method of accessing target tissue may include one or more of the following: creating an opening through the airway wall at the target site by advancing a piercing member to the target site and through the airway wall; dilating the opening with a balloon catheter or other expandable device; advancing an elongate instrument through the opening to the target tissue; articulating the elongate instrument within the airway such that a distal end of the elongate instrument points in a direction facing the target tissue before the elongate instrument advances through the opening; advancing a dissecting catheter having a sharp or rounded tip positioned within the elongate instrument through the opening and to the target tissue; leaving the elongate instrument in place to provide access to the target tissue for performing monitoring, diagnostic or therapeutic procedures or for delivering instruments or tools to the target tissue; performing imaging to guide the elongate instrument to the target tissue. The imaging method used may be comprised of at least one of: fluoroscopy, computed tomography, positron emission technology, magnetic resonance imaging, or ultrasound. The target tissue may be a tumor or diseased tissue. The method may include guiding the elongate instrument or a dissecting catheter with the electromagnetic sensor or an electromagnetic field.

In certain variations a method of accessing target tissue in a lung may include: advancing an elongate instrument to a target site in an airway of the lung; creating an opening through the airway wall at the target site, the opening leading to the target tissue; advancing the elongate instrument through the opening to the target tissue; and guiding the elongate instrument with an electromagnetic sensor or an electromagnetic field. The elongate instrument may be advanced to the target tissue along a substantially straight path. The elongate instrument may be advanced from the opening in the airway wall to the target tissue along a substantially straight path.

In certain variations the method may include locating a target site on an airway wall, wherein the target site is in a location that allows for creation of an opening leading to the target tissue and for advancement of the elongate instrument through the opening to the target tissue.

In certain variations a method of accessing target tissue in a lung may include: selecting a target site in an airway of the lung wherein the target site is in a location that allows for creation of an opening through the airway wall, the opening leading to the target tissue, and wherein the target site is in a location that allows for advancement of an elongate instrument through the opening to the target tissue along a substantially straight path; advancing an elongate instrument to a target site in an airway of the lung; creating an opening through the airway wall at the target site, the opening leading to the target tissue; advancing the elongate instrument and a blunt tipped dissecting catheter positioned within the elongate instrument through the opening and to the target tissue; guiding the elongate instrument and dissecting catheter with an electromagnetic sensor or an electromagnetic field; and leaving the elongate instrument in place to provide access to the target tissue for performing monitoring, diagnostic or therapeutic procedures.

In certain variations a system for accessing target tissue in a lung may include: a piercing member configured to create an opening through an airway wall at a target site on the airway wall, the opening leading to the target tissue; a dissecting catheter configured for advancement through the opening and for creating a channel through the lung to the target tissue; and an elongate instrument configured for advancement through the opening and the channel to the target tissue, wherein the elongate instrument is configured to provide access to the target tissue for performing monitoring, diagnostic or therapeutic procedures; and a guiding system for guiding the elongate instrument and dissecting catheter with an electromagnetic sensor or an electromagnetic field.

All publications, patent applications, patents, and other references mentioned herein are incorporated by reference in their entirety. To the extent there is a conflict in a meaning of a term, or otherwise, the present application will control. Although variations of the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. It is also contemplated that combinations of the above described embodiments/variations or combinations of the specific aspects of the above described embodiments/variations are within the scope of this disclosure.

Each of the individual variations described and illustrated herein has discrete components and features which may be readily separated from or combined with the features of any of the other variations. Modifications may be made to adapt a particular situation, material, composition of matter, process, process act(s) or step(s) to the objective(s), spirit or scope of the present invention.

Methods recited herein may be carried out in any order of the recited events which is logically possible, as well as the recited order of events. Furthermore, where a range of values is provided, every intervening value between the upper and lower limit of that range and any other stated or intervening value in that stated range is encompassed within the invention. Also, any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise, all technical and scientific terms used herein have the same meaning as commonly understood by one of ordinary skill in the art to which this invention belongs.

This disclosure is not intended to be limited to the scope of the particular forms set forth, but is intended to cover alternatives, modifications, and equivalents of the variations described herein. Further, the scope of the disclosure fully encompasses other variations that may become obvious to those skilled in the art in view of this disclosure. The scope of the present invention is limited only by the appended claims.

We claim:

1. A method of accessing and treating a target tissue in a lung, the method comprising:
    creating an opening through an airway wall at a target site with a hole-making instrument, the opening leading to the target tissue;
    tunneling from the opening in the airway wall to the target tissue by advancing an elongate instrument and a dissector positioned therein from the opening to the target tissue;
    removing the dissector from the elongate instrument such that the elongate instrument defines an access channel to the target tissue; and
    treating the target tissue through the access channel defined by the previously positioned elongate instrument leading to the target tissue.

2. The method of claim 1, wherein the step of treating comprises removing the target tissue.

3. The method of claim 2, wherein the removing is carried out by snaring the target tissue with a tissue-snare catheter.

4. The method of claim 2, wherein the removing is carried out by morcellating the target tissue with a morcellating-tip catheter.

5. The method of claim 1, wherein the step of treating comprises ablating the target tissue with an energy-delivering catheter.

6. The method of claim 1, wherein the step of treating comprises destroying the target tissue.

7. The method of claim 6, wherein the destroying comprises injecting an agent into the target tissue.

8. The method of claim 7, wherein the agent comprises at least one of a chemotherapy drug and a radioactive substance.

9. The method of claim 6, wherein the destroying comprises advancing an implant into the target tissue.

10. The method of claim 9, wherein the implant is one selected from the group consisting of a capsule, coil, and electrode.

11. The method of claim 10, wherein the implant is a capsule, and the capsule is configured to release radiation.

12. The method of claim 11, wherein the capsule is activated by a mechanism selected from the group consisting of chemical and electronic mechanisms.

13. The method of claim 12, wherein the capsule is activated electronically from an energy source outside the body.

14. The method of claim 9, wherein the implant is an electrode and configured to deliver alternating current to the tumor.

15. The method of claim 14, wherein the electrode is activated from an external source selected from the group consisting of an electromagnetic and magnetic field.

16. The method of claim 14, wherein the electrode is excited repeatedly.

17. The method of claim 1, further comprising dilating the opening with a balloon catheter; and performing imaging to guide the elongate instrument to the target tissue.

18. The method of claim 1, wherein the target tissue is a tumor.

19. The method of claim 1, further comprising locating the target site on the airway wall, wherein the target site is in a location that allows for creation of the opening leading to the target tissue and for advancement of the elongate instrument through the opening to the target tissue along a substantially straight path.

20. The method of claim 1, further comprising articulating the elongate instrument.

* * * * *